(12) United States Patent
Deprets et al.

(10) Patent No.: US 7,632,952 B2
(45) Date of Patent: Dec. 15, 2009

(54) BENZOTHIAZOLES AND THE USE THEREOF AS MEDICAMENTS

(75) Inventors: Stéphanie Deprets, Paris (FR); Anke Steinmetz, Vitry sur Seine (FR); Odile Angouillant-Boniface, Paris (FR); Daniel Bezard, Bagnolet (FR); Jidong Zhang, Paris (FR); Yannick Benedetti, Rosny Sous Bois (FR); François Clerc, Antony (FR)

(73) Assignee: Aventis Pharma S.A., Antony (FR)

( * ) Notice: Subject to any disclaimer, the term of this patent is extended or adjusted under 35 U.S.C. 154(b) by 86 days.

(21) Appl. No.: 11/536,757

(22) Filed: Sep. 29, 2006

(65) Prior Publication Data

US 2007/0093488 A1 Apr. 26, 2007

Related U.S. Application Data

(63) Continuation of application No. PCT/FR2005/000761, filed on Mar. 30, 2005.

(30) Foreign Application Priority Data

Apr. 1, 2004 (FR) .................................. 04 03421

(51) Int. Cl.
*A61K 31/428* (2006.01)
*C07D 277/82* (2006.01)

(52) U.S. Cl. ...................................... 548/163; 514/367
(58) Field of Classification Search .................. 548/163
See application file for complete search history.

(56) References Cited

U.S. PATENT DOCUMENTS 4,639,463 A 1/1987 Rosner et al.

7,041,668 B2 5/2006 Clerc

FOREIGN PATENT DOCUMENTS

| DE | 25 41 752 | 3/1977 |
| EP | 0 115 039 | 8/1984 |
| EP | 1388341 A1 * | 2/2004 |
| JP | 05239026 A | 9/1993 |
| WO | WO99/24035 | 5/1999 |
| WO | WO00/26202 | 5/2000 |
| WO | WO 00/41669 | 7/2000 |
| WO | WO01/57008 | 8/2001 |
| WO | WO 02/076454 | 10/2002 |
| WO | WO 2007/036630 | 4/2007 |

OTHER PUBLICATIONS

Souillac, et al., Characterization of Delivery Systems, Differential Scanning Calorimetry in Encyclopedia of Controlled Drug Delivery, 1999, John Wiley & Sons, pp. 212-227.*
Vippagunta et al., Advanced Drug Delivery Reviews, 48 (2001), pp. 3-26.*
Davies et al, Inhibitor Binding to Active and Inactive CDK2: The Crystal Structure of CDK2-Cyclin A/Indirubin-5-Sulphonate, Structure, vol. 9, 389-397, May 2001.
Roy et al, Early Development of Cyclin Dependent Kinase Modulators, Current Pharmaceutical Design, 2001, 7, 1669-1687.
Toogood, Cyclin-Dependent Kinase Inhibitors for Treating Cancer, Med. Res. Rev., vol. 21, No. 6, 487-498, 2001.
U.S. Appl. No. 12/054,719, Nemecek et al., filed Mar. 25, 2008.
Bach et al, Synthesis of Ansa-Bridged Macrocyclic Lactams Related to the Antitumor Antibiotic Geldanamycin by Ring Closing Metathesis, Synlett 2002, No. 8, 1302-1304.

* cited by examiner

*Primary Examiner*—Laura L. Stockton
(74) *Attorney, Agent, or Firm*—Paul R. Darkes; Kelly L. Bender

(57) ABSTRACT

The invention especially relates to novel chemical compounds, especially novel benzothiazole derivatives, to compositions containing said compounds, and to the use thereof as medicaments.

18 Claims, No Drawings

BENZOTHIAZOLES AND THE USE THEREOF AS MEDICAMENTS

The present invention relates especially to novel chemical compounds, particularly novel benzothiazole derivatives, to compositions containing them and to their use as medicinal products.

More particularly, the invention relates to novel sulfonic esters of benzothiazoles with anticancer activity, via modulation of the activity of proteins, in particular of kinases.

At the present time, most of the commercial compounds used in chemotherapy are cytotoxic, which pose major problems of side effects and tolerance by the patients. These effects might be limited insofar as the medicinal products used act selectively on the cancer cells, with the exclusion of healthy cells. One of the solutions for limiting the adverse effects of chemotherapy may thus consist in using medicinal products that act on metabolic pathways or constituent components of these pathways, predominantly expressed in the cancer cells, and which are expressed little or not at all in healthy cells.

Protein kinases are a family of enzymes that catalyze the phosphorylation of hydroxyl groups of specific residues of proteins, such as tyrosine, serine or threonine residues. Such phosphorylations may largely modify the function of proteins; thus, protein kinases play an important role in regulating a wide variety of cell processes, especially including metabolism, cell proliferation, cell differentiation, cell migration or cell survival. Among the various cellular functions in which the activity of a protein kinase is involved, certain processes represent attractive targets for treating cancer diseases and also other diseases.

Thus, one of the objects of the present invention is to propose compositions with anticancer activity, by acting in particular on kinases. Among the kinases for which modulation of activity is desired, the cyclin-dependent kinases and Aurora-2 are preferred.

The progress of the cell cycle is often governed by cyclin-dependent kinases (CDK), which are activated by means of an interaction with proteins belonging to the cyclin family, this activation terminating with the phosphorylation of substrates and finally with cell division. In addition, the endogenous CDK inhibitors that are activated (INK4 and KIP/CIP family) negatively regulate the activity of CDKs. The growth of normal cells is due to a balance between the CDK activators (the cyclins) and the endogenous CDK inhibitors. In several types of cancer, the expression or the aberrant activity of several of these cell cycle regulators has been described.

Cyclin E activates the kinase Cdk2, which then acts to phosphorylate the protein pRb (retinoblastoma protein), resulting in an engagement in irreversible cell division and transition toward the S phase (PL Toogood, Medicinal Research Reviews (2001), 21(6) 487-498. The kinase CDK2 and possibly CDK3 are necessary for progress in the G1 phase and entry into the S phase. During the formation of a complex with cyclin E, they maintain the hyperphosphorylation of pRb to aid the progress of the G1 phase into the S phase. In complexes with cyclin A, CDK2 plays a role in inactivating E2F and is necessary for producing the S phase (T. D. Davies et al. (2001) Structure 9, 389-3).

The CDK1/cyclin B complex regulates the progress of the cell cycle between the G2 phase and the M phase. Negative regulation of the CDK/cyclin B complex prevents normal cells from entering the S phase before the G2 phase has been correctly and fully performed (K. K. Roy and E. A. Sausville Current Pharmaceutical Design, 2001, 7, 1669-1687).

A level of regulation of the activity of CDKs exists. Cyclin-dependent kinase activators (CAK) have a positive regulatory action on CDKs. CAK phosphorylates CDKs on the threonine residue to render the target enzyme fully active.

The presence of defects in molecules participating in the cell cycle results in activation of the CDKs and progress of the cycle; it is normal to wish to inhibit the activity of the CDK enzymes in order to block the cellular growth of cancer cells.

Many proteins involved in chromosome segregation and spindle assembly have been identified in yeast and *drosophila*. Disorganization of these proteins leads to the absence of segregation of the chromosomes and to monopolar or disorganized spindles. Among these proteins, certain kinases, including Aurora and IpI1, originating from *drosophila* and from *S. cerevisiae*, respectively, are necessary for segregation of the chromosomes and separation of the centrosome. A human analogue of yeast IpI1 has recently been cloned and characterized by various laboratories. This kinase, known as Aurora 2, STK15 or BTAK, belongs to the serine/threonine kinase family. Bischoff et al. have shown that Aurora 2 is oncogenic, and is amplified in human colorectal cancers (EMBO J, 1998, 17, 3052-3065). This has also been illustrated in cancers involving epithelial tumors such as breast cancer.

The present invention relates to novel benzothiazole derivatives. It thus relates to the use of benzothiazole derivatives as agents for inhibiting kinases and more particularly as anticancer agents. Among these, it preferably relates to sulfonic esters of benzothiazoles. It also relates to the use of said derivatives for the preparation of a medicinal product for treatment in man.

Among the prior art known to date describing sulfonic esters of benzothiazoles, mention may be made of the published patent application JP 0539036, which describes a process for preparing derivatives having the general formula below:

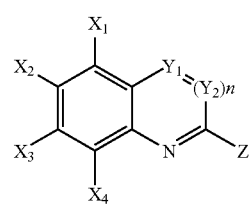

in which

Y$_1$ may represent a sulfur atom, n may be equal to zero,

Z may be an acylamino group the groups X$_1$, X$_2$, X$_3$ and X$_4$ are equal to H or may represent an alkylsulfonyloxy group.

Among the huge majority of compounds included in the general formula of the above-referenced patent, none of the examples describes compounds corresponding to the active compounds according to the invention, nor do they describe the synthesis of benzothiazoles.

The compounds according to the invention correspond to the general formula (I) below:

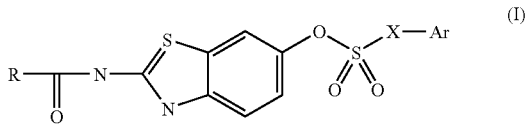

in which
- X represents a group chosen from a covalent bond, $(CH_2)_n$, with n equals to 1 or 2
- Ar represents an aryl or heteroaryl group; this group is optionally substituted with a group chosen from alkyl groups, halogens, $NR_1R_2$ ($R_1$ and $R_2$ being chosen from hydrogen groups, alkyls, cycloalkyls or may together form a heterocyclic or heteroaryl radical, these groups themselves being optionally substituted), $SO_2$alk, Salkyl, alkoxy, heteroaryl or aryl groups
- R represents a group chosen from hydrogen and an alkyl, cycloalkyl, heterocycloalkyl, aryl, heteroaryl, alkoxy, cycloalkoxy, heterocycloalkoxy or amino group; R may be optionally substituted with one or more groups chosen from the same radicals as those defined for R.

The possible substituents on the groups $R_1$ and $R_2$ are chosen especially from hydroxyl, heteroaryl, cycloalkyl and aminoalkyl groups.

For the purposes of the present invention, the term "alkyl group" means straight or branched chains containing 1 to 10 carbon atoms.

For the purposes of the present invention, the term "cycloalkyl group" means cyclic alkyl chains containing 3 to 10 carbon atoms.

For the purposes of the present invention, the term "heterocycloalkyl group" means cyclic alkyl chains containing 3 to 10 carbon atoms and containing at least one hetero atom chosen from O, N and S.

For the purposes of the present invention, the term "group $NR_1R_2$" means amino groups, preferably secondary amino groups, i.e. groups for which at least one of the substituents is hydrogen.

All these groups are optionally substituted with an alkyl, cycloalkyl, heterocycloalkyl, heteroaryl, aryl, amino, hydroxyl, alkoxy or halogen group.

For the purposes of the present invention, the term "aryl radical" and "heteroaryl radical" means monocyclic radicals optionally comprising one or more hetero atoms chosen from O, N and S or radicals fused to another 5- or 6-membered ring and optionally comprising 1 to 3 hetero atoms chosen from O, N and S. Preferably, among the aryl or heteroaryl radicals, mention may be made of phenyl, pyridyl, pyrimidine, triazine, pyrrolyl, imidazolyl, thiazolyl, furyl, thienyl, indolyl, azaindazolyl, isobenzofuryl, isobenzothienyl, benzoxazolyl, benzothiazolyl, arylvinylene, arylamido, arylcarboxamide, aralkylamine, quinolyl, isoquinolyl, cinnolyl, quinazolyl, naphthyridyl, triazolyl or tetrazolyl groups.

Among the aryl and heteroaryl groups, optionally substituted phenyl, thienyl, pyrazolyl or imidazolyl groups are preferably chosen.

Among the substituents of the phenyl group that are preferred are amino groups and halogens, in particular chlorine and fluorine, and thus, among the aryl groups, di- and trifluorophenyls and monoalkylaminophenyls are most particularly preferred, the alkyl chain being optionally substituted with a hydroxyl or dialkylamino group.

It is also preferred to choose, from among the compounds of formula (I), those for which X represents a covalent bond and those for which R represents a cycloalkyl radical.

Among the compounds corresponding to formula (I), mention may be made of the following compounds:

4-(2-hydroxy-2-methylpropylamino)benzenesulfonic acid 2-[(piperidine-4-carbonyl)amino]benzothiazol-6-yl ester;
4-fluorobenzenesulfonic acid 2-(cyclopropanecarbonylamino)benzothiazol-6-yl ester;
4-cyclopentylaminobenzenesulfonic acid 2-(cyclopropanecarbonylamino)-benzothiazol-6-yl ester;
4-(3-imidazol-1-ylpropylamino)benzenesulfonic acid 2-(cyclopropanecarbonyl-amino)benzothiazol-6-yl ester;
4-methylaminobenzenesulfonic acid 2-(cyclopropanecarbonylamino)-benzothiazol-6-yl ester;
4-(2-hydroxy-2-methylpropylamino)benzenesulfonic acid 2-(cyclopropane-carbonylamino)benzothiazol-6-yl ester;
4-(2-diisopropylaminoethylamino)benzenesulfonic acid 2-(cyclopropane-carbonylamino)benzothiazol-6-yl ester;
4-[4-(4-pyrid-3-ylimidazol-1-yl)butylamino]benzenesulfonic acid 2-(cyclo-propanecarbonylamino)benzothiazol-6-yl ester;
4-(2-isopropylaminoethylamino)benzenesulfonic acid 2-(2-piperid-4-ylacetyl-amino)benzothiazol-6-yl ester hydrochloride;
4-(3-imidazol-1-ylpropylamino)benzenesulfonic acid 2-(2-piperid-4-ylacetyl-amino)benzothiazol-6-yl ester hydrochloride;
4-(2-ethylaminoethylamino)benzenesulfonic acid 2-(2-piperid-4-ylacetyl-amino)benzothiazol-6-yl ester hydrochloride;
4-[2-(2-hydroxyethylamino)ethylamino]benzenesulfonic acid 2-(2-piperid-4-yl-acetylamino)benzothiazol-6-yl ester hydrochloride;
4-(2-hydroxy-2-methylpropylamino)benzenesulfonic acid 2-(2-piperid-4-yl-acetylamino)benzothiazol-6-yl ester hydrochloride;
4-(2-isopropylaminoethylamino)benzenesulfonic acid 2-(8-aminooctanoyl-amino)benzothiazol-6-yl ester hydrochloride;
4-(3-imidazol-1-ylpropylamino)benzenesulfonic acid 2-(8-aminooctanoyl-amino)benzothiazol-6-yl ester hydrochloride;
4-(2-ethylaminoethylamino)benzenesulfonic acid 2-(8-aminooctanoylamino)-benzothiazol-6-yl ester;
4-[2-(2-hydroxyethylamino)ethylamino]benzenesulfonic acid 2-(8-amino-octanoylamino)benzothiazol-6-yl ester hydrochloride;
4-(2-hydroxy-2-methylpropylamino)benzenesulfonic acid 2-(8-aminooctanoyl-amino)benzothiazol-6-yl ester hydrochloride;
4-(2-isopropylaminoethylamino)benzenesulfonic acid 2-(3-piperid-4-yl-propionylamino)benzothiazol-6-yl ester hydrochloride;
4-(3-imidazol-1-ylpropylamino)benzenesulfonic acid 2-(3-piperid-4-ylpropionylamino)benzothiazol-6-yl ester hydrochloride;
4-(2-ethylaminoethylamino)benzenesulfonic acid 2-(3-piperid-4-ylpropionyl-amino)benzothiazol-6-yl ester hydrochloride;
4-[2-(2-hydroxyethylamino)ethylamino]benzenesulfonic acid 2-(3-piperid-4-yl-propionylamino)benzothiazol-6-yl ester hydrochloride;
4-isobutylaminobenzenesulfonic acid 2-(2-piperid-4-ylacetylamino)benzo-thiazol-6-yl ester hydrochloride;
4-isobutylaminobenzenesulfonic acid 2-(3-piperid-4-ylpropionylamino)benzo-thiazol-6-yl ester hydrochloride;
4-isobutylaminobenzenesulfonic acid 2-(8-aminooctanoylamino)benzothiazol-6-yl ester hydrochloride;
thiophene-2-sulfonic acid 2-[(piperidine-4-carbonyl)amino]benzothiazol-6-yl ester; compound with trifluoroacetic acid;
thiophene-2-sulfonic acid 2-(3-piperid-4-ylpropionylamino)benzothiazol-6-yl ester; compound with trifluoroacetic acid;

thiophene-2-sulfonic acid 2-(2-aminoacetylamino)benzothiazol-6-yl ester;
thiophene-2-sulfonic acid 2-(2-methylaminoacetylamino)benzothiazol-6-yl ester; compound with trifluoroacetic acid;
thiophene-2-sulfonic acid 2-(3-aminopropionylamino)benzothiazol-6-yl ester; compound with trifluoroacetic acid;
thiophene-2-sulfonic acid 2-(8-aminooctanoylamino)benzothiazol-6-yl ester; compound with trifluoroacetic acid;
thiophene-2-sulfonic acid 2-(3-diethylaminopropionylamino)benzothiazol-6-yl ester; compound with trifluoroacetic acid;
thiophene-2-sulfonic acid 2-(cyclopropanecarbonylamino)benzothiazol-6-yl ester;
4-(2-diisopropylaminoethylamino)benzenesulfonic acid 2-[(azetidine-3-carbonyl)amino]benzothiazol-6-yl ester;
4-(2-diisopropylaminoethylamino)benzenesulfonic acid 2-(8-aminooctanoyl-amino)benzothiazol-6-yl ester;
4-(2-diisopropylaminoethylamino)benzenesulfonic acid 2-[(1-aminocyclo-pentanecarbonyl)amino]benzothiazol-6-yl ester;
4-(2-diisopropylaminoethylamino)benzenesulfonic acid 2-(2-piperid-4-yl-acetylamino)benzothiazol-6-yl ester;
4-(2-diisopropylaminoethylamino)benzenesulfonic acid 2-acetylaminobenzo-thiazol-6-yl ester;
4-(2-diisopropylaminoethylamino)benzenesulfonic acid 2-(2-methoxyacetyl-amino)benzothiazol-6-yl ester;
4-(2-diisopropylaminoethylamino)benzenesulfonic acid 2-(cyclopentane-carbonylamino)benzothiazol-6-yl ester;
4-(2-diisopropylaminoethylamino)benzenesulfonic acid 2-(6-aminohexanoyl-amino)benzothiazol-6-yl ester hydrochloride;
4-(2-diisopropylaminoethylamino)benzenesulfonic acid 2-(7-aminoheptanoyl-amino)benzothiazol-6-yl ester hydrochloride;
4-(2-isopropylaminoethylamino)benzenesulfonic 2-(cyclopropanecarbonyl-amino)benzothiazol-6-yl ester hydrochloride;
4-(2-diisopropylaminoethylamino)benzenesulfonic acid 2-isobutyrylamino-benzothiazol-6-yl ester hydrochloride;
4-(2-diisopropylaminoethylamino)benzenesulfonic acid 2-propionylamino-benzothiazol-6-yl ester hydrochloride;
4-(2-hydroxy-2-methylpropylamino)benzenesulfonic acid 2-propionylamino-benzothiazol-6-yl ester;
4-(2-diisopropylaminoethylamino)benzenesulfonic acid 2-(cyclobutane-carbonylamino)benzothiazol-6-yl ester hydrochloride;
4-fluorobenzenesulfonic acid 2-(3-pyridin-3-ylpropionylamino)benzothiazol-6-yl ester;
4-(2-diisopropylaminoethylamino)benzenesulfonic acid 2-(3-pyridin-3-yl-propionylamino)benzothiazol-6-yl ester hydrochloride;
4-(2-hydroxy-2-methylpropylamino)benzenesulfonic acid 2-(3-pyridin-3-yl-propionylamino)benzothiazol-6-yl ester hydrochloride;
4-(1-oxyl-2,2,6,6-tetramethylpiperidin-4-ylamino)benzenesulfonic acid 2-(cyclopropanecarbonylamino)benzothiazol-6-yl ester;
4-(2-hydroxy-2-methylpropylamino)benzenesulfonic acid 2-(3-piperidin-4-yl-propionylamino)benzothiazol-6-yl ester hydrochloride;
4-(2-diisopropylaminoethylamino)benzenesulfonic acid 2-butyrylamino-benzothiazol-6-yl ester hydrochloride;
4-(2-isopropylaminoethylamino)benzenesulfonic acid 2-butyrylamino-benzothiazol-6-yl ester; compound with trifluoroacetic acid;
4-(2-isopropylaminoethylamino)benzenesulfonic acid 2-isobutyrylamino-benzothiazol-6-yl ester; compound with trifluoroacetic acid;
4-(2-hydroxy-2-methylpropylamino)benzenesulfonic acid 2-butyrylaminobenzothiazol-6-yl ester hydrochloride;
4-(2-isopropylaminoethylamino)benzenesulfonic acid 2-propionylamino-benzothiazol-6-yl ester; compound with trifluoroacetic acid;
4-(2-isopropylaminoethylamino)benzenesulfonic acid 2-acetylaminobenzo-thiazol-6-yl ester;
4-(2-isopropylaminoethylamino)benzenesulfonic acid 2-acetylaminobenzo-thiazol-6-yl ester hydrochloride;
4-(2-isopropylaminoethylamino)benzenesulfonic acid 2-(2-methoxyacetyl-amino)benzothiazol-6-yl ester;
4-(2-isopropylaminoethylamino)benzenesulfonic acid 2-(cyclopentane-carbonylamino)benzothiazol-6-yl ester;
4-(2-isopropylaminoethylamino)benzenesulfonic acid 2-(cyclobutanecarbonyl-amino)benzothiazol-6-yl ester; compound with trifluoroacetic acid;
1-methyl-1H-imidazole-4-sulfonic acid 2-(cyclopropanecarbonylamino)benzo-thiazol-6-yl ester;
5-pyridin-2-ylthiophene-2-sulfonic acid 2-(cyclopropanecarbonylamino)benzo-thiazol-6-yl ester;
4-(2-methyl-2-phosphonooxypropylamino)benzenesulfonic acid 2-(cyclopropanecarbonylamino)benzothiazol-6-yl ester.

One of the processes for preparing the compounds according to the invention may be represented schematically in the following manner:

1. The compounds of formula (I) for which R=alkyl, cycloalkyl, aryl, or heteroaryl, may be prepared according to the synthetic scheme 1.

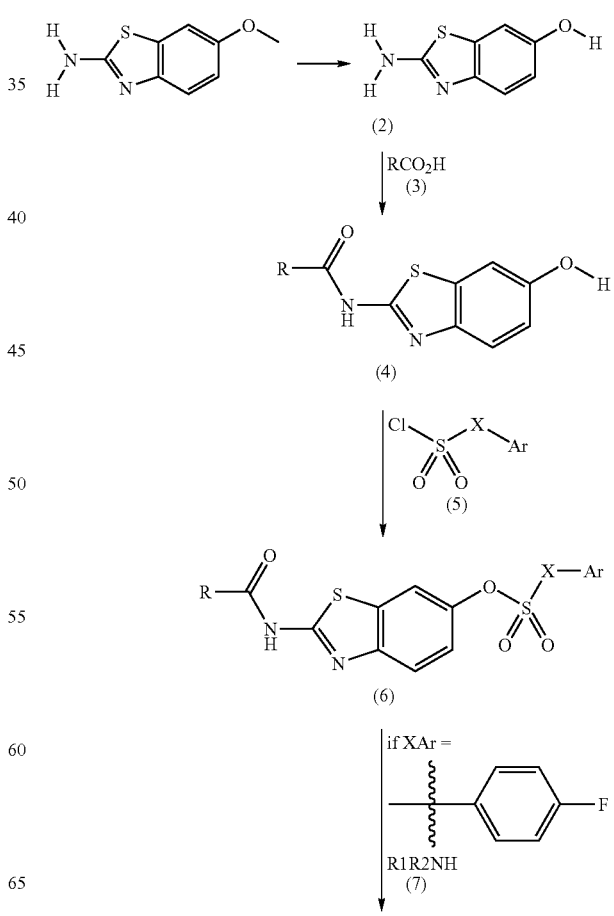

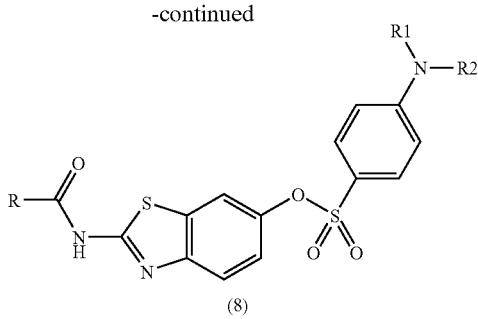

(8)

The compounds of the present invention may be readily prepared from 5-methoxybenzothiazol-2-ylamine (commercial compound).

In a first step, the starting material is demethoxylated in acidic medium, preferably in an acetic acid/aqueous hydrobromic acid mixture.

In a second step, the 5-hydroxybenzothiazol-2-ylamides (4) are obtained by reaction between 5-hydroxybenzothiazol-2-ylamine (2) and an acid of formula (3) (R as defined in the general formula (I)) in the presence of a coupling agent such as HATU or HBTU and of a base such as diisopropylethylamine or triethylamine, in a suitable solvent. Among the solvents that may be used, mention may be made of dimethylformamide and dichloromethane. The temperature of choice for performing this reaction is between room temperature and reflux point.

In a third step, the sulfono esters of formula (6) are obtained by reaction between the 5-hydroxybenzothiazol-2-ylamides (4) and a sulfonyl chloride of formula (5) (X and Ar as defined in the general formula (I)), in an inert solvent (acetone, THF, dichloromethane or toluene), in the presence of a base such as triethylamine or pyridine.

In the case where XAr corresponds to 4-fluorophenyl, the nucleophilic substitution of F with the amines of formula (7) (R1R2 as defined in the general formula (I)) to give the derivatives of formula (8) is performed in an aprotic solvent such as N-methylpyrrolidone or dimethylformamide, at a temperature ranging from 90 to 130° C., in a sealed tube or by microwave.

2. The compounds of the present invention for which R=alkoxy, cycloalkoxy or heterocycloalkoxy may be prepared according to the synthetic scheme 2.

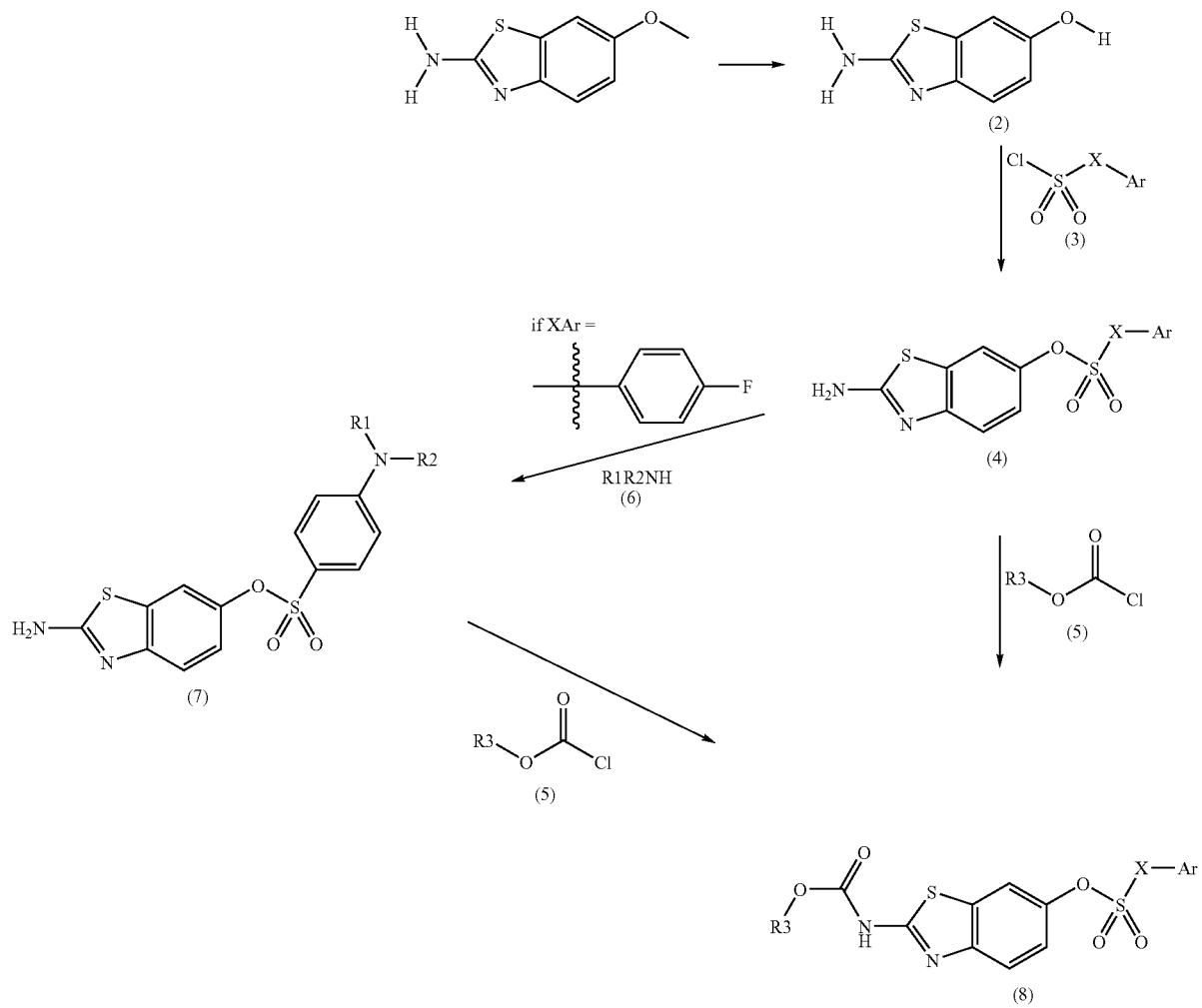

The compounds of the present invention may be readily prepared from 5-methoxybenzothiazol-2-ylamine (commercial compound).

In a first step, the starting material is demethoxylated in acidic medium, preferably in an acetic acid/aqueous hydrobromic acid mixture.

In a second step, the sulfono esters of formula (4) are obtained by reaction between 5-hydroxybenzothiazol-2-ylamine (2) and a sulfonyl chloride of formula (3) (X and Ar as defined in the general formula (I)) in an inert solvent (acetone, THF, dichloromethane or toluene), in the presence of a base such as triethylamine or pyridine.

In the case where XAr corresponds to 4-fluorophenyl, the nucleophilic substitution of F with the amines of formula (6) (R1R2 as defined in the general formula (I)) to give the derivatives of formula (7) is performed in an aprotic solvent such as N-methylpyrrolidone or dimethylformamide, at a temperature ranging from 90 to 130° C., in a sealed tube or by microwave.

The carbamates (8) are obtained by reaction between the amines of formulae (4) and (7) and a chloroformate of formula (5) (R3 as defined in the general formula (I)), in the presence of an organic base such as pyridine, triethylamine or diisopropylethylamine, or a mineral base such as potassium carbonate, in a suitable solvent. Among the solvents that may be used, mention may be made of tetrahydrofuran, dichloromethane and dioxane. The temperature of choice for performing this reaction is between 0° C. and the reflux point.

3. The compounds of the present invention for which R=alkylamino, cycloalkylamino or heterocycloamino may be prepared according to the synthetic scheme 3.

SCHEME 3

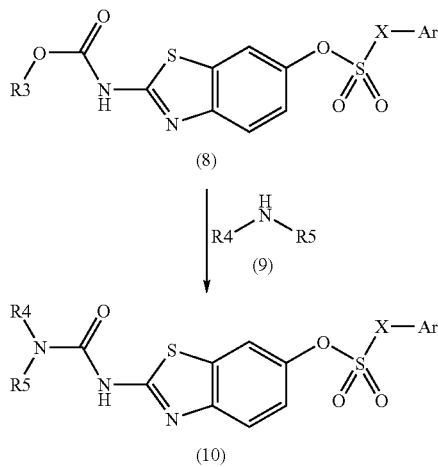

The ureas of formula (10) may be obtained by reaction between the carbamates of formula (8) (R3=Me, preferably) and an amine of formula (9) (R4 and R5 as defined in the general formula (I)), in an aprotic solvent such as N-methylpyrrolidone or dimethylformamide, at a temperature ranging from 90° C. to 130° C. in a sealed tube or by microwave.

The compounds according to the invention may be used in human therapy and more particularly in the case of cancer treatment, more particularly of cancers that are sensitive to Aurora-2 inhibitors and Cdk2 inhibitors.

The present invention will be described more completely with the aid of the examples that follow, which should not be considered as limiting the invention.

The DCI spectra were acquired by desorption-chemical ionization (reactant gas: ammonia, Finnigan SSQ7000 machine).

The electrospray (ES$^+$) spectra were acquired using a Platform II (Micromass) machine.

LC/MS Analysis

LC/MS Analysis Method (Method A1)

The LC/MS analyses were performed on a Micromass LCT model machine linked to an HP 1100 machine. The abundance of the products was measured using an HP G1315A diode array detector over a 200-600 nm wavelength range and a Sedex 65 light-scattering detector. The mass spectra were acquired over a range from 180 to 800. The data were analyzed using the Micromass MassLynx software. The separation was performed on a Hypersil BDS C18 column, 3 μm (50×4.6 mm), eluting with a linear gradient of from 5% to 90% of acetonitrile containing 0.05% (v/v) of trifluoroacetic acid (TFA) in water containing 0.05% (v/v) TFA over 3.5 minutes at a flow rate of 1 ml/minute. The total analysis time, including the column re-equilibration period, is 7 minutes.

LC/MS Analysis Method (Method A2)

The LC/MS analyses were performed on a Micromass Platform model machine. The abundance of the products was measured using an HP G1315A diode array detector over a 200-400 nm wavelength range and a Sedex 65 light-scattering detector. The mass spectra were acquired over a range from 50 to 1500. The data were analyzed using the Micromass MassLynx software. The separation was performed on an Xterral 3.5 μm (50×2.1 mm) column, eluting with a linear gradient of from 5% to 95% of acetonitrile in water containing 0.1% (v/v) of formic acid, over 9 minutes at a flow rate of 0.7 ml/minute. The total analysis time, including the column re-equilibration period, is 9 minutes.

Preparative LC/MS Purification (Method B):

The products were purified by LC/MS using a Waters FractionLynx system composed of a Waters model 600 gradient pump, a Waters model 515 regeneration pump, a Waters Reagent Manager dilution pump, a Waters model 2700 autoinjector, two Rheodyne LabPro model valves, a Waters model 996 diode array detector, a Waters model ZMD mass spectrometer and a Gilson model 204 fraction collector. The system was controlled by the Waters FractionLynx software. The separation was performed alternately on two Waters Symmetry columns ($C_{18}$, 5 μM, 19×50 mm, catalog reference 186000210), one column undergoing regeneration with a 95/5 (v/v) water/acetonitrile mixture containing 0.07% (v/v) trifluoroacetic acid, while the other column was performing separation. The columns were eluted using a linear gradient of from 5% to 95% of acetonitrile containing 0.07% (v/v) of trifluoroacetic acid in water containing 0.07% (v/v) trifluoroacetic acid, at a flow rate of 10 ml/minute. At the separation column outlet, one-thousandth of the effluent is separated by an LC Packing Accurate, diluted with methyl alcohol, at a flow rate of 0.5 ml/minute, and sent to the detectors, in a proportion of 75% to the diode array detector and the remaining 25% to the mass spectrometer. The rest of the effluent (999/1000) is sent to the fraction collector, where the flow is discarded as long as the mass of the expected product has not been detected by the FractionLynx software. The molecular formulae of the expected products are supplied to the FractionLynx software, which initiates the collection of the product when the mass signal detected corresponds to the ion [M+H]$^+$ and/or to [M+Na]$^+$. In certain cases, depending on the analytical LC/MS results, when an intense ion corresponding to [M+2H]++ was detected, the value corresponding to half the calculated molecular mass (MW/2) is also supplied to the FractionLynx software. Under these conditions, collection is also initiated when the mass signal of the ion [M+2H]++ and/or [M+Na+H]++ is detected. The products were collected in tared glass tubes. After collection, the solvents were evaporated off, in a Savant AES 2000 or Genevac HT8 centrifuge evaporator and the product masses were determined by weighing the tubes after evaporating off the solvents.

Purification by flash chromatography: The crude products are purified by flash chromatography on silica of particle size 15-35 μm under an argon pressure of 0.5 bar. The fractions corresponding to the expected product are combined and concentrated under reduced pressure on a rotary evaporator.

The present invention will be described more fully with the aid of the examples that follow, which should not be considered as limiting the invention:

INTERMEDIATE 1

Preparation of 2-aminobenzothiazol-6-ol

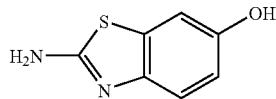

A solution of 2-amino-6-ethoxybenzothiazole (5 g, 25.74 mmol) and of 48% hydrobromic acid in water (130 ml, 1.141 mol) in 65 ml of acetic acid is distributed in ten 20 ml microwave tubes, and then heated at 150° C. by microwave for 200 seconds. The reaction medium is concentrated. The residue is taken up in 200 ml of water, basified to pH 8 by addition of 75 ml of saturated NaHCO₃ solution and extracted with ethyl acetate, washed with saturated sodium chloride solution, dried over magnesium sulfate and concentrated to dryness to give 3.4 g of 2-aminobenzothiazol-6-ol (gray powder).

LC/MS (method A1): [M+H]+=167.00, retention time: 1.07 min.

INTERMEDIATE 2

Preparation of 4-(6-hydroxybenzothiazol-2-ylcarbamoyl)-piperidine-1-carboxylic acid tert-butyl ester

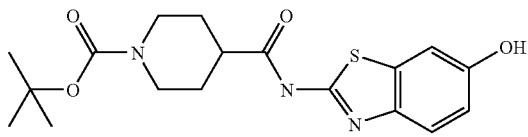

A solution of piperidine-1,4-dicarboxylic acid mono-tert-butyl ester (276 mg, 1.203 mmol), of HATU (549 mg, 1.444 mmol) and of diisopropylethylamine (187 mg, 1.44 mmol) in 3 ml of DMF is stirred at room temperature for 15 minutes. The 2-aminobenzothiazol-6-ol (intermediate 1) (200 mg, 1.203 mmol) dissolved in 3 ml of DMF is added in a single portion. The reaction medium is stirred at room temperature for 2 hours, poured into a 10% solution of Na₂CO₃ in water (20 ml) and extracted with ethyl acetate. The crude reaction product is purified by column chromatography (eluent: EtOAc/heptane (1/1)) to give 401 mg of 4-(6-hydroxybenzothiazol-2-ylcarbamoyl)-piperidine-1-carboxylic acid tert-butyl ester (white solid).

LC/MS (method A2): [M+H]+=378.0, retention time: 3.9 minutes.

INTERMEDIATE 3

Preparation of 4-[6-(4-fluorobenzenesulfonyloxy)benzothiazol-2-ylcarbamoyl]piperidine-1-carboxylic acid tert-butyl ester

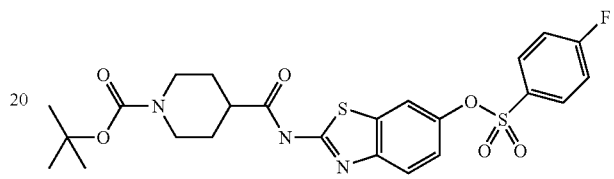

A solution of 4-(6-hydroxybenzothiazol-2-ylcarbamoyl)piperidine-1-carboxylic acid tert-butyl ester (intermediate 2) (454 mg, 1.20 mmol), of 4-fluoro-benzenesulfonyl chloride (234 mg, 1.20 mmol) and of triethylamine (320 μl) in 10 ml of acetone is stirred at room temperature for 1 hour. The triethylamine hydrochloride is filtered off and the filtrate is evaporated. The crude reaction product is purified by column chromatography (eluent: EtOAc/heptane (7/3)) to give 400 mg of 4-fluorobenzenesulfonic 2-[(piperidine-4-carbonyl)amino]-benzothiazol-6-yl ester (white solid).

LC/MS (method A2): [M+H]+=535.9, retention time: 4.9 minutes.

INTERMEDIATE 4

Preparation of 4-fluorobenzenesulfonic 2-[(piperidine-4-carbonyl)amino]benzothiazol-6-yl ester

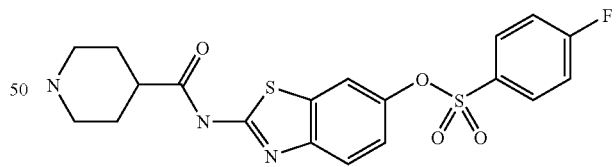

A solution of 4-[6-(4-fluorobenzenesulfonyloxy)benzothiazol-2-ylcarbamoyl]-piperidine-1-carboxylic acid tert-butyl ester (intermediate 3) (100 mg, 0.187 mmol) and of TFA (0.5 ml) in dichloromethane (4.5 ml) is stirred at room temperature for 1 hour. The reaction medium is evaporated to dryness. The residue is taken up in a minimum amount of water, neutralized by addition of aqueous 10% Na₂CO₃ solution and extracted with ethyl acetate to give 55 mg of 4-fluorobenzenesulfonic 2-[(piperidine-4-carbonyl)amino]benzothiazol-6-yl ester (white solid).

LC/MS (method A2): [M+H]+=435.9, retention time: 3.0 minutes.

EXAMPLE 5

Preparation of 4-(2-hydroxy-2-methylpropylamino) benzene-sulfonic acid 2-[(piperidine-4-carbonyl) amino]benzothiazol-6-yl ester

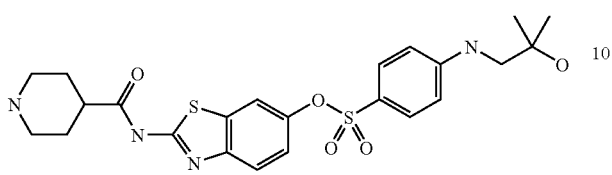

A solution of 4-fluorobenzenesulfonic 2-[(piperidine-4-carbonyl)amino]benzo-thiazol-6-yl ester (intermediate 4) (50 mg, 0.114 mmol) and of 4-(4-pyrid-3-yl-imidazol-1-yl) butylamine (40.93 mg, 0.459 mmol) in 0.5 ml of NMP is heated at 130° C. by microwave for 5 minutes. The crude reaction product is purified by preparative LC/MS (basic medium (pH 9)) to give after freeze-drying 21 mg of 4-(2-hydroxy-2-methylpropylamino)benzenesulfonic 2-(cyclo-propanecarbonylamino)benzothiazol-6-yl ester (pale yellow solid).

LC/MS (method A2): [M+H]+=505.2, retention time: 2.70 minutes.

INTERMEDIATE 6

Preparation of cyclopropanecarboxylic acid (6-hydroxybenzo-thiazol-2-yl)amide

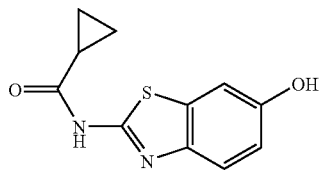

A solution of 2-aminobenzothiazol-6-ol (intermediate 1) (850 mg, 4.6 mmol), cyclopropanecarboxylic acid (1.564 g, 18.1 mmol), N,N-diisopropylethylamine (3.6 ml, 24.4 mmol) and HBTU (4.1 g, 5.53 mmol) in 40 ml of dimethyl-formamide, in a 100 ml round-bottomed flask equipped with a magnetic bar, is stirred at room temperature for 16 hours. 150 ml of water are added to the reaction medium, the mixture is extracted with ethyl acetate and the extracts are washed with saturated sodium chloride solution, dried over magnesium sulfate and concentrated to dryness. The residue obtained is washed with ethyl acetate to give 893 mg of cyclopropanecarboxylic acid 2-(cyclo-propanecarbonylamino)benzothiazol-6-yl ester. LC/MS: [M+H]+=303.18, retention time=3.53 min. A solution of lithium hydroxide monohydrate (200 mg, 4.768 mmol) in 50 ml of methanol and 5 ml of water is added to this product. The reaction medium is refluxed with stirring for 1 hour. The reaction medium is concentrated, acidified to pH 1 with 2N hydrochloric acid solution, diluted with 100 ml of water and extracted with ethyl acetate. The organic phase is washed with water and then with saturated sodium chloride solution and evaporated to dryness to give 500 mg of cyclo-propanecarboxylic acid (6-hydroxybenzothiazol-2-yl)amide in a yield of 72% (beige-colored powder).

NMR: 1H NMR spectrum (400 MHz)—δ in ppm—in DMSO-d6: from 0.90 to 1.00 (unresolved complex, 4H); 1.98 (unresolved complex, 1H); 6.88 (dd, J=8.5 and 3.0 Hz, 1H); 7.27 (d, J=3.0 Hz, 1H); 7.54 (d, J=8.5 Hz, 1H); 9.51 (broad s, 1H); 12.4 (broad s, 1H).

EXAMPLE 7

Preparation of 4-fluorobenzenesulfonic acid 2-(cyclopropane-carbonylamino)benzothiazol-6-yl ester

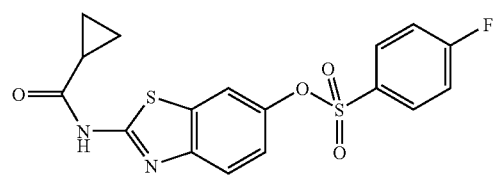

A solution of cyclopropanecarboxylic acid (6-hydroxy-benzothiazol-2-yl)amide (intermediate 6) (1.81 g, 7.72 mmol), 4-fluorobenzenesulfonyl chloride (1.5 g, 7.72 mmol) and triethylamine (2.14 ml, 15.45 mmol) in 43 ml of acetone, in a 100 ml round-bottomed flask equipped with a magnetic bar, is stirred for 1 hour at room temperature. The precipitate obtained is filtered off and the filtrate is evaporated. The residue is washed with acetone and ethyl ether, to give 1.92 g of 4-fluorobenzenesulfonic acid 2-(cyclopropanecarbony-lamino)-benzothiazol-6-yl ester (off-white powder) in a yield of 66%.

Mass: IE: m/z 392 [M+−], m/z 324: [M+−.]-COC$_3$H$_5$, m/z 233: [M+−]-SO$_2$PhF, m/z 165: 324-SO$_2$PhF, m/z 69 (base peak): [COC$_3$H$_5$]+. 1H NMR spectrum (300 MHz)—δ in ppm—in DMSO-d6: from 0.92 to 1.03 (unresolved complex, 4H); 2.02 (unresolved complex, 1H); 7.04 (dd, J=8.5 and 2.5 Hz, 1H); 7.54 (unresolved complex, 2H); 7.70 (d, J=8.5 Hz, 1H); 7.80 (d, J=2.5 Hz, 1H); 7.97 (unresolved complex, 2H); 12.75 (broad s, 1H).

EXAMPLE 8

Preparation of 4-cyclopentylaminobenzenesulfonic 2-(cyclo-propanecarbonylamino)benzothiazol-6-yl ester

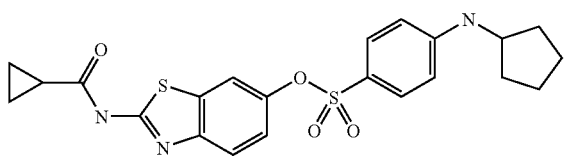

A solution of 4-fluorobenzenesulfonic 2-(cyclopropan-ecarbonylamino)benzo-thiazol-6-yl ester (example 7) (50 mg, 127.4 µmol) and cyclopentylamine (51 µl, 0.51 mmol) in 0.5 ml of NMP is heated at 150° C. by microwave for 5 minutes. The crude reaction product is purified by preparative LC/MS (basic medium (pH 9)) to give after freeze-drying 38 mg of 4-cyclopentylamino-benzenesulfonic 2-(cyclopropan-ecarbonylamino)benzothiazol-6-yl ester (white solid).

LC/MS (method A2): [M+H]+=458.0, retention time: 4.39 minutes.

EXAMPLE 9

Preparation of 4-(3-imidazol-1-ylpropylamino)benzenesulfonic 2-(cyclopropanecarbonylamino)benzothiazol-6-yl ester

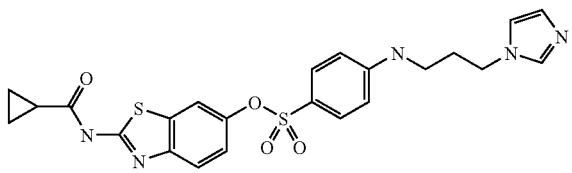

A solution of 4-fluorobenzenesulfonic 2-(cyclopropanecarbonylamino)benzo-thiazol-6-yl ester (example 7) (100 mg, 0.255 mmol) and 3-imidazol-1-yl-propylamine (123 µl, 1.019 mmol) in 2 ml of NMP is heated at 150° C. by microwave for 5 minutes. The crude reaction product is purified by preparative LC/MS (basic medium (pH 9)) to give after freeze-drying 63 mg of 4-(3-imidazol-1-ylpropylamino)benzenesulfonic 2-(cyclopropanecarbonylamino)benzothiazol-6-yl ester (white solid).

LC/MS (method A2): [M+H]+=

EXAMPLE 10

Preparation of 4-methylaminobenzenesulfonic 2-(cyclopropane-carbonylamino)benzothiazol-6-yl ester

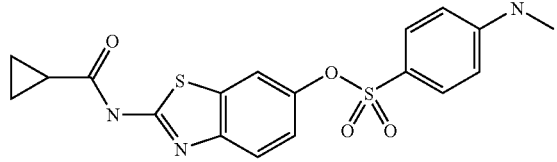

A solution of 4-fluorobenzenesulfonic 2-(cyclopropanecarbonylamino)benzo-thiazol-6-yl ester (example 7) (25 mg, 63.71 µmol) and methylamine (2N in MeOH, 200 µl) in 300 µl of NMP is heated at 150° C. by microwave for 3 minutes. The crude reaction product is purified by preparative LC/MS (basic medium (pH 9)) to give after freeze-drying 6.7 mg of 4-methylaminobenzene-sulfonic 2-(cyclopropanecarbonylamino)benzothiazol-6-yl ester (beige-colored solid).

LC/MS (method A2): [M+H]+=404.1, retention time: 3.83 minutes.

EXAMPLE 11

Preparation of 4-(2-hydroxy-2-methylpropylamino)benzene-sulfonic 2-(cyclopropanecarbonylamino)benzothiazol-6-yl ester

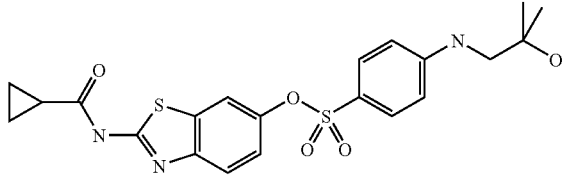

A solution of 4-fluorobenzenesulfonic 2-(cyclopropanecarbonylamino)benzo-thiazol-6-yl ester (example 7) (100 mg, 255 µmol) and 1-amino-2-methyl-propan-2-ol (91 mg, 1.02 mmol) in 2 ml of NMP is heated at 150° C. by microwave for 5 minutes. The crude reaction product is purified by preparative LC/MS (basic medium (pH 9)) to give after freeze-drying 61 mg of 4-(2-hydroxy-2-methylpropylamino)benzenesulfonic 2-(cyclopropanecarbonyl-amino)benzothiazol-6-yl ester (beige-colored solid).

LC/MS (method A2): [M+H]+=462.1, retention time: 3.83 minutes.

EXAMPLE 12

Preparation of 4-(2-diisopropylaminoethylamino)benzenesulfonic 2-(cyclopropanecarbonylamino)benzothiazol-6-yl ester

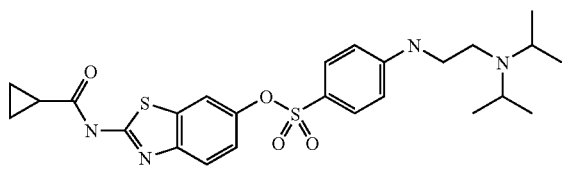

A solution of 4-fluorobenzenesulfonic 2-(cyclopropanecarbonylamino)benzo-thiazol-6-yl ester (example 7) (100 mg, 255 µmol) and N,N-diisopropyl-ethane-1,2-diamine (147 mg, 1.02 mmol) in 2 ml of NMP is heated at 110° C. by microwave for 10 minutes. The crude reaction product is purified by preparative LC/MS (basic medium (pH 9)) to give after freeze-drying 66 mg of 4-(2-hydroxy-2-methylpropylamino)benzenesulfonic 2-(cyclopropanecarbonyl-amino)benzothiazol-6-yl ester (beige-colored solid).

LC/MS (method A2): [M+H]+=517.1, retention time: 2.93 minutes.

EXAMPLE 13

Preparation of 4-[4-(4-pyrid-3-ylimidazol-1-yl)butylamino]-benzenesulfonic 2-(cyclopropanecarbonylamino)benzothiazol-6-yl ester

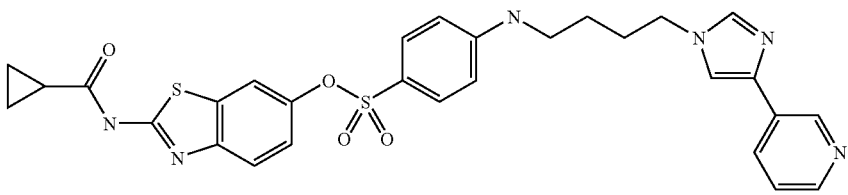

A solution of 4-fluorobenzenesulfonic 2-(cyclopropanecarbonylamino)benzo-thiazol-6-yl ester (example 7) (50 mg, 127.4 µmol) and 4-(4-pyrid-3-ylimidazol-1-yl)butylamine (110.2 mg, 0.51 mmol) in 0.5 ml of NMP is heated at 150° C. by microwave for 8 minutes. The crude reaction product is purified by preparative LC/MS (basic medium (pH 9)) to give after freeze-drying 36 mg of 4-(2-hydroxy-2-methylpropylamino)benzenesulfonic 2-(cyclo-propanecarbonylamino)benzothiazol-6-yl ester (beige-colored solid).

LC/MS (method A2): [M+H]+=589.0, retention time: 3.14 minutes.

INTERMEDIATE 14

Preparation of (6-hydroxybenzothiazol-2-yl)carbamic acid tert-butyl ester

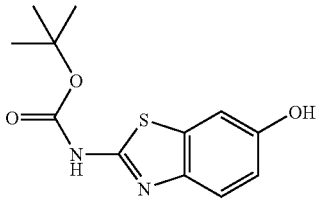

A solution of 2-aminobenzothiazol-6-ol (intermediate 1) (1.91 g, 11.49 mmol), di-tert-butyl dicarbonate (7.52 g, 34.47 mmol), triethylamine (4.9 ml, 34.47 mmol) and 4-dimethylaminopyridine (168 mg, 1.38 mmol) in 50 ml of dichloromethane, in a 100 ml round-bottomed flask equipped with a magnetic bar, is stirred overnight at room temperature. The reaction medium is evaporated to dryness and the residue obtained is washed with dichloromethane and ethyl ether to give 4.2 g of carbonic acid 2-tert-butoxy-carbonylaminobenzothiazol-6-yl ester tert-butyl ester in quantitative yield.

LC/MS: [M+H]+:311.16, retention time: 5.27 min.

A solution of sodium hydroxide (920 mg, 22.8 mmol) in 110 ml of methanol is added to this product. The reaction medium is stirred for 2 hours at room temperature by ultrasonication and then acidified to pH 4 with 2N hydrochloric acid solution.

The reaction medium is evaporated to dryness and the residue obtained is washed with dichloromethane and ethyl ether to give 2.35 g of (6-hydroxy-benzothiazol-2-yl)carbamic acid tert-butyl ester (beige-colored powder) in a yield of 77%.

Mass: IE: m/z 266 [M+−], m/z 166 (base peak): [M+−]—CO₂tBu

IR:KBr

3422; 3263; 3091; 2981; 1725; 1608; 1562; 1468; 1278; 1245; 1154; 1049; 862 and 852 cm⁻¹

1H NMR spectrum (300 MHz)—δ in ppm—in DMSO-d6: 1.52 (s, 9H); 6.85 (dd, J=9.0 and 3.0 Hz, 1H); 7.24 (d, J=3.0 Hz, 1H); 7.49 (d, J=9.0 Hz, 1H); 9.44 (broad unresolved complex, 1H); 11.5 (broad unresolved complex, 1H).

INTERMEDIATE 15

Preparation of 4-fluorobenzenesulfonic acid 2-tert-butoxy-carbonylaminobenzothiazol-6-yl ester

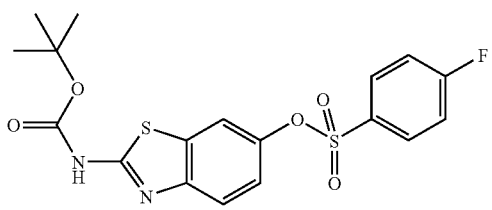

A solution of (6-hydroxybenzothiazol-2-yl)carbamic acid tert-butyl ester (intermediate 14) (3.61 g, 13.08 mmol), 4-fluorobenzenesulfonyl chloride (2.56 g, 13.08 mmol) and triethylamine (3.63 ml, 26.16 mmol) in 65 ml of acetone, in a 100 ml round-bottomed flask equipped with a magnetic bar, is stirred overnight at room temperature. The precipitate obtained is filtered off and the filtrate is evaporated to dryness. The dry residue is washed with ethyl acetate to give 5.02 g of 4-fluorobenzenesulfonic acid 2-tert-butoxycarbonyl-aminobenzothiazol-6-yl ester (white powder) in a yield of 62%.

1H NMR spectrum (400 MHz)—δ in ppm—in DMSO-d6: 1.53 (s, 9H); 7.02 (dd, J=9.0 and 2.5 Hz, 1H); 7.55 (t, J=9.0 Hz, 2H); 7.65 (d, J=9.0 Hz, 1H); 7.78 (d, J=2.5 Hz, 1H); 7.98 (dd, J=5.0 and 9.0 Hz, 2H); 11.9 (broad s, 1H).

INTERMEDIATE 16

Preparation of 4-fluorobenzenesulfonic acid 2-aminobenzo-thiazol-6-yl ester

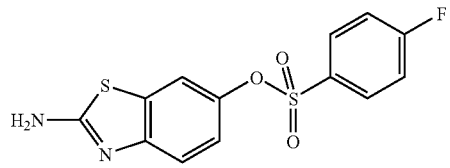

A solution of 4-fluorobenzenesulfonic acid 2-tert-butoxycarbonylaminobenzo-thiazol-6-yl ester (intermediate 15) (1.7 g, 3.60 mmol), 10 ml of trifluoroacetic acid (130 mmol) in 10 ml of dichloromethane, and 1 ml of water, in a 100 ml round-bottomed flask equipped with a magnetic bar, is stirred for 2 hours at room temperature. The reaction medium is evaporated to dryness and the residue obtained is washed with ethyl ether to give 1.31 g of 4-fluoro-benzenesulfonic acid 2-aminobenzothiazol-6-yl ester in the form of the trifluoroacetic acid salt (white powder) in a yield of 83%.

LC/MS (method A1): [M+H]+:325.13, retention time: 3.12 min.

INTERMEDIATE 17

Preparation of 4-{[6-(4-fluorobenzenesulfonyloxy)benzo-thiazol-2-ylcarbamoyl]methyl}piperidine-1-carboxylic acid tert-butyl ester

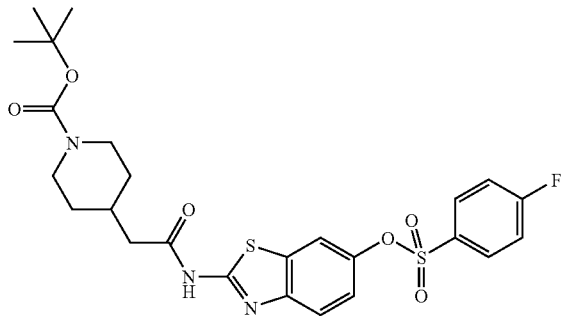

A solution of 4-fluorobenzenesulfonic acid 2-aminobenzothiazol-6-yl ester (intermediate 16) (580 mg, 1.32 mmol), 4-carboxymethylpiperidine-1-car-boxylic acid tert-butyl ester (640 mg, 2.63 mmol), HBTU (1.1 g, 2.9 mmol), and N,N-diisopropylamine (1.2 ml, 6.89 mmol) in 12 ml of dimethylformamide, in a test tube equipped with a magnetic bar, is stirred for 3 days at room temperature. 200 ml of water are added to the reaction medium and the mixture is extracted with ethyl acetate. The organic phase is then washed with water and with saturated sodium chloride solution, and then dried over magnesium sulfate and evaporated. The residue obtained is taken up in ethyl acetate and purified on a Varian flash cartridge containing 50 g of silica of porosity 15-35μ, with a gradient of from 5% to 30% of ethyl acetate in cyclohexane, over 100 minutes. After evaporating off the solvent, 700 mg of 4-{[6-(4-fluorobenzenesulfonyloxy)benzothiazol-2-ylcarbamoyl]methyl}piperidine-1-carboxylic acid tert-butyl ester are obtained (yellow oil) in a yield of 96%.

LC/MS (method A1): [M+H]+:550.11, retention time: 4.14 min.

EXAMPLE 18

Preparation of 4-(2-isopropylaminoethylamino)benzenesulfonic acid 2-(2-piperid-4-ylacetylamino)benzothiazol-6-yl ester hydrochloride

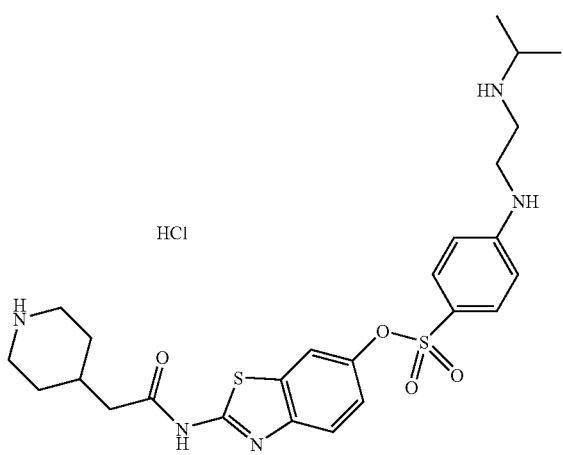

1st step: A solution of 4-{[6-(4-fluorobenzenesulfonyloxy)benzothiazol-2-yl-carbamoyl]methyl}piperidine-1-carboxylic acid tert-butyl ester (intermediate is 17) (174 mg, 0.318 mmol), N-isopropylethylenediamine (97 mg, 0.954 mmol) and cesium carbonate (103 mg, 0.318 mmol) in 3 ml of dimethyl sulfoxide, in a test tube equipped with a magnetic bar, is stirred overnight at 90° C. 100 ml of water are added to the reaction medium and the mixture is extracted with ethyl acetate. The organic phase is then washed with water and with saturated sodium chloride solution, and then dried over magnesium sulfate and evaporated to give 103 mg of 4-({6-[4-(3-imidazol-1-ylpropylamino)-benzenesulfonyloxy]benzothiazol-2-ylcarbamoyl}methyl)piperidine-1-carboxylic acid tert-butyl ester (white powder) in a yield of 50%.

2nd step: A solution of 103 mg of 4-({6-[4-(3-imidazol-1-ylpropylamino)-benzenesulfonyloxy]benzothiazol-2-ylcarbamoyl}methyl)piperidine-1-carboxylic acid tert-butyl ester, 2 ml of dioxane and 2 ml of 4N hydrochloric acid in dioxane is stirred for 3 hours at room temperature. The precipitate obtained is filtered off and washed with dioxane and ethyl ether to give 110 mg of 4-(2-isopropylaminoethylamino)benzenesulfonic acid 2-(2-piperid-4-ylacetylamino)benzothiazol-6-yl ester hydrochloride (white powder) in a yield of 88%.

Mass: LCMS: m/z 532 [M+H]+, m/z 407 (base peak): [M+H]+—$C_5H_{10}NCH_2CO$

IR:KBr

3432; 2960; 2793; 2464; 2598; 1560; 1470; 1364; 1162; 1120; 1093; 915; 853 and 753 cm$^{-1}$ 1H NMR spectrum (400 MHz)—δ in ppm—in DMSO-d6: 1.28 (d, J=7.0 Hz, 6H); 1.48 (m, 2H); 1.83 (broad d, J=12.5 Hz, 2H); 2.12 (unresolved complex, 1H); 2.52 (masked, 2H); 2.92 (m, 2H); 3.10 (unresolved complex, 2H); 3.28 (broad d, J=12.5 Hz, 2H); 3.36 (mt, J=7.0 Hz, 1H); 3.50 (t, J=6.0 Hz, 2H); 6.78 (broad d, J=9.0 Hz, 2H); 7.03 (dd, J=8.5 and 2.5 Hz, 1H); 7.30 (broad unresolved complex, 1H); 7.56 (broad d, J=9.0 Hz, 2H); 7.71 (d, J=8.5 Hz, 1H); 7.78 (d, J=2.5 Hz, 1H); 8.58 (broad unresolved complex, 1H); 8.81 (broad unresolved complex, 1H); 9.00 (broad unresolved complex, 2H); 12.5 (broad s, 1H).

EXAMPLE 19

Using the same method as in example 18, the following examples are prepared using 4-{[6-(4-fluorobenzenesulfonyloxy)benzothiazol-2-ylcarbamoyl]methyl}piperidine-1-carboxylic acid tert-butyl ester as precursor (intermediate 17) combined with various amines. In the following examples, the compound obtained after the first step is purified on a flash cartridge of 5 g of Interchim silica (15-35μ), with a gradient of from 5% to 10% methanol in dichloromethane, with a flow rate of 10 ml/minute. These examples are given in the following table:

| Example No. | amine | compound | characterization |
|---|---|---|---|
| 19 a | 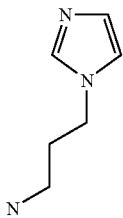 | 4-(3-Imidazol-1-ylpropyl-amino)benzenesulfonic acid 2-(2-piperid-4-ylacetyl-amino)benzothiazol-6-yl ester hydrochloride; | IR: KBr 3426; 2957; 2717; 2462; 1597; 1545; 1451; 1364; 1199; 1161; 1092; 872; 750 and 586 $cm^{-1}$<br>Mass: LCMS: m/z 555 $[M + H]^+$, m/z 430 (base peak): $[M + H]^+ - C_5H_{10}NCH_2CO$<br>1H NMR spectrum (400 MHz) - δ 6 in ppm - in DMSO-d6:<br>1.48(m, 2H); 1.84(broad d, J=12.5Hz, 2H); 2.12(unresolved complex, 3H); 2.52 (masked, 2H); 2.91(m, 2H); 3.13(t, J=6.5 Hz, 2H); 2.28(broad d, J=12.5Hz, 2H); 4.33(t, J=6.5Hz, 2H); 6.70(broad d, J=9.0Hz, 2H); 7.02(dd, J=9.0 and 3.0 Hz, 1H); 7.20(very broad unresolved complex, 1H); 7.51(broad d, J=9.0Hz, 2H); 7.71(d, J=9.0Hz, 1H); 7.73(broad s, 1H); 7.78(d, J=3.0Hz, 1H); 7.87(broad s, 1H); 8.70(broad unresolved complex, 1H); 8.91(broad unresolved complex, 1H); 9.24 (broad s, 1H) ; 12.5(broad s, 1H); 14, 55 (very broad unresolved complex, 1H). |
| 19 b | 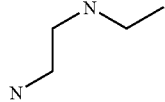 | 4-(2-Ethylaminoethyl-amino)benzenesulfonic acid 2-(2-piperid-4-ylacetyl-amino)benzothiazol-6-yl ester hydrochloride | IR: KBr 3425; 2956; 2717; 2462; 1597; 1558; 1469; 1364; 1162; 1119; 1094; 872; 744 and 584 $cm^{-1}$<br>Mass: LCMS: m/z 518 $[M + H]^+$, m/z 393 (base peak): $[M + H]^+ - C_5H_{10}NCH_2CO$<br>1H NMR spectrum (400 MHz) - δ in ppm - in DMSO-d6:<br>1.25(t, J=7.0Hz, 3H); 1.47(m, 2H); 1.85 (broad d, J=12.5Hz, 2H); 2.12 (unresolved complex, 1H); 2.52(masked, 2H); 2.91(m, 2H); 3.02(q, J=7.0Hz, 2H); 3.10(unresolved complex, 2H); 3.28(d, J=12.5Hz, 2H); 3.48(t, J=6.0Hz, 2H); 6.78(broad d, J=9.0Hz, 2H); 7.02(dd, J=8.5 and 2.5Hz, 1H); 7.30(very broad unresolved complex, 1H); 7.45(broad d, J=9.0Hz, 2H); 7.71(d, J=8.5Hz, 1H); 7.78(d, J=2.5Hz, 1H); 8.62(broad unresolved complex, 1H); 8.86(broad unresolved complex, 1H); 9.04(unresolved complex, 2H); 12.45(broad s, 1H). |

-continued

| Example No. | amine | compound | characterization |
|---|---|---|---|
| 19 c | (structure: HOCH₂CH₂-N(CH₂CH₂-)CH₂CH₂-N-piperidine) | 4-[2-(2-Hydroxyethyl-amino)ethylamino]benzene-sulfonic acid 2-(2-piperid-4-ylacetylamino)benzo-thiazol-6-yl ester hydrochloride | IR: KBr 3435; 2949; 2790; 2462; 1598; 1561; 1470; 1363; 1161; 1093; 854; 751 and 590 cm$^{-1}$ Mass: LCMS: m/z 534 [M + H]$^+$, m/z 409 (base peak): [M + H]$^+$ − C$_5$H$_{10}$NCH$_2$CO 1H NMR spectrum (400 MHz) - δ in ppm - in DMSO-d6: 1.46(m, 2H); 1.85(broad d, J=12.5Hz, 2H); 2.12(unresolved complex, 1H); 2.52 (masked, 2H); 2.92(m, 2H); 3.08 (unresolved complex, 2H); 3.13(unresolved complex, 2H); 3.28(broad d, J=12.5Hz, 2H); 3.45(masked, 2H); 3.71(t, J=5.5Hz, 2H); 6.77(broad d, J=9.0Hz, 2H); 7.03 (dd, J=8.5 and 2.5Hz, 1H); 7.18(broad unresolved complex, 1H); 7.55(broad d, J=9.0Hz, 2H); 7.72(d, J=8.5Hz, 1H); 7.79(d, J=2.5Hz, 1H); 8.51(broad unresolved complex, 1H); 8.75(broad unresolved complex, 1H); 8.87(broad unresolved complex, 2H); 12.5(broad s, 1H). |
| 19 d | (structure: (CH₃)₂C(OH)CH₂NH-) | 4-(2-Hydroxy-2-methyl-propylamino)benzene-sulfonic acid 2-(2-piperid-4-ylacetylamino)benzo-thiazol-6-yl ester hydrochloride | LCMS: [M + H]$^+$ = 519.08, retention time: 2.66 min IR: KBr 3415; 2971; 1597; 1563; 1470; 1365; 1161; 1094; 915; 854; 746 and 586 cm$^{-1}$ 1H NMR spectrum (400 MHz) - δ in ppm - DMSO-d6: 1.18(s, 6H); 1.45(m, 2H); 1.85(broad d, J=12.5Hz, 2H); 2.13(unresolved complex, 1H); 2.52(masked, 2H); 2.92(m, 2H); 3.06(s, 2H); 3.28(broad d, J=12.5 Hz, 2H); 6.78(broad d, J=9.0Hz, 2H); from 6.50 to 7.00(broad unresolved complex, 1H); 7.02(dd, J=9.0 and 2.5Hz, 1H); 7.45(broad d, J=9.0Hz, 2H); 7.70(d, J=9.0Hz, 1H); 7.75(d, J=2.5Hz, 1H); 8.51(broad unresolved complex, 1H); 8.78 (broad unresolved complex, 1H); 12.5 (broad s, 1H). |

45

INTERMEDIATE 20

Preparation of 4-fluorobenzenesulfonic acid 2-(8-tert-butoxy-carbonylaminooctanoylamino)benzothiazol-6-yl ester

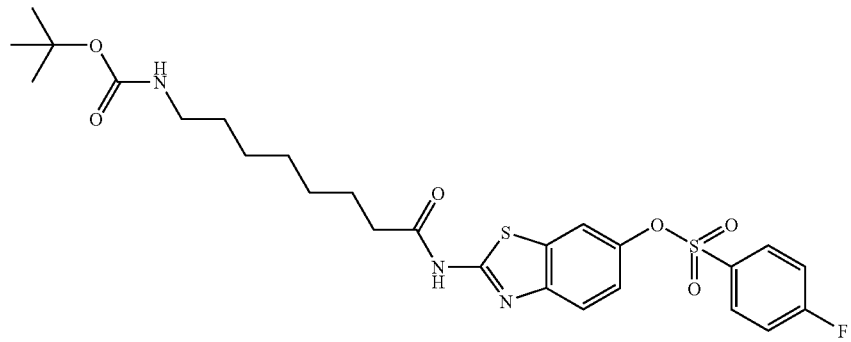

According to the method of intermediate 17, 4-fluorobenzenesulfonic acid 2-(8-tert-butoxycarbonylaminooctanoylamino)benzothiazol-6-yl ester is pre-pared by combining 4-fluorobenzenesulfonic acid 2-aminobenzothiazol-6-yl ester (intermediate 16) with Boc-8-aminocaprylic acid.

LC/MS (method A1): [M+H]+:566.01, retention time: 4.21 min.

EXAMPLE 21

Preparation of 4-(2-isopropylaminoethylamino)benzenesulfonic acid 2-(8-aminooctanoylamino)benzothiazol-6-yl ester hydrochloride Mass: EI: m/z 406: [M$^{+-}$]—C$_8$H$_{16}$O, m/z 335: [M$^{+-}$]—C$_4$H$_{10}$N, m/z 72 C$_4$H$_{10}$N (base peak).

Cl: m/z 548 [M+H]$^+$ (base peak), m/z 407: [M+H]$^+$—C$_8$H$_{16}$NO IR:KBr

3426; 2923; 2448; 1717; 1597; 1563; 1472; 1371; 1165; 1092; 911; 857; 755; 574 and 548 cm$^{-1}$ 1H NMR spectrum (400 MHz)—δ in ppm—in DMSO-d6: 1.30 (t, J=7.0 Hz, 6H); 1.33 (unresolved complex, 6H); 1.58 (unresolved complex, 2H); 1.67 (unresolved complex, 2H); 2.52 (masked, 2H); 2.79 (unresolved complex, 2H); 3.01 (unresolved complex, 2H); 3.36 (mt, J=7.0 Hz, 1H); 3.48 (unresolved complex, 2H); 6.78 (broad d, J=9.0 Hz, 2H); 7.02 (dd, J=8.5 and 2.5 Hz, 1H); 7.30 (unresolved complex, 1H); 7.56 (broad d, J=9.0 Hz, 2H); 7.70 (d, J=8.5 Hz, 1H); 7.77 (d,

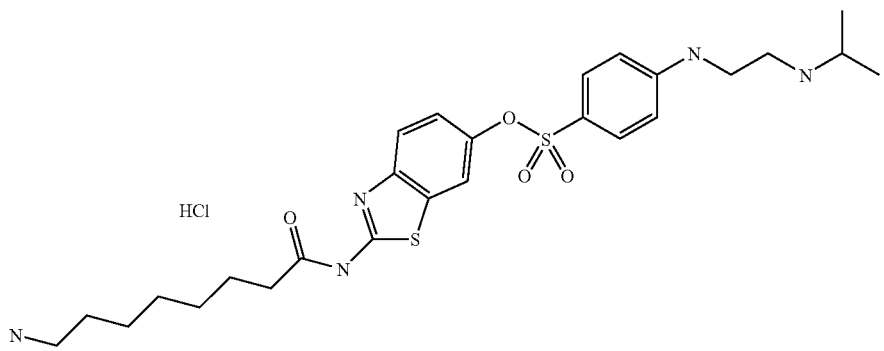

According to the method of example 18, 4-(2-isopropylaminoethylamino)-benzenesulfonic acid 2-(8-aminooctanoylamino)benzothiazol-6-yl ester hydro-chloride is pre-pared by combining 4-fluorobenzenesulfonic acid 2-(8-tert-butoxycarbonylaminooctanoylamino)benzothiazol-6-yl ester (intermediate 20) with N-isopropylethylenediamine. The compound obtained from the first step, (4-(2-isopropylaminoethylamino)benzenesulfonic acid 2-(8-tert-butoxycarbonylaminooctanoylamino)benzothiazol-6-yl ester, is purified on silica with a gradient of from 4% to 15% of methanol in dichloromethane.

J=2.5 Hz, 1H); 7.82 (broad unresolved complex, 3H); 9.00 (broad unresolved complex, 2H); 12.45 (broad s, 1H).

EXAMPLE 22

Using the same method as in example 21, the following examples are prepared using 4-fluorobenzenesulfonic acid 2-(8-tert-butoxy-carbonylaminooctanoylamino)benzothiazol-6-yl ester (intermediate 20) as precursor combined with various amines. These examples are presented in the following table:

| Example No. | amine | compound | characterization |
|---|---|---|---|
| 22 a | ![imidazolylpropylamine structure] | 4-(3-imidazol-1-ylpropylamino)benzenesulfonic acid 2-(8-aminooctanoylamino)-benzothiazol-6-yl ester hydrochloride | 1H NMR spectrum (300 MHz) - δ in ppm - in DMSO-d6:<br>1.31(unresolved complex, 6H); from 1.49 to 1.68 (unresolved complex, 4H); 2.11(mt, J=7.0Hz, 2H); 2.52(masked, 2H); 2.75 (unresolved complex, 2H); 3.11(t, J=7.0Hz, 2H); 4.32(t, J=7.0Hz, 2H); 6.68(broad d, J=9.0Hz, 2H); 6.97(dd, J=9.0 and 2.5Hz, 1H); 7.20(very broad unresolved complex, 1H); 7.50(broad d, J=9.0Hz, 2H); 7.67(d, J=9.0Hz, 1H); 7.72(t, J=2Hz, 1H); 7.74(d, J=2.5Hz, 1H); 7.85(t, J=2Hz, 1H); 7.89 (broad unresolved complex, 3H); 9.24(t, J=2Hz, 1H); 12.45(broad s, 1H); 14.6(broad unresolved complex, 1H). |

| Example No. | amine | compound | characterization |
|---|---|---|---|
| 22 b | (ethylaminoethylamino structure) | 4-(2-ethylaminoethyl-amino)benzene sulfonic acid 2-(8-aminooctanoyl-amino)benzothiazol-6-yl ester | IR: KBr 3421; 2931; 2457; 1717; 1596; 1563; 1472; 1370; 1357; 1199; 1163; 1093; 911; 857; 756; 677; 611; 574 and 547 cm$^{-1}$ Mass: CI: m/z 534 [M + H]$^+$ (base peak). 1H NMR spectrum (400 MHZ) - δ in ppm - in DMSO-d6: 1.22(t, J=7.0Hz, 3H); 1.32(unresolved complex, 6H); 1.56(unresolved complex, 2H); 1.64(unresolved complex, 2H); 2.52(masked, 2H); 2.79(unresolved complex, 2H); 3.01 (unresolved complex, 2H); 3.10(unresolved complex, 2H); 3.45(unresolved complex, 2H); 6.73(broad d, J=9.0Hz, 2H); 7.02(dd, J=8.5 and 3.0Hz, 1H); 7.22(broad unresolved complex, 1H); 7.55(broad d, J=9.0Hz, 2H); 7.67(d, J=8.5Hz, 1H); 7.78 (d, J=3.0Hz, 1H); 7.82(broad unresolved complex, 3H); 8.92(broad unresolved complex, 2H), 12.4(broad s, 1H). |
| 22 c | (hydroxyethylamino ethylamino structure) | 4-[2-(2-hydroxyethyl-amino)ethylamino]benzene-sulfonic acid 2-(8-amino-octanoylamino)benzo-thiazol-6-yl ester hydro-chloride | IR: KBr 3444; 2926; 2627; 2416; 1715; 1597; 1563; 1473; 1370; 1196; 1165; 1148; 1092; 911; 858; 849; 757; 612; 574 and 549 cm$^{-1}$ Mass: CI: m/z 550 [M + H]$^+$, m/z 409: [M – CO(CH$_2$)$_7$NH$_2$ + H]H$^+$ (base peak). 1H NMR spectrum (300 MHz) - δ in ppm - in DMSO-d6: 1.28(unresolved complex, 6H); from 1.43 to 1.67(unresolved complex, 4H); 2.52(masked, 2H); 2.73(unresolved complex, 2H); from 3.00 to 3.15(unresolved complex, 4H); 3.45 (unresolved complex, 2H); 3.67(unresolved complex, 2H); 6.72(broad d, J=9.0Hz, 2H); 6.98(broad d, J=9.0Hz, 1H); 7.20(broad unresolved complex, 1H); 7.52(broad d, J=9.0Hz, 2H); 7.65(d, J=9.0Hz, 1H); 7.72 (broad, s, 1H); 7.82(broad unresolved complex, 3H); 8.92(broad unresolved complex, 2H); 12.4(broad s, 1H). |
| 22 d | (hydroxymethylpropylamino structure) | 4-(2-Hydroxy-2-methyl-propylamino)benzene-sulfonic acid 2-(8-amino-octanoylamino)benzo-thiazol-6-yl ester hydro-chloride | Mass: LCMS: m/z 535 [M + H]$^+$ (base peak), m/z 463: [M + H]$^+$ – C$_4$H$_9$O CI: m/z 535 [M + H]$^+$ (base peak). 1H NMR spectrum (300 MHz) - δ in ppm - in DMSO-d6: 1.14(s, 6H); 1.29(unresolved complex, 6H); 1.53(unresolved complex, 2H); 1.63 (unresolved complex, 2H); 2.52(masked, 2H); 2.75(unresolved complex, 2H); 3.03(s, 2H); 6.75(broad d, J=9.0Hz, 2H); 6.97(dd, J=9.0 and 2.5Hz, 1H); 7.42(broad d, J=9.0 Hz, 2H); 7.65(d, J=9.0Hz, 1H); 7.70(d, J=2.5Hz, 1H); 7.78(broad unresolved complex, 3H); 12.4(broad s, 1H). |

INTERMEDIATE 23
Preparation of 4-{2-[6-(4-fluorobenzenesulfonyloxy)benzo-thiazol-2-ylcarbamoyl]ethyl}piperidine-1-carboxylic acid tert-butyl ester

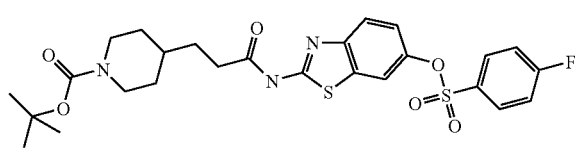

According to the method for intermediate 17, 4-{2-[6-(4-fluorobenzene-sulfonyloxy)benzothiazol-2-ylcarbamoyl]ethyl}piperidine-1-carboxylic acid tert-butyl ester is prepared by combining 4-fluorobenzenesulfonic acid 2-amino-benzothiazol-6-yl ester (intermediate 16) with N-Boc-4-piperidinepropionic acid. LC/MS (method A1): [M+H]+: 564.16, retention time: 4.24 min.

EXAMPLE 24

4-(2-Isopropylaminoethylamino)benzenesulfonic acid 2-(3-piperid-4-ylpropionylamino)benzothiazol-6-yl ester hydrochloride

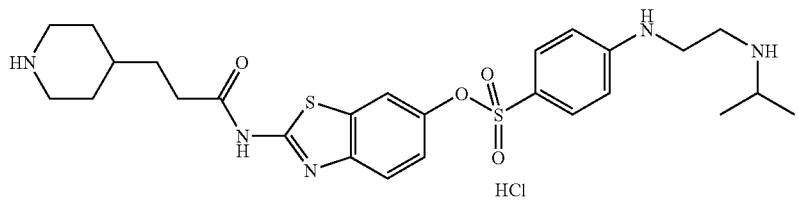

According to the method of example 18, 4-(2-isopropylaminoethylamino)-benzenesulfonic acid 2-(3-piperid-4-ylpropionylamino)benzothiazol-6-yl ester hydrochloride is prepared by combining 4-{2-[6-(4-fluorobenzenesulfonyloxy)-benzothiazol-2-ylcarbamoyl]ethyl}piperidine-1-carboxylic acid tert-butyl ester (intermediate 23) with N,N-diisopropylamine. The compound obtained from the first step (4-(2-{6-[4-(2-isopropylaminoethylamino)benzenesulfonyloxy]-benzothiazol-2-ylcarbamoyl}ethyl)piperidine-1-carboxylic acid tert-butyl ester) is purified on a flash cartridge of 5 g of silica of porosity 15-35μ, with a gradient of from 1% to 10% of methanol in dichloromethane.

Mass: LCMS: m/z 546 [M+H]$^+$, m/z 407: [M+H]$^+$—$C_5H_{10}NC_2H_4CO$, m/z 274: [M+2H]$^{2+}$ m/z 294 (base peak).

1H NMR spectrum (300 MHz)—δ in ppm—in DMSO-d6: 1.25 (d, J=7.0 Hz, 6H); 1.32 (m, 2H); from 1.45 to 1.65 (unresolved complex, 3H); 1.81 (broad d, J=12.5 Hz, 2H); 2.52 (masked, 2H); 2.82 (m, 2H); 3.07 (unresolved complex, 2H); 3.25 (broad d, J=12.5 Hz, 2H); 3.35 (masked, 1H); 3.45 (unresolved complex, 2H); 6.73 (broad d, J=9.0 Hz, 2H); 6.99 (dd, J=8.5 and 2.5 Hz, 1H); 7.20 (broad unresolved complex, 1H); 7.52 (broad d, J=9.0 Hz, 2H); 7.67 (d, J=8.5 Hz, 1H); 7.73 (d, J=2.5 Hz, 1H); 8.40 (broad unresolved complex, 1H); 8.65 (broad unresolved complex, 1H); 8.87 (broad unresolved complex, 2H); 12.4 (broad s, 1H).

EXAMPLE 25

Using the same method as in Example 24, the following examples are prepared using 4-{2-[6-(4-fluorobenzenesulfonyloxy)benzo-thiazol-2-ylcarbamoyl]ethyl}piperidine-1-carboxylic acid tert-butyl ester as precursor (intermediate 23) combined with various amines. These examples are presented in the following table:

| Example No. | amine | compound | characterization |
|---|---|---|---|
| 25 a | (imidazol-propyl-N structure) | 4-(3-Imidazol-1-ylpropylamino)benzenesulfonic acid 2-(3-piperid-4-ylpropionylamino)benzothiazol-6-yl ester hydrochloride | LCMS: m/z 569 [M + H]$^+$, m/z 430: [M + H]$^+$ – $C_5H_{10}NC_2H_4CO$ m/z 306(base peak) 1H NMR spectrum (300 MHz) - δ in ppm - in DMSO-d6: 1.32(m, 2H); from 1.45 to 1.65 (unresolved complex, 3H); 1.81 (broad d, J=12.5Hz, 2H); 2.10 (unresolved complex, 2H); 2.52 (masked, 2H); 2.82(m, 2H); 3.10 (unresolved complex, 2H); 3.23 (broad d, J=12.5Hz, 2H) ; 4.29(t, J=7.0Hz, 2H); 6.65(broad d, J=9.0Hz, 2H); 6.98(dd, J=8.5 and 2.5Hz, 1H); 7.10(broad unresolved complex, 1H); 7.48 (broad d, J=9.0Hz, 2H); 7.67(d, J=8.5Hz, 1H); 7.70(broad s, 1H); 7.72(d, J=2.5Hz, 1H); 7.81 (broad s, 1H); 8.45(broad unresolved complex, 1H); 8.72 (broad unresolved complex, 1H); 9.17(broad s, 1H); 12.4(broad s, 1H); 14, 4(broad unresolved complex, 1H). |

| Example No. | amine | compound | characterization |
|---|---|---|---|
| 25 b | (ethylaminoethylamine structure) | 4-(2-Ethylaminoethyl-amino)-benzenesulfonic acid 2-(3-piperid-4-yl-propionyl-amino)-benzothiazol-6-yl ester hydrochloride | LCMS: m/z 532 [M + H]$^+$, m/z 393: [M + H]$^+$ − $C_5H_{10}N(CH_2)_2CO$, m/z 267: [M + 2H]$^{2+}$, m/z 287(base peak).<br>1H NMR spectrum (300 MHz) - δ in ppm - in DMSO-d6: 1.21(t, J=6.5Hz, 3H); 1.30(m, 2H); from 1.45 to 1.65(unresolved complex, 3H); 1.80(broad d, J=12.5Hz, 2H); 2.52(masked, 2H); 2.83(m, 2H); 2.97(q, J=6.5 Hz, 2H); 3.07(unresolved complex, 2H); 3.25(broad d, J=12.5Hz, 2H); 3.44(unresolved complex, 2H); 6.73(d, large, J=9.0Hz, 2H); 6.99(dd, J=9.0 and 3.0Hz, 1H); 7.15(broad unresolved complex, 1H); 7.52(broad d, J=9.0Hz, 2H); 7.67(d, J=9.0Hz, 1H); 7.73(d, J=3.0Hz, 1H); 8.35(broad unresolved complex, 1H); 8.63 (broad unresolved complex, 1H); 8.81(broad unresolved complex, 2H); 12.4(broad s, 1H). |
| 25 c | (hydroxyethylaminoethylamine structure) | 4-[2-(2-Hydroxyethyl-amino)-ethylamino] benzenesulfonic acid 2-(3-piperid-4-ylpropionyl-amino)benzothiazol-6-yl ester hydrochloride | LCMS: m/z 548 [M + H]$^+$, m/z 409: [M + H]$^+$ − $C_5H_{10}NC_2H_4CO$, m/z 275: [M + 2H]$^{2+}$ m/z 295(base peak).<br>1H NMR spectrum (300 MHz) - δ in ppm - in DMSO-d6: 1.32(m, 2H); from 1.45 to 1.65 (unresolved complex, 3H); 1.80 (broad d, J=12.5Hz, 2H); 2.52 (masked, 2H); 2.82(m, 2H); 3.03 (unresolved complex, 2H); 3.10 (unresolved complex, 2H); 3.25 (broad d, J=12.5Hz, 2H); 3.45 (masked, 2H); 3.69(t, J=5.5Hz, 2H); 6.72(broad d, J=9.0Hz, 2H); 6.99(dd, J=8.5 and 2.5Hz, 1H); 7.18(broad unresolved complex, 1H); 7.52(broad d, J=9.0Hz, 2H); 7.67(d, J=8.5Hz, 1H); 7.73(d, J=2.5Hz, 1H); 8.50(broad unresolved complex, 1H); 8.75 (broad unresolved complex, 1H); 8.91(broad unresolved complex, 2H); 12.4(broad s, 1H). |

INTERMEDIATE 26

Preparation of 4-isobutylaminobenzenesulfonic acid 2-tert-butoxycarbonylaminobenzothiazol-6-yl ester

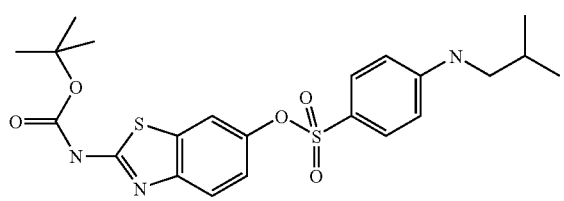

A solution of 4-fluorobenzenesulfonic acid 2-tert-butoxycarbonylamino-benzothiazol-6-yl ester (intermediate 15) (1 g, 2.32 mmol), isobutylamine (517 mg, 7.07 mmol) and cesium carbonate (845 mg, 2.59 mmol) in 12 ml of DMSO is stirred at 80° C. overnight. 60 ml of water are added to the reaction medium. The mixture is extracted with ethyl acetate. The organic phase is washed with water and with saturated sodium chloride solution, dried over magnesium sulfate and then evaporated to dryness. The residue is washed with ethyl ether to give 880 mg of 4-isobutylaminobenzenesulfonic acid 2-tert-butoxycarbonylaminobenzothiazol-6-yl ester (beige-colored solid) in a yield of 80%.

LC/MS (method A1): [M+H]+:478.01, retention time: 4.31 min.

INTERMEDIATE 27

Preparation of 4-isobutylaminobenzenesulfonic acid 2-aminobenzothiazol-6-yl ester

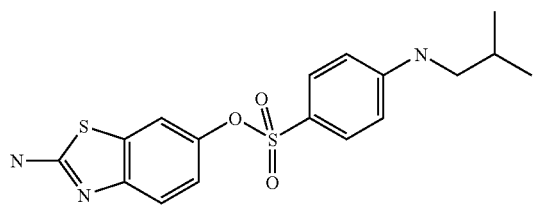

A solution of 4-isobutylaminobenzenesulfonic acid 2-tert-butoxycarbonyl-aminobenzothiazol-6-yl ester (intermediate 26) (880 mg, 1.93 mmol) and trifluoroacetic acid (5.7 ml, 74 mmol) in 6 ml of dichloromethane and 600 µl of water is stirred overnight at room temperature.

The reaction medium is concentrated to dryness and the residue is washed with ethyl ether to give 700 mg of 4-isobutylaminobenzenesulfonic acid 2-aminobenzothiazol-6-yl ester in the form of the trifluoroacetic acid salt (white solid) in a yield of 52%.

LC/MS(method A1): [M+H]+:378.05, retention time: 3.60 ml.

EXAMPLE 28

Preparation of 4-isobutylaminobenzenesulfonic acid 2-(2-piperid-4-ylacetylamino)benzothiazol-6-yl ester hydrochloride

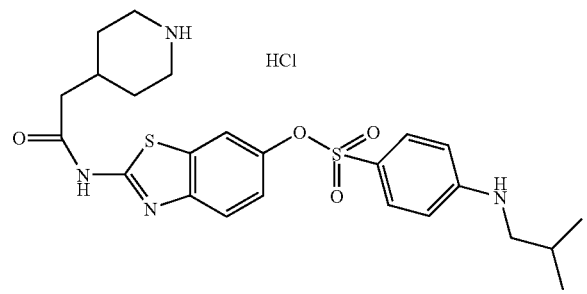

1st step: A solution of 4-isobutylaminobenzenesulfonic acid 2-aminobenzo-thiazol-6-yl ester (intermediate 27) (300 mg, 0.495 mmol), 4-carboxymethyl-piperidine-1-carboxylic acid tert-butyl ester (361 mg, 1.485 mmol), HBTU (563 mg, 1.485 mmol) and N,N-diisopropylethylamine (432 µl, 2.475 mmol) in 4 ml of dimethylformamide is stirred at room temperature overnight. Water is added to the reaction medium, which is extracted with ethyl acetate. The organic phase is washed with water and then with saturated sodium chloride solution, dried over magnesium sulfate and concentrated to dryness. The residue obtained is purified by HPLC on a Dynamax C18, 60 Å, 21×300 mm column with a 95/5 mixture of water/acetonitrile, for 5 minutes, with a gradient of from 5% to 40% in water for 5 minutes, with a gradient of from 40% to 80% of acetonitrile in water for 30 minutes, with a gradient of from 80% to 95% of acetonitrile in water for 5 minutes, and then with a 5/95 mixture of water/acetonitrile for 5 minutes with a flow rate of 20 ml/minute. The solvents each contain 0.07% (v/v) of trifluoroacetic acid. The fractions are collected every 30 seconds and are monitored by analytical HPLC on a Hypersil C18, 4.6×50 mm column, with a gradient of from 0 to 100% of acetonitrile in water, over 10 minutes at a flow rate of 1 ml/minute. The solvents each contain 0.07% (v/v) of trifluoroacetic acid. The fractions containing the expected product are concentrated to dryness to give 4-{[6-(4-isobutylamino-benzenesulfonyloxy)benzothiazol-2-ylcarbamoyl]methyl}piperidine-1-carboxylic acid tert-butyl ester.

2nd step: A solution of 4-{[6-(4-isobutylaminobenzenesulfonyloxy)benzo-thiazol-2-ylcarbamoyl]methyl}piperidine-1-carboxylic acid tert-butyl ester (110 mg, 182 µmol), dioxane (2 ml) and 4N hydrochloric acid in dioxane is stirred for 2 hours at room temperature. The reaction medium is concentrated to dryness and the residue obtained is washed with ethyl ether to give 183 mg of 4-isobutylaminobenzenesulfonic acid 2-(2-piperid-4-ylacetylamino)benzo-thiazol-6-yl ester hydrochloride (white powder) in a yield of 64%.

Mass: IE: m/z 502 [M+•], m/z 377: [M+•]—C$_7$H$_{12}$NO, m/z 212: [SO$_2$PhNHiBu]+• m/z 165: [377–212]+•, m/z 126: [C$_7$H$_{12}$NO]+• (base peak).

1H NMR spectrum (300 MHz)—δ in ppm—in DMSO-d6:

0.94 (d, J=6.5 Hz, 6H); 1.45 (m, 2H); from 1.77 to 1.88 (unresolved complex, 3H); 2.10 (broad unresolved complex, 1H); 2.52 (masked, 2H); 2.83 (m, 2H); 2.91 (d, J=6.5 Hz, 2H); 3.25 (broad d, J=12.5 Hz, 2H); 6.67 (broad d, J=9.0 Hz, 2H); 7.00 (dl, J=9.0 Hz, 1H); 7.15 (very broad unresolved complex, 1H); 7.45 (broad d, J=9.0 Hz, 2H); 7.67 (d, J=9.0 Hz, 1H); 7.73 (d, J=2.5 Hz, 1H); 8.62 (broad unresolved complex, 1H); 8.85 (broad unresolved complex, 1H); 12.5 (broad s, 1H)

EXAMPLE 29

Using the same method as in example 28, the following examples are prepared using 4-isobutylaminobenzenesulfonic acid 2-amino-benzothiazol-6-yl ester as precursor (intermediate 27) combined with various acids. These examples are presented in the following table:

| Example No. | Acid | compound | characterization |
|---|---|---|---|
| 29 a | (structure shown) | 4-Isobutylaminobenzenesulfonic acid 2-(3-piperid-4-ylpropionylamino)benzothiazol-6-yl ester hydrochloride | Mass: LCMS: m/z 517 [M + H]+ (base peak) IE: m/z 516 [M+], m/z 377: [M+] – C$_8$H$_{14}$NO, m/z 212: [SO$_2$PhNHiBu]+ m/z 165: [377 – 212]+ 1H NMR spectrum (400 MHz) - δ in ppm - in DMSO-d6: 0.94(d, J=7.0Hz, 6H); 1.32(m, 2H); from 1.50 to 1.65(unresolved complex, 3H); from 1.78 to 1.88(unresolved complex, 3H); 2.52(masked, 2H); 2.83(m, 2H); 2.92 (d, J=7.0Hz, 2H); 3.25(d, J=12.5Hz, 2H); 6.67(broad d, J=9.0Hz, 2H); 7.00 (dd, J=8.5 and 2.5Hz, 1H); from 6.90 to 7.10(very broad unresolved complex, 1H); 7.45(broad d, J=9.0Hz, 2H); 7.68(d, J=8.5Hz, 1H); 7.72(d, J=2.5Hz, 1H); 8.40(broad unresolved complex, 1H); 8.70 (broad unresolved complex, 1H); 12.45 (broad s, 1H). |

| Example No. | Acid | compound | characterization |
|---|---|---|---|
| 29 b | 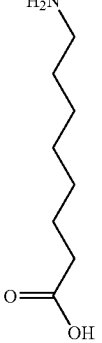 | 4-Isobutylaminobenzenesulfonic acid 2-(8-aminooctanoylamino)-benzothiazol-6-yl ester hydrochloride | Mass: LCMS: m/z 519 [M + H]$^+$ (base peak) IE: m/z 518 [M$^+$], m/z 377: [M$^+$] − CO(CH$_2$)$_7$NH$_2$, m/z 212: [SO$_2$PhNHiBu]$^+$ m/z 165: [377 − 212]$^+$ (base peak). 1H NMR spectrum (400 MHz) - δ in ppm - in DMSO-d6: 0.95(d, J=6.5Hz, 6H); 1.32(unresolved complex, 6H); 1.55(unresolved complex, 2H); 1.64(unresolved complex, 2H); 1.83 (mt, J=6.5Hz, 1H); 2.52(masked, 2H); 2.78(unresolved complex, 2H); 2.91(d, J=6.5Hz, 2H); 6.67(broad d, J=9.0Hz, 2H); 6.98(broad d, J=9.0Hz, 1H); 7.45 (broad d, J=9.0Hz, 2H); 7.68(d, J=9.0 Hz, 1H); 7.72(broad s, 1H); 7.89(broad unresolved complex, 3H); 12.4(broad s, 1H). |

INTERMEDIATE 30

Preparation of thiophene-2-sulfonic acid 2-tert-butoxy-carbonylaminobenzothiazol-6-yl ester

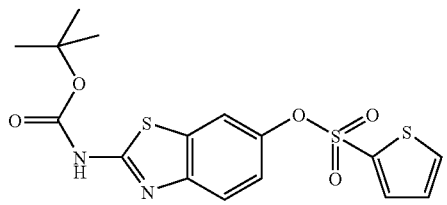

A solution of (6-hydroxybenzothiazol-2-yl)carbamic acid tert-butyl ester (intermediate 14) (527 mg, 1.979 mmol), 2-thiophenesulfonyl chloride (433 mg, 2.37 mmol) and triethylamine (677 µl, 4.75 mmol) in 10 ml of acetone is stirred overnight at room temperature. The reaction medium is concentrated to dryness. The residue obtained is washed with water, with acetone and then with ethyl ether to give 621 mg of thiophene-2-sulfonic acid 2-tert-butoxycarbonylaminobenzothiazol-6-yl ester (light gray powder) in a yield of 76%.

LC/MS: [M+H]+=412.98, retention time: 3.99 min.

INTERMEDIATE 31

Preparation of thiophene-2-sulfonic acid 2-aminobenzo-thiazol-6-yl ester

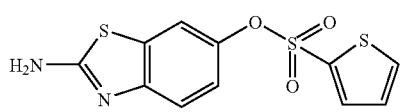

A solution of thiophene-2-sulfonic acid 2-tert-butoxycarbonylaminobenzo-thiazol-6-yl ester (intermediate 30) (1.5 g, 3.63 mmol) and trifluoroacetic acid (15 ml, 196 mmol) in 15 ml of dichloromethane and 600 µl of water is stirred for 2 hours at room temperature. The reaction medium is concentrated to dryness to give 900 mg of thiophene-2-sulfonic acid 2-aminobenzothiazol-6-yl ester in the form of the trifluoroacetic acid salt (oil) in a yield of 76%.

LC/MS (method A1): [M+H]+:313, retention time: 3.11 min.

EXAMPLE 32

Preparation of thiophene-2-sulfonic acid 2-[(piperidine-4-carbonyl)amino]benzothiazol-6-yl ester; compound with trifluoroacetic acid

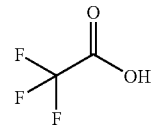

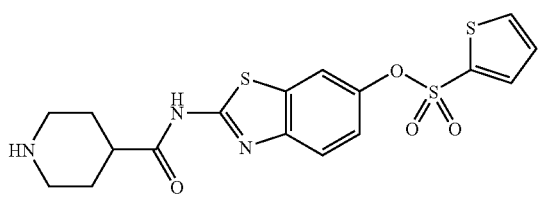

1st step: A solution of thiophene-2-sulfonic acid 2-aminobenzothiazol-6-yl ester (intermediate 31) (80 mg, 0.256 mmol), Boc-isonipecotic acid (176 mg, 0.768 mmol) HBTU (291 mg, 0.768 mmol) and N,N-diisopropylethylamine (223 µl, 1.28 mmol) in 4 ml of dimethylformamide is stirred for 3 days at room temperature. 30 ml of water are added to the reaction medium, which is extracted with ethyl acetate. The organic phase is washed with water and with saturated sodium chloride solution, dried over magnesium sulfate and concentrated to dryness to give 4-[6-thiophene-2-sulfonyloxy)benzothiazol-2-ylcarbamoyl]piperidine-1-carboxylic acid tert-butyl ester.

LC/MS:[M+H]+:523.96, retention time: 4.00 min.

2nd step: A solution of 4-[6-thiophene-2-sulfonyloxy)benzothiazol-2-yl carbamoyl]piperidine-1-carboxylic acid tert-butyl ester and trifluoroacetic acid (1.5 ml) in 1.5 ml of dichloromethane and 100 µl of water is stirred overnight at room temperature. The reaction medium is concentrated to dryness, the residue is taken up in 500 µl of DMSO and a sample is purified by preparative LC/MS (method B), to give 3 mg of thiophene-2-sulfonic acid 2-[(piperidine-4-carbonyl)amino]benzothiazol-6-yl ester; compound with trifluoroacetic acid.

LC/MS: [M+H]+:423.97, retention time: 2.74 min.

EXAMPLE 33

Using the same method as in example 32, the following examples are prepared using thiophene-2-sulfonic acid 2-aminobenzothiazol-6-yl ester as precursor (intermediate 31) combined with various acids. These examples are presented in the following table; the LCMSs are performed according to method A1:

| Example No. | acid | compound | [M + H]+ | retention time (min) |
|---|---|---|---|---|
| 33a | 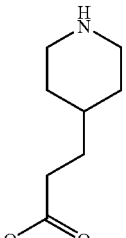 | Thiophene-2-sulfonic acid 2-(3-piperid-4-ylpropionylamino)benzothiazol-6-yl ester; compound with trifluoroacetic acid | 452.01 | 2.77 |
| 33b | 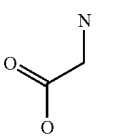 | Thiophene-2-sulfonic acid 2-(2-aminoacetylamino)benzothiazol-6-yl ester; compound with trifluoroacetic acid | 369.98 | 2.62 |
| 33c | 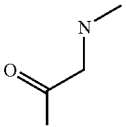 | Thiophene-2-sulfonic acid 2-(2-methylaminoacetylamino)benzothiazol-6-yl ester; compound with trifluoroacetic acid | 384.00 | 2.67 |
| 33d | 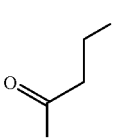 | Thiophene-2-sulfonic acid 2-(3-aminopropionylamino)benzothiazol-6-yl ester; compound with trifluoroacetic acid | 383.99 | 2.65 |

| Example No. | acid | compound | [M + H]+ | retention time (min) |
|---|---|---|---|---|
| 33f | H₂N-(CH₂)₇-COOH | Thiophene-2-sulfonic acid 2-(8-amino-octanoylamino)benzothiazol-6-yl ester; compound with trifluoroacetic acid | 453.98 | 2.91 |
| 33g | (Et)₂N-CH₂CH₂-C(O)O- | Thiophene-2-sulfonic acid 2-(3-diethyl-aminopropionylamino)benzothiazol-6-yl ester; compound with trifluoroacetic acid | 440.03 | 2.81 |
| 33h | cyclopropane-C(O)O- | Thiophene-2-sulfonic acid 2-(cyclopropanecarbonylamino)benzothiazol-6-yl ester | 380.99 | 3.63 |

INTERMEDIATE 34

Preparation of 4-(2-diisopropylaminoethylamino)benzene-sulfonic acid 2-aminobenzothiazol-6-yl ester

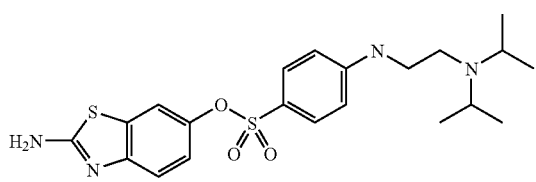

A solution of 4-fluorobenzenesulfonic acid 2-aminobenzothiazol-6-yl ester (intermediate 16) (100 mg, 0.225 mmol) and N,N-diisopropylethylenediamine (395 μl, 2.25 mmol) in 5 ml of NMP is heated at 150° C. by microwave using an "Emrys™ Optimizer" machine for 20 minutes. The crude reaction product is taken up in 50 ml of ethyl acetate and the resulting solution is washed with 5 times 50 ml of water. After separation of the phases by settling, the organic phase is dried over sodium sulfate, filtered and evaporated under reduced pressure to give 100 mg of 4-(2-diisopropylaminoethylamino)benzenesulfonic acid 2-aminobenzothiazol-6-yl ester.

LC/MS (method A1): [M+H]+=449.22, retention time: 2.36 min.

INTERMEDIATE 35

Preparation of 3-{6-[4-(2-diisopropylaminoethylamino)-benzenesulfonyloxy]benzothiazol-2-ylcarbamoyl}azetidine-1-carboxylic acid tert-butyl ester

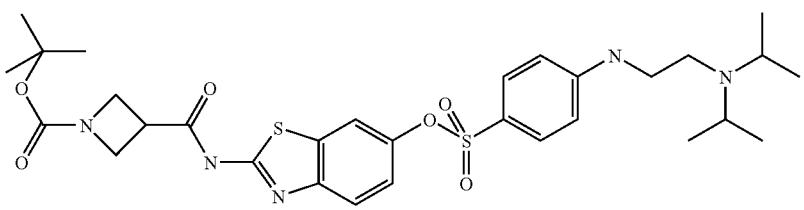

68 mg of azetidine-1,3-dicarboxylic acid mono-tert-butyl ester, 256 mg of HBTU and 235 µl of DIEA are added to a solution of 4-(2-diisopropylamino-ethylamino)benzenesulfonic acid 2-aminobenzothiazol-6-yl ester (inter-mediate 34) (100 mg, 0.225 mmol) in 5 ml of dimethylformamide. The solution obtained is stirred for 20 hours at room temperature. After addition of 50 ml of water, the reaction medium is extracted with 3 times 25 ml of ethyl acetate. The extracts are dried over magnesium sulfate, filtered and evaporated under reduced pressure to give 700 mg of crude oil. This oil is purified by elution in a 95/5 dichloromethane/methanol mixture at a flow rate of 10 ml/minute, on 20 g of silica, to give 39 mg of 3-{6-[4-(2-diisopropylaminoethylamino)-benzene-sulfonyloxy]benzothiazol-2-ylcarbamoyl}azetidine-1-carboxylic acid tert-butyl ester.

LC/MS: [M+H]+: 632.11 retention time: 3.00 min. Method A1

INTERMEDIATE 36

Preparation of 4-(2-diisopropylaminoethylamino) benzene-sulfonic acid 2-(8-tert-butoxycarbonylaminooctanoylamino)benzothiazol-6-yl ester

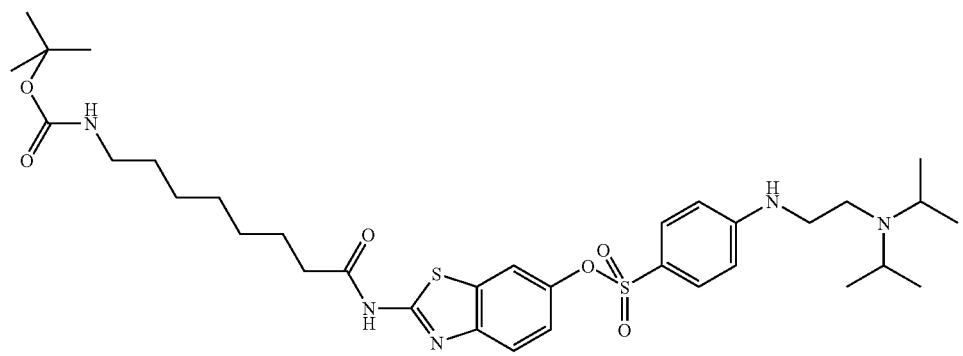

175 mg of 8-tert-butoxycarbonylaminooctanoic acid, 256 mg of HBTU and 235 µl of DIEA are added to a solution of 4-(2-diisopropylaminoethylamino)-benzenesulfonic acid 2-aminobenzothiazol-6-yl ester (intermediate 34) (100 mg, 0.225 mmol) in 5 ml of dimethylformamide. The solution obtained is stirred for 20 hours at room temperature. After addition of 50 ml of water, the reaction mixture is extracted with 3 times 25 ml of ethyl acetate. The extracts are dried over magnesium sulfate, filtered and evaporated under reduced pressure to give 338 mg of crude oil. This oil is purified by elution in a 95/5 dichloromethane/methanol mixture at a flow rate of 10 ml/minute, on 10 g of silica, to give 153 mg of 4-(2-diisopropylaminoethylamino)benzenesulfonic acid 2-(8-tert-butoxycarbonylaminooctanoylamino)benzothiazol-6-yl ester.

LC/MS: [M+H]+: 690.33 retention time: 3.25 min. Method A1

INTERMEDIATE 37

Preparation of 4-(2-diisopropylaminoethylamino) benzene-sulfonic acid 2-[(1-tert-butoxycarbonylaminocyclopentanecarbonyl)amino]-benzothiazol-6-yl ester.

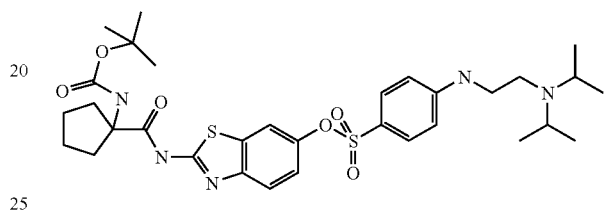

155 mg of 1-tert-butoxycarbonylaminocyclopentanecarboxylic acid, 256 mg of HBTU and 235 µl of DIEA are added to a solution of 4-(2-diisopropyl-aminoethylamino) benzenesulfonic acid 2-aminobenzothiazol-6-yl ester (intermediate 34) (100 mg, 0.225 mmol) in 5 ml of dimethylformamide. The solution obtained is stirred for 20 hours at room temperature. After addition of 50 ml of water, the reaction mixture is extracted with 3 times 25 ml of ethyl acetate. The extracts are dried over magnesium sulfate, filtered and evaporated under reduced pressure to give 720 mg of crude oil. This oil is purified by elution in a 95/5 dichloromethane/methanol mixture at a flow rate of 10 ml/minute on 10 g of silica, to give 120 mg of 4-(2-diisopropylaminoethylamino)benzene-sulfonic acid 2-[(1-tert-butoxycarbonyl aminocyclopentanecarbonyl)amino]-benzothiazol-6-yl ester.

LC/MS: [M+H]+: 660.56 retention time: 3.11 min. Method A1

INTERMEDIATE 38

Preparation of 4-({6-[4-(2-diisopropylaminoethylamino)-benzenesulfonyloxy]benzothiazol-2-carbamoyl}methyl)piperidine-1-carboxylic acid tert-butyl ester

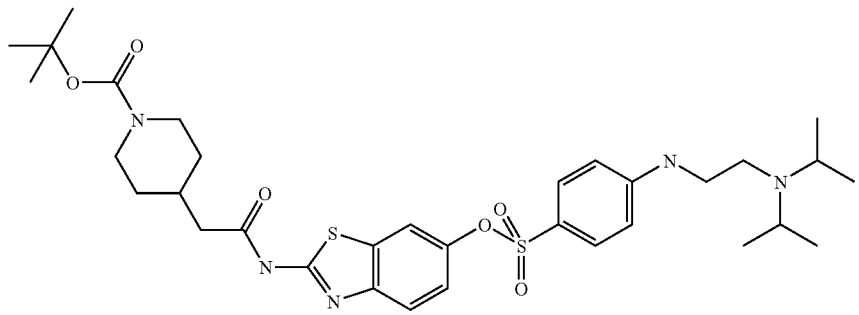

164 mg of 4-carboxymethylpiperidine-1-carboxylic acid tert-butyl ester, 256 mg of HBTU and 235 µl of DIEA are added to a solution of 4-(2-diisopropylaminoethylamino)benzenesulfonic acid 2-aminobenzothiazol-6-yl ester (intermediate 34) (100 mg, 0.225 mmol) in 5 ml of dimethylformamide. The solution obtained is stirred for 20 hours at room temperature. After addition of 50 ml of water, the reaction mixture is extracted with 3 times 25 ml of ethyl acetate. The extracts are dried over magnesium sulfate, filtered and evaporated under reduced pressure to give 380 mg of crude oil. This oil is purified by elution in a 95/5 dichloromethane/methanol mixture at a flow rate of 10 ml/minute on 10 g of silica, to give 90 mg of 4-({6-[4-(2-diisopropyl-aminoethylamino)benzenesulfonyloxy]benzothiazol-2-carbamoyl}methyl)-piperidine-1-carboxylic acid tert-butyl ester.

LC/MS: [M+H]+: 674.57 retention time: 3.11 min. Method A1

EXAMPLE 39

Preparation of 4-(2-diisopropylaminoethylamino) benzenesulfonic acid 2-[(azetidine-3-carbonyl)amino]benzothiazol-6-yl ester

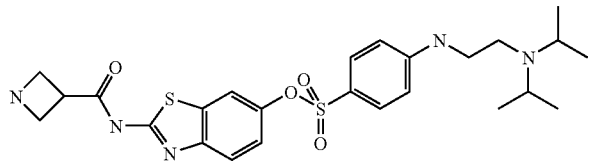

1.5 ml of hydrochloric dioxane are added to a solution of 39 mg of 3-{6-[4-(2-diisopropylaminoethylamino)benzenesulfonyloxy]benzothiazol-2-yl-carbamoyl}azetidine-1-carboxylic acid tert-butyl ester (intermediate 35) in 1.5 ml of dioxane. The resulting solution is stirred for 5 hours at room temperature and then evaporated under reduced pressure to give 49 mg of oil, which is purified by LC/MS to give 9.7 mg of 4-(2-diisopropylamino-ethylamino)benzenesulfonic acid 2-[(azetidine-3-carbonyl)amino]benzo-thiazol-6-yl ester.

MS: DCI: m/z=532 [M+H]+
ES+: m/z=532 [M+H]+; m/z=266.8 [M+2H]++

EXAMPLE 40

Preparation of 4-(2-diisopropylaminoethylamino)benzenesulfonic acid 2-(8-aminooctanoylamino)benzothiazol-6-yl ester

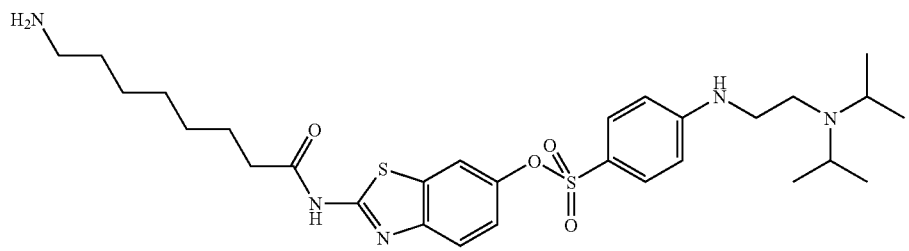

3 ml of hydrochloric dioxane are added to a solution of 153 mg of 3-{6-[4-(2-diisopropylaminoethylamino)benzenesulfonyloxy]benzothiazol-2-yl-carbamoyl}azetidine-1-carboxylic acid tert-butyl ester (intermediate 36) in 3 ml of dioxane. The resulting solution is stirred for 5 hours at room temperature and then evaporated under reduced pressure to give 152 mg of 4-(2-diisopropylaminoethylamino)benzenesulfonic acid 2-(8-aminooctanoylamino)-benzothiazol-6-yl ester.

MS: DCI: m/z=590 [M+H]+

ES+: m/z=590 [MH]+; m/z=295.95 [M+2H]++

1H NMR spectrum (300 MHz)—δ in ppm—in DMSO-d6: From 1.20 to 1.38 (unresolved complex, 16H); from 1.42 to 1.68 (unresolved complex, 6H); 2.29 (t, J=7.0 Hz, 2H); 2.74 (unresolved complex, 4H); 3.16 (unresolved complex, 2H); from 3.50 to 3.80 (unresolved complex, 2H); 6.71 (broad d, J=9.0 Hz, 2H); 6.96 (broad d, J=9.0 Hz, 1H); 7.33 (broad t, J=6.0 Hz, 1H); 7.51 (broad d, J=9.0 Hz, 2H); 7.64 (d, J=9.0 Hz, 1H); 7.68 (broad s, 1H); 7.85 (broad unresolved complex, 3H); 9.98 (unresolved complex, 1H); 12.4 (broad s, 1H).

EXAMPLE 41

Preparation of 4-(2-diisopropylaminoethylamino)benzenesulfonic acid 2-[(1-aminocyclopentanecarbonyl)amino]benzothiazol-6-yl ester

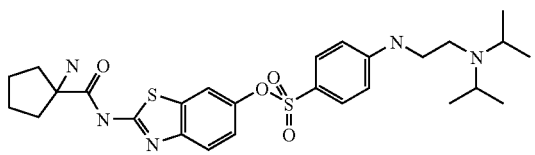

3 ml of hydrochloric dioxane are added to a solution of 120 mg of 4-(2-diisopropylaminoethylamino)benzenesulfonic acid 2-[(1-tert-butoxycarbonyl-aminocyclopentanecarbonyl)amino]benzothiazol-6-yl ester (intermediate 37) in 3 ml of dioxane. The resulting solution is stirred for 5 hours at room temperature and then evaporated under reduced pressure to give 90 mg of oil, which is purified by LC/MS to give 32 mg of 4-(2-diisopropylaminoethyl-amino)benzenesulfonic acid 2-[(1-aminocyclopentanecarbonyl)amino]benzo-thiazol-6-yl ester.

1H NMR spectrum (300 MHz)—δ in ppm—in DMSO-d6+1 drop of AcOD: 1.26 (d, J=6.5 Hz, 12H); from 1.85 to 2.02 (unresolved complex, 6H); 2.35 (unresolved complex, 2H); 3.19 (t, J=7.0 Hz, 2H); 3.50 (t, J=7.0 Hz, 2H); 3.68 (mt, J=6.5 Hz, 2H); 6.72 (broad d, J=9.0 Hz, 2H); 6.98 (dd, J=8.5 and 2.5 Hz, 1H); 7.55 (broad d, J=9.0 Hz, 2H); 7.76 (d, J=8.5 Hz, 1H); 7.85 (d, J=2.5 Hz, 1H).

EXAMPLE 42

Preparation of 4-(2-diisopropylaminoethylamino)benzenesulfonic acid 2-(2-piperid-4-ylacetylamino)benzothiazol-6-yl ester

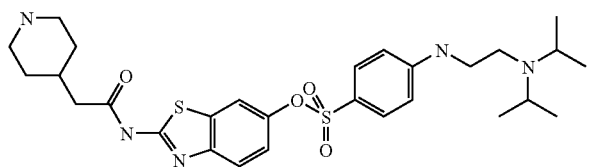

3 ml of hydrochloric dioxane are added to a solution of 90 mg of 4-({6-[4-(2-diisopropylaminoethylamino)benzenesulfonyloxy]benzothiazol-2-carbamoyl}-methyl)piperidine-1-carboxylic acid tert-butyl ester (intermediate 38) in 3 ml of dioxane. The resulting solution is stirred for 5 hours at room temperature and then evaporated under reduced pressure to give 90 mg of oil, which is purified by LC/MS to give 101 mg of 4-(2-diisopropylaminoethylamino)benzene-sulfonic acid 2-(2-piperid-4-ylacetylamino)benzothiazol-6-yl ester.

LC/MS: [M+H]+: 574.23 retention time: 2.24 min. Method A1

MS: DCI: m/z=574 [MH+]

ES+: m/z=574 [MH+]; m/z=287.9 [(M+2H)/2]+

1H NMR spectrum (400 MHz)—δ in ppm—in DMSO-d6+1 drop of AcOD at 383 K (110° C.):

1.33 (d, J=7.0 Hz, 12H); from 1.42 to 1.58 (unresolved complex, 2H); from 1.85 to 1.95 (unresolved complex, 2H); 2.15 (unresolved complex, 1H); 2.31 (d, J=7.0 Hz, 2H); from 2.87 to 2.97 (unresolved complex, 2H); 3.22 (t, J=6.5 Hz, 2H); from 3.24 to 3.32 (unresolved complex, 2H); 3.58 (t, J=6.5 Hz, 2H); from 3.65 to 3.75 (unresolved complex, 2H); 6.75 (broad d, J=9.0 Hz, 2H); 7.08 (dd, J=8.5 and 2.5 Hz, 1H); 7.58 (broad d, J=9.0 Hz, 2H); 7.62 (d, J=2.5 Hz, 1H); 7.65 (d, J=8.5 Hz, 1H).

EXAMPLE 43

Preparation of 4-(2-Diisopropylaminoethylamino)benzenesulfonic acid 2-acetylaminobenzothiazol-6-yl ester

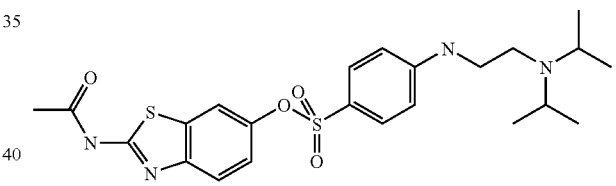

28 mg of acetic acid, 177.5 mg of HBTU and 163 µl of DIEA are added to a solution of 4-(2-diisopropylaminoethylamino)benzenesulfonic acid 2-amino-benzothiazol-6-yl ester (intermediate 34) (70 mg, 0.156 mmol) in 4 ml of dimethylformamide. The solution obtained is stirred for 20 hours at room temperature. After addition of 50 ml of water, the reaction mixture is extracted with 3 times 25 ml of ethyl acetate. The extracts are dried over magnesium sulfate, filtered and evaporated under reduced pressure to give 130 mg of crude oil. This oil is purified by LC/MS to give 15 mg of 4-(2-diisopropylamino-ethylamino)benzenesulfonic acid 2-acetylaminobenzothiazol-6-yl ester.

IR: 3420; 2989; 2680; 1674; 1599; 1542; 1452; 1367; 1268; 1202; 1176; 1161; 1134; 1094; 914; 851; 831; 753; 720 and 579 cm$^{-1}$ 1H NMR spectrum (300 MHz)—δ in ppm—in DMSO-d6:

1.30 (d, J=6.5 Hz, 12H); 2.22 (s, 3H); 3.23 (unresolved complex, 2H); 3.51 (unresolved complex, 2H); 3.72 (unresolved complex, 2H); 6.74 (broad d, J=9.0 Hz, 2H); 6.90 (broad unresolved complex, 1H); 7.03 (broad d, J=9.0 Hz, 1H); 7.56 (broad d, J=9.0 Hz, 2H); 7.68 (d, J=9.0 Hz, 1H); 7.70 (d, J=3.0 Hz, 1H); 8.46 (unresolved complex, 1H); 12.4 (broad s, 1H).

EXAMPLE 43a

Preparation of 4-(2-diisopropylaminoethylamino)benzene-sulfonic acid 2-acetylaminobenzothiazol-6-yl ester hydrochloride

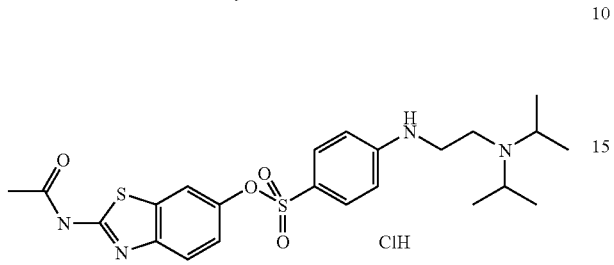

Example 43a was synthesized from 250 mg (0.557 mmol) of 4-(2-diisopropyl-aminoethylamino)benzenesulfonic acid 2-aminobenzothiazol-6-yl ester (inter-mediate 34) as a solution with 57 mg (0.557 mmol) of acetic anhydride and 216 mg (1.671 mmol) of N,N-diisopropylethylamine in 10 ml of dichloro-methane. The reaction medium is stirred overnight, the same amounts of acetic anhydride and N,N-diisopropyl-ethylamine are then added twice and the reaction is continued for 3 days at room temperature. 50 ml of dichloro-methane are then added, and the reaction medium is washed with water. 2N hydrochloric acid solution is added to the organic phase to pH 3 and the resulting organic phase is then washed with saturated aqueous sodium chloride solution, dried over magnesium sulfate and evaporated to dryness to give 140 mg of 4-(2-diisopropylaminoethylamino)benzenesulfonic acid 2-acetylaminobenzothiazol-6-yl ester hydrochloride in a yield of 48%.

Mass: ES m/z=491 MH⁺ base peak NMR: 1H NMR spectrum at 300 MHz on a Bruker Avance DPX-300 spectrometer with the chemical shifts (δ in ppm)—in the solvent dimethyl sulfoxide-d6 (DMSO-$d_6$) referenced to 2.50 ppm: from 0.90 to 1.35 (m, 12H); 2.20 (s, 3H); 3.18 (broad m, 2H); 3.53 (broad m, 2H); from 3.60 to 3.77 (broad m, 2H); 6.72 (broad d, J=9.0 Hz, 2H); 7.00 (dd, J=2.5 and 8.5 Hz, 1H); 7.04 (broad m, 1H); 7.53 (broad d, J=9.0 Hz, 2H); 7.66 (d, J=8.5 Hz, 1H); 7.68 (d, J=2.5 Hz, 1H); 9.09 (broad m, 1H); 12.4 (broad s, 1H).

IR:KBr

3427; 2978; 2658; 1693; 1598; 1542; 1452; 1367; 1267; 1160; 1093; 913; 850 and 578 cm⁻¹

EXAMPLE 44

4-(2-Diisopropylaminoethylamino)benzenesulfonic acid 2-(2-methoxyacetylamino)benzothiazol-6-yl ester

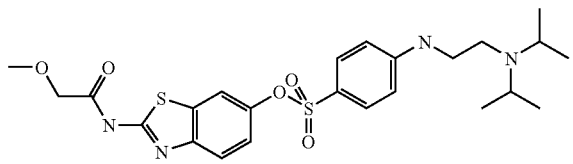

42.1 mg of methoxyacetic acid, 177.5 mg of HBTU and 163 µl of DIEA are added to a solution of 4-(2-diisopropylaminoethylamino)benzenesulfonic acid 2-aminobenzothiazol-6-yl ester (intermediate 34) (70 mg, 0.156 mmol) in 4 ml of dimethylformamide. The solution obtained is stirred for 20 hours at room temperature. After addition of 50 ml of water, the reaction mixture is extracted with 3 times 25 ml of ethyl acetate. The extracts are dried over magnesium sulfate, filtered and evaporated under reduced pressure to give 98 mg of crude oil. This oil is purified by LC/MS to give 47.8 mg of 4-(2-diisopropyl-aminoethylamino)benzenesulfonic acid 2-(2-methoxyacetylamino)benzo-thiazol-6-yl ester.

IR: 3390; 2993; 2666; 1674; 1599; 1541; 1452; 1365; 1269; 1202; 1175; 1161; 1125; 1094; 914; 852; 830; 757; 720 and 570 cm⁻¹

1H NMR spectrum (300 MHz)—δ in ppm—in DMSO-d6: 1.29 (d, J=6.5 Hz, 12H); 3.23 (unresolved complex, 2H); 3.40 (s, 3H); 3.52 (unresolved complex, 2H); 3.72 (broad unresolved complex, 2H); 4.22 (s, 2H); 6.75 (broad d, J=9.0 Hz, 2H); 6.90 (broad t, J=6.0 Hz, 1H); 7.05 (dd, J=9.0 and 2.5 Hz, 1H); 7.55 (broad d, J=9.0 Hz, 2H); 7.70 (d, J=9.0 Hz, 1H); 7.72 (d, J=2.5 Hz, 1H); 8.48 (unresolved complex, 1H); 12.35 (s, 1H).

EXAMPLE 44a

Preparation of 4-(2-diisopropylaminoethylamino) benzene-sulfonic acid 2-(2-methoxyacetylamino) benzothiazol-6-yl ester hydrochloride

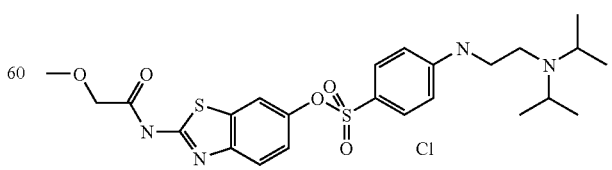

Example 44a is synthesized according to the method of Example 44, starting with 750 mg (1.672 mmol) of 4-(2- diisopropylaminoethylamino)benzenesulfonic acid 2-aminobenzothiazol-6-yl ester (intermediate 34) to give: crude 4-(2-di-isopropylaminoethylamino)benzenesulfonic acid 2-(2-methoxyacetylamino)-benzothiazol-6-yl ester. This product was dissolved in 1 ml of methanol and 3 ml of dioxane. 4 ml of dioxane/4N HCl were added to the solution. The reaction medium is stirred at room temperature overnight and then evaporated to dryness. The residue obtained is purified by flash chromatography on a first cartridge of 20 g of silica with a gradient from 0 to 10% of methanol in dichloromethane. Since the product obtained has a purity of 90%, a second purification is performed on a cartridge of 50 g of silica with a gradient of 0 to 10% of methanol in dichloromethane over 1 hour 30 minutes at a flow rate of 20 ml/min. After concentrating to dryness the fractions containing the product, 205 mg of 4-(2-diisopropylaminoethylamino)benzenesulfonic acid 2-(2-methoxyacetylamino)benzothiazol-6-yl ester hydrochloride are obtained in a yield of 22%.

Mass: ES m/z=521 MH$^+$ base peak

NMR: 1H NMR spectrum at 300 MHz on a Bruker Avance DPX-300 spectrometer with the chemical shifts (δ in ppm)—in the solvent dimethyl sulfoxide-d$_6$ (DMSO-d$_6$) referenced to 2.50 ppm: from 0.80 to 1.40 (m, 12H); from 2.90 to 3.70 (partially masked m, 6H); 3.38 (s, 3H); 4.20 (s, 2H); 6.68 (broad d, J=8.5 Hz, 2H); 7.00 (dd, J=2.5 and 8.5 Hz, 1H); 7.49 (broad d, J=8.5 Hz, 2H); 7.68 (d, J=8.5 Hz, 1H); 7.70 (d, J=2.5 Hz, 1H); 12.35 (broad s, 1H).

IR:KBr

3388; 2965; 2653; 1704; 1598; 1539; 1451; 1363; 1160; 1093; 914; 852; 754 and 567 cm$^{-1}$

EXAMPLE 45

4-(2-Diisopropylaminoethylamino)benzenesulfonic acid 2-(cyclo-pentanecarbonylamino)benzothiazol-6-yl ester

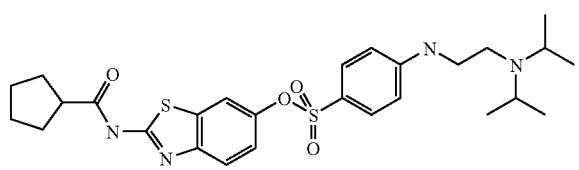

42.1 mg of methoxyacetic acid, 177.5 mg of HBTU and 163 µl of DIEA are added to a solution of 4-(2-diisopropylaminoethylamino)benzenesulfonic acid 2-aminobenzothiazol-6-yl ester (intermediate 34) (70 mg, 0.156 mmol) in 4 ml of dimethylformamide. The solution obtained is stirred for 20 hours at room temperature. After addition of 50 ml of water, the reaction mixture is extracted with 3 times 25 ml of ethyl acetate. The extracts are dried over magnesium sulfate, filtered and evaporated under reduced pressure to give 135 mg of crude oil. This oil is purified by LC/MS to give 55.2 mg of 4-(2-diisopropyl-aminoethylamino)benzenesulfonic acid 2-(cyclopentanecarbonylamino)-benzothiazol-6-yl ester.

IR: 3423; 2968; 2672; 1673; 1599; 1541; 1451; 1365; 1261; 1202; 1175; 1161; 1137; 1094; 916; 852; 829; 752; 720 and 568 cm$^{-1}$ 1H NMR spectrum (300 MHz)—δ in ppm—in DMSO-d6+1 drop of AcOD: 1.27 (d, J=6.5 Hz, 12H); from 1.52 to 1.80 (unresolved complex, 7H); 1.90 (unresolved complex, 1H); 2.97 (mt, J=7.5 Hz, 1H); 3.20 (t, J=6.5 Hz, 2H); 3.50 (t, J=6.5 Hz, 2H); 3.69 (mt, J=6.5 Hz, 2H); 6.71 (broad d, J=9.0 Hz, 2H); 7.04 (dd, J=9.0 and 2.5 Hz, 1H); 7.53 (broad d, J=9.0 Hz, 2H); 7.58 (d, J=9.0 Hz, 1H).

INTERMEDIATE 46

Preparation of 4-fluorobenzenesulfonic acid 2-(6-tert-butoxy-carbonylaminohexanoylamino)benzothiazol-6-yl ester

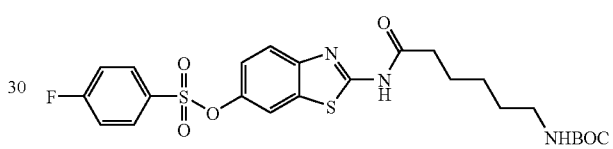

A solution of 4-fluorobenzenesulfonic acid 2-aminobenzothiazol-6-yl ester (intermediate 16, brevetbenzothiazole_V2) (0.15 g, 0.46 mmol), BOC-6-aminohexanoic acid (0.128 g, 0.555 mmol), HATU (0.211 g, 0.555 mmol) and N,N-diisopropylethylamine (95 µl, 0.555 mmol) in 2 ml of DMF, in a 20 ml round-bottomed flask equipped with a magnetic bar, is heated at about 60° C. (ext.) for 5 hours.

The reaction medium is extracted with ethyl acetate, washed with N hydrochloric acid solution and then with water. The organic phase is dried over sodium sulfate, filtered and then evaporated to dryness. The residue is purified by chromatography using Quad 12/25 on a Biotage cartridge (40 g of silica), eluting with a 97/3 methylene chloride/isopropanol mixture. After evaporating off the solvent, 0.199 g of 4-fluorobenzenesulfonic acid 2-(6-tert-butoxycarbonylaminohexanoylamino)benzothiazol-6-yl ester are recovered in a yield of 80%.

INTERMEDIATE 47

Preparation of 4-(2-diisopropylaminoethylamino) benzene-sulfonic acid 2-(6-tert-butoxycarbonylaminohexanoylamino)benzothiazol-6-yl ester

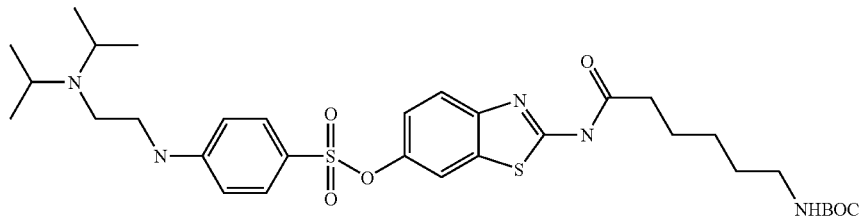

A solution of 0.194 g of 4-fluorobenzenesulfonic acid 2-(6-tert-butoxycarbonyl-aminohexanoylamino)benzothiazol-6-yl ester (0.194 g, 0.36 mmol) and N,N-diisopropylethylenediamine (0.33 ml, 1.8 mmol) in 4 ml of NMP is heated for 10 minutes at 150° C. by microwave. The crude reaction product is extracted with EtOAc and washed with water. The organic phase is dried over sodium sulfate, filtered and then evaporated to give 1.8 g (yellow liquid). This material is chromatographed on silica 60 (40-63 μm), eluting with a 93/7 CH$_2$Cl$_2$/MeOH mixture. After evaporating off the solvent, a gum (0.215 g) is obtained, which is triturated with water. The water is removed and the gum is then taken up in toluene and evaporated to dryness, to give 0.13 g of 4-(2-diisopropylaminoethylamino)benzenesulfonic acid 2-(6-tert-butoxycarbonyl-aminohexanoylamino)benzothiazol-6-yl ester, i.e. a yield of 54%.

EXAMPLE 49

Preparation of
4-(2-diisopropylaminoethylamino)benzenesulfonic acid 2-(6-aminohexanoylamino)benzothiazol-6-yl ester hydrochloride

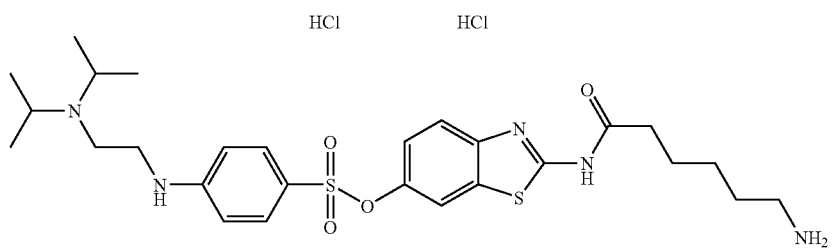

0.12 g of 4-(2-diisopropylaminoethylamino)benzenesulfonic acid 2-(6-tert-butoxycarbonylaminohexanoylamino)benzothiazol-6-yl ester is placed in 2 ml of EtOAc in a 10 ml round-bottomed flask equipped with a magnetic bar, followed by dropwise addition of 0.5 ml of hydrochloric acid dissolved in EtOAc. A gum forms, and is stirred for 1 hour at room temperature.

The reaction medium is taken up in water and then brought to pH 8 with 28% aqueous ammonia. The mixture is extracted with EtOAc and washed with water, and the organic phase is then dried over sodium sulfate. After filtration, the filtrate is evaporated to dryness to give 0.1 g of white powder, which is dissolved in 5 ml of methanol and then brought to pH 2 with hydrochloric acid dissolved in EtOAc. The suspension is evaporated to dryness and the residue is taken up in 5 ml of water and then freeze-dried to give 91 mg of 4-(2-diisopropylaminoethylamino)benzenesulfonic acid 2-(6-aminohexanoyl-amino)benzothiazol-6-yl ester hydrochloride, i.e. an 80% yield.

INTERMEDIATE 50

Preparation of 4-fluorobenzenesulfonic acid 2-(7-tert-butoxy-carbonylaminoheptanoylamino)benzothiazol-6-yl ester

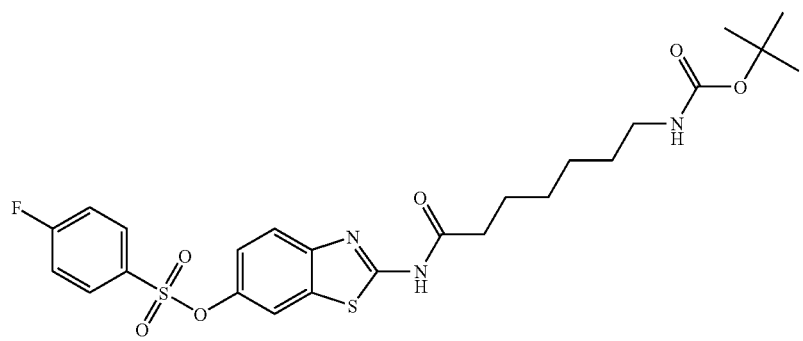

According to the method of intermediate 46, 4-fluorobenzenesulfonic acid 2-(7-tert-butoxycarbonylaminoheptanoylamino)benzothiazol-6-yl ester is prepared via the action of 4-fluorobenzenesulfonic acid 2-aminobenzothiazol-6-yl ester (intermediate 16, brevetbenzothiazole_V2) with BOC-7-amino-heptanoic acid to give 0.164 g of product.

INTERMEDIATE 51

Preparation of 4-(2-diisopropylaminoethylamino)benzene-sulfonic acid 2-(7-tert-butoxycarbonylaminoheptanoylamino)benzothiazol-6-yl ester

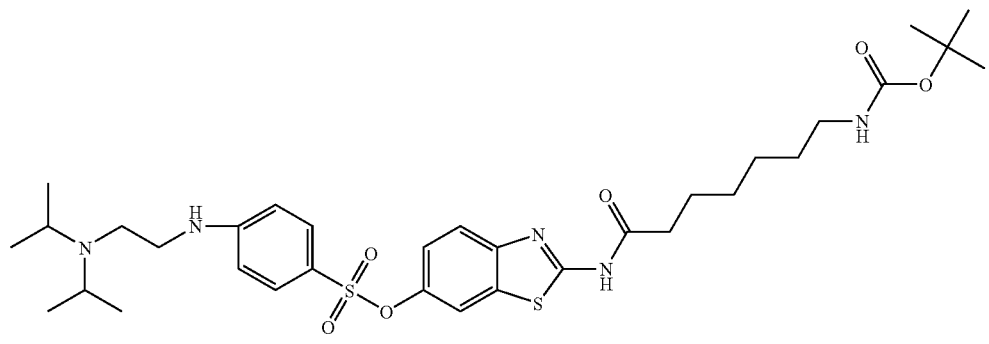

According to the method of intermediate 47, 4-(2-diisopropylaminoethylamino)benzenesulfonic acid 2-(7-tert-butoxycarbonylaminoheptanoylamino)-benzothiazol-6-yl ester is prepared via the action of 4-fluorobenzenesulfonic acid 2-(7-tert-butoxycarbonylaminoheptanoylamino)benzothiazol-6-yl ester with N,N-diisopropylethylenediamine. The product is purified by chromatography on a Biotage column (8 g of silica), eluting with a 95/5 CH$_2$Cl$_2$/MeOH mixture to give 86 mg of product, i.e. a 44% yield.

EXAMPLE 52

Preparation of 4-(2-diisopropylaminoethylamino)benzenesulfonic acid 2-(7-aminoheptanoylamino)benzothiazol-6-yl ester hydrochloride

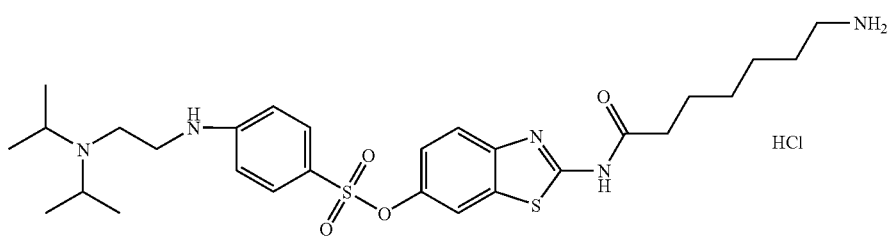

According to the method of Example 49, 4-(2-diisopropylaminoethylamino)-benzenesulfonic acid 2-(7-aminoheptanoylamino)benzothiazol-6-yl ester hydrochloride is prepared via hydrolysis of 4-(2-diisopropylaminoethylamino)-benzenesulfonic acid 2-(7-tert-butoxycarbonylaminoheptanoylamino)benzo-thiazol-6-yl in the presence of hydrochloric acid dissolved in EtOAc, to give 47 mg of hydrochloride i.e. a 77% yield.

EXAMPLE 53

Preparation of 4-(2-isopropylaminoethylamino)benzenesulfonic 2-(cyclopropanecarbonylamino)benzothiazol-6-yl ester hydrochloride

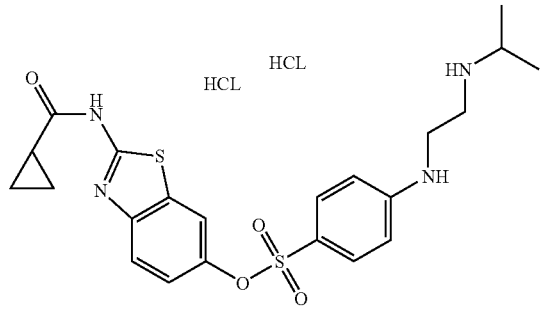

A solution of 4-fluorobenzenesulfonic 2-(cyclopropanecarbonylamino)benzo-thiazol-6-yl ester (example 53, brevetbenzothiazole_V2) (145 mg, 0.37 mmol) and N-isopropylethylenediamine (233 µl, 1.85 mmol) in 4.5 ml of NMP is heated at 150° C. by microwave for 5 minutes. The crude reaction product is diluted with EtOAc, washed 3 times with water and extracted twice with EtOAc. The organic phases are combined, dried over sodium sulfate, filtered and then evaporated to dryness. The 165 mg of crude product are purified by chromatography on silica: 8 g AIT column, eluent: 90/10/1 CH$_2$Cl$_2$/MeOH/—NH$_4$OH. The solid obtained (96 mg) is dissolved in EtOAc and then brought to pH 2 with hydrochloric acid dissolved in EtOAc. The suspension is evaporated to dryness and taken up in 5 ml of water, and then freeze-dried to give 76 mg of 4-(2-isopropylaminoethylamino)benzenesulfonic 2-(cyclo-propanecarbonylamino)benzothiazol-6-yl ester hydrochloride.

INTERMEDIATE 54

Preparation of 4-fluorobenzenesulfonic acid 2-isobutyryl-aminobenzothiazol-6-yl ester

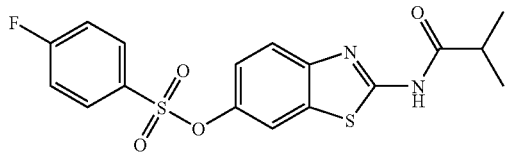

According to the method of intermediate 46, 4-fluorobenzenesulfonic acid 2-isobutyrylaminobenzothiazol-6-yl ester is prepared via the action of 4-fluorobenzenesulfonic acid 2-aminobenzothiazol-6-yl ester (intermediate 16, brevetbenzothiazole_V2) with isobutyric acid. The crude reaction product is crystallized from ethyl ether and, after filtering off by suction, 0.17 g of colorless solid is isolated, i.e. an 86% yield.

EXAMPLE 55

Preparation of 4-(2-diisopropylaminoethylamino)benzenesulfonic acid 2-isobutyrylaminobenzothiazol-6-yl ester hydrochloride

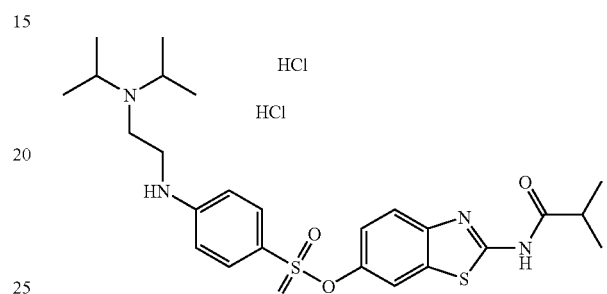

According to the method of Example 53, 2,4-(2-diisopropylaminoethylamino)-benzenesulfonic acid 2-isobutyrylaminobenzothiazol-6-yl ester hydrochloride is prepared via the action of 4-fluorobenzenesulfonic acid 2-isobutyrylamino-benzothiazol-6-yl ester with N,N-diisopropylethylenediamine. The crude reaction product is extracted with EtOAc and washed with water. The organic phase is dried over sodium sulfate, filtered and then evaporated: 0.327 g of crude product is obtained, which is chromatographed on a column of biotage silica (40 g), eluting with a 90/10 CH$_2$Cl$_2$/MeOH mixture. The oil obtained crystallizes from heptane. The product is redissolved in 5 ml of EtOAc and a solution of hydrochloric acid in EtOAc is then added dropwise to pH 2. The hydrochloride is filtered off by suction, washed with EtOAc and then dried under vacuum at 40° C. 0.112 g of 4-(2-diisopropylaminoethylamino)benzene-sulfonic acid 2-isobutyrylaminobenzothiazol-6-yl ester hydrochloride is isolated, i.e. a 42% yield.

INTERMEDIATE 56

Preparation of 4-fluorobenzenesulfonic acid 2-propionyl-aminobenzothiazol-6-yl ester

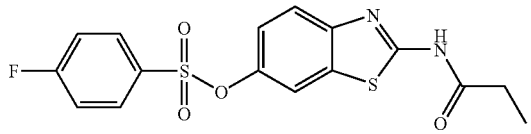

According to the method of intermediate 46, 4-fluorobenzenesulfonic acid 2-propionylaminobenzothiazol-6-yl ester is prepared via the action of 4-fluorobenzenesulfonic acid 2-aminobenzothiazol-6-yl ester (intermediate 16, brevetbenzothiazole_V2) with propionic acid. The product, 0.397 g, is obtained in a yield of 93%.

EXAMPLE 57

Preparation of 4-(2-diisopropylaminoethylamino)benzenesulfonic acid 2-propionylaminobenzothiazol-6-yl ester hydrochloride

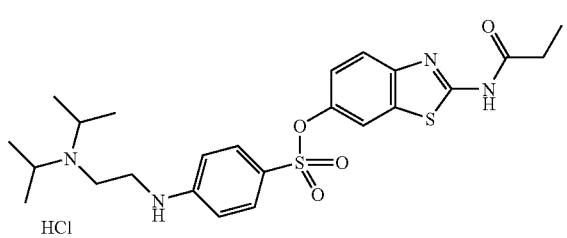

According to the method of example 53, 4-(2-diisopropylaminoethylamino)-benzenesulfonic acid 2-propionylaminobenzothiazol-6-yl ester is prepared via the action of 4-fluorobenzenesulfonic acid 2-propionylaminobenzothiazol-6-yl ester with N,N-diisopropylethylenediamine by heating for 10 minutes by microwave at 150° C. The product, 0.09 g, is obtained after purification in a yield of 45%, in the form of the hydrochloride.

EXAMPLE 58

Preparation of 4-(2-hydroxy-2-methylpropylamino)benzene-sulfonic acid 2-propionylaminobenzothiazol-6-yl ester

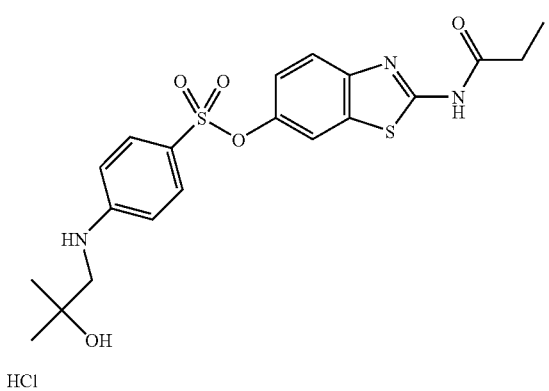

According to the method of example 53, 4-(2-hydroxy-2-methylpropylamino)-benzenesulfonic acid 2-propionylaminobenzothiazol-6-yl ester is prepared via the action of 4-fluorobenzenesulfonic acid 2-propionylaminobenzothiazol-6-yl ester with 1-amino-2-methylpropan-2-ol by heating for 20 minutes by microwave at 150° C. The product, 0.096 g, is obtained after purification in a yield of 50%, in the form of the hydrochloride.

INTERMEDIATE 59

4-Fluorobenzenesulfonic acid 2-(cyclobutanecarbonyl-amino)benzothiazol-6-yl ester

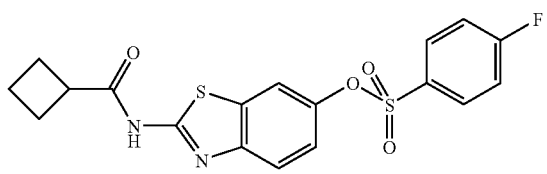

According to the method of intermediate 46, 4-fluorobenzenesulfonic acid 2-(cyclobutanecarbonylamino)benzothiazol-6-yl ester is prepared via the action of 4-fluorobenzenesulfonic acid 2-aminobenzothiazol-6-yl ester with cyclobutanecarboxylic acid.

EXAMPLE 60

Preparation of 4-(2-diisopropylaminoethylamino)benzenesulfonic acid 2-(cyclobutanecarbonylamino)benzothiazol-6-yl ester hydrochloride

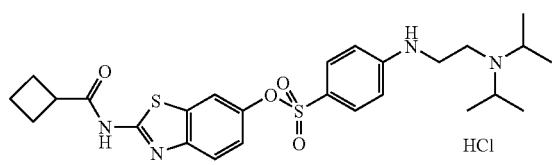

According to the method of example 53, 4-(2-diisopropylaminoethylamino)-benzenesulfonic acid 2-(cyclobutanecarbonylamino)benzothiazol-6-yl ester is prepared via the action of 4-fluorobenzenesulfonic acid 2-propionylamino-benzothiazol-6-yl ester with N,N-diisopropylethylenediamine by heating for 10 minutes by microwave at 150° C. The product, 0.054 g, is obtained after purification in a yield of 18%, in the form of the hydrochloride.

INTERMEDIATE 61

Preparation of 4-fluorobenzenesulfonic acid 2-(3-pyrid-3-yl-propionylamino)benzothiazol-6-yl ester.

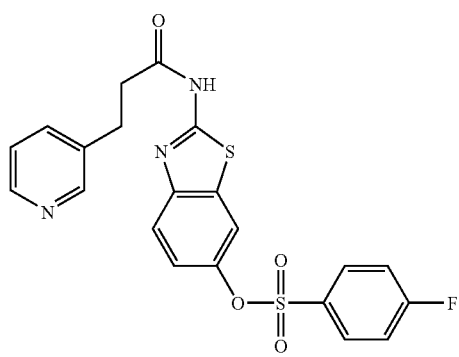

According to the method of intermediate 46, 4-fluorobenzenesulfonic acid 2-(3-pyrid-3-ylpropionylamino)benzothiazol-6-yl ester is prepared via the is action of 4-fluorobenzenesulfonic acid 2-aminobenzothiazol-6-yl ester with 3-(3-pyridyl)propionic acid. The product is obtained in a quantitative yield.

EXAMPLE 62

Preparation of 4-(2-diisopropylaminoethylamino) benzenesulfonic acid 2-(3-pyrid-3-ylpropionylamino)benzothiazol-6-yl ester hydrochloride

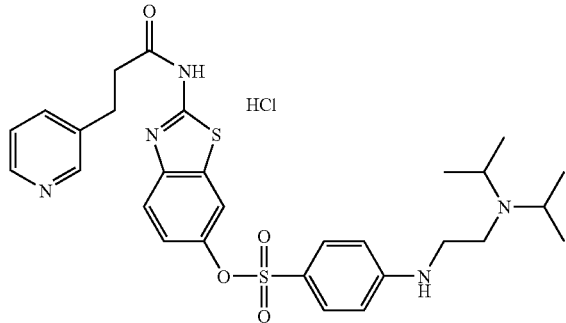

According to the method of example 7, 4-(2-diisopropylaminoethylamino)-benzenesulfonic acid 2-(3-pyrid-3-yl-propionylamino)benzothiazol-6-yl ester is prepared via the action of 4-fluorobenzenesulfonic acid 2-(3-pyrid-3-yl-propionylamino)benzothiazol-6-yl ester with N,N-diisopropyl-ethylenediamine by heating for 10 minutes by microwave at 150° C. The product, 0.045 g, is obtained after purification in a yield of 23% in the form of the hydrochloride.

EXAMPLE 63

Preparation of 4-(2-hydroxy-2-methylpropylamino) benzene-sulfonic acid 2-(3-pyrid-3-ylpropionylamino)benzothiazol-6-yl ester hydro-chloride

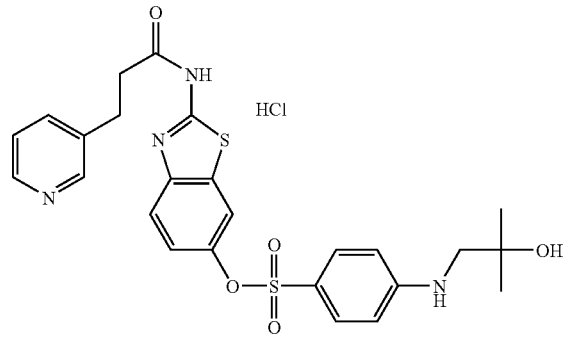

According to the method of example 53, 4-(2-hydroxy-2-methylpropyl-amino)benzenesulfonic acid 2-(3-pyrid-3-yl-propionylamino)benzothiazol-6-yl ester is prepared via the action of 4-fluorobenzenesulfonic acid 2-(3-pyrid-3-yl-propionylamino)benzothiazol-6-yl ester with 1-amino-2-methylpropan-2-ol by heating for 20 minutes by microwave at 150° C. The product, 0.104 g, is obtained after purification in a yield of 52%, in the form of the hydrochloride.

INTERMEDIATE 64

Preparation of 4-fluorobenzenesulfonic acid 2-acetylamino-benzothiazol-6-yl ester

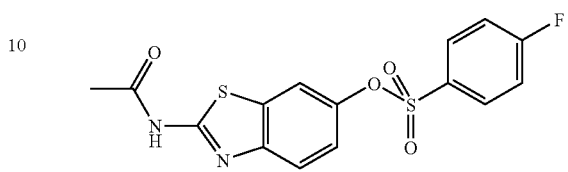

A solution of 4-fluorobenzenesulfonic acid 2-aminobenzothiazol-6-yl ester (intermediate 16) (101.2 mg, 0.312 mmol), acetic acid (56.2 mg, 0.936 mmol), HBTU (355 mg, 0.936 mmol) and N,N-diisopropylamine (326 µl, 1.872 mmol) in 5 ml of dimethylformamide in a test tube, equipped with a magnetic bar, is stirred for 20 hours at room temperature. 100 ml of water are added and the reaction medium is extracted with ethyl acetate. The organic phase is dried over magnesium sulfate and evaporated. The residue obtained is taken up in ethyl acetate and purified on a Varian flash cartridge containing 5 g of silica of porosity 15-35µ, with a mixture of 1% methanol in dichloromethane. After evaporating off the solvent, 66 mg of 4-fluorobenzenesulfonic acid 2-acetylaminobenzothiazol-6-yl ester are obtained (yellow oil) in a yield of 58%. LC/MS (method A1): [M+H]+: 367.14, retention time: 3.50 min.

EXAMPLE 65

Preparation of 4-(2-isopropylaminoethylamino)benzenesulfonic acid 2-acetylaminobenzothiazol-6-yl ester

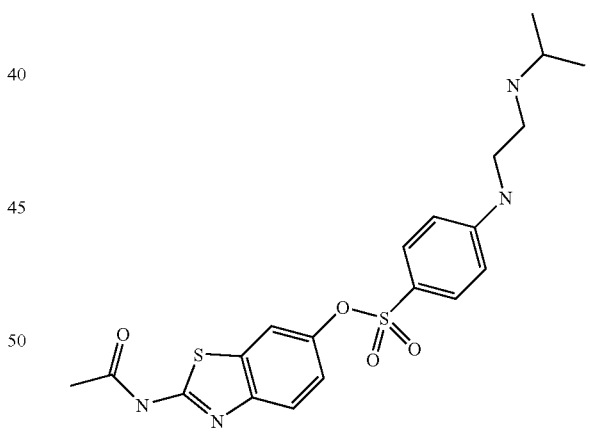

A solution of 4-fluorobenzenesulfonic acid 2-acetylaminobenzothiazol-6-yl ester (intermediate 64) (66 mg, 0.180 mmol), N-isopropylethylenediamine (55.2 mg, 0.540 mmol) and cesium carbonate (58.6 mg, 0.180 mmol) in 2 ml of dimethyl sulfoxide in a test tube, equipped with a magnetic bar, is stirred overnight at 80° C. 100 ml of water are added and the reaction medium is extracted with ethyl acetate. The organic phase is then washed with water, dried over magnesium sulfate and evaporated. The residue, purified by LC/MS, gives 43 mg of 4-(2-isopropylaminoethylamino)benzenesulfonic acid 2-acetylaminobenzothiazol-6-yl ester (white powder) in a yield of 53%.

LC/MS (method A1): [M+H]+: 449.35, retention time: 3.28 min.

1H NMR spectrum at 300 MHz on a Bruker Avance DPX-300 spectrometer with the chemical shifts (δ in ppm)—in the solvent dimethyl sulfoxide-d6 (DMSO-d$_6$) referenced to 2.50 ppm:

Strong presumption for the product salified with TFA with:

1.21 (d, J=7.0 Hz, 6H); 2.20 (s, 3H); 3.07 (m, 2H); from 3.20 to 3.35 (masked m, 1H); 3.41 (m, 2H); 6.72 (broad d, J=8.5 Hz, 2H); 6.93 (broad t, J=6.0 Hz, 1H); 7.01 (dd, J=2.5 and 8.5 Hz, 1H); 7.53 (broad d, J=8.5 Hz, 2H); 7.68 (d, J=8.5 Hz, 1H); 7.69 (d, J=2.5 Hz, 1H); 8.30 (broad m, 2H); 12.4 (broad s, 1H).

INTERMEDIATE 66

Preparation of 4-fluorobenzenesulfonic acid 2-(2-methoxy-acetylamino)benzothiazol-6-yl ester

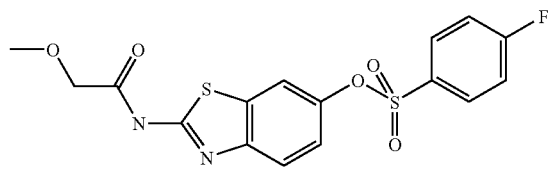

A solution of 4-fluorobenzenesulfonic acid 2-aminobenzothiazol-6-yl ester (intermediate 16) (101.2 mg, 0.312 mmol), methoxyacetic acid (84.3 mg, 0.936 mmol), HBTU (355 mg, 0.936 mmol) and N,N-diisopropylamine (326 μl, 1.872 mmol) in 5 ml of dimethylformamide in a test tube, equipped with a magnetic bar, is stirred for 20 hours at room temperature. 100 ml of water are added and the reaction medium is extracted with ethyl acetate. The organic phase is dried over magnesium sulfate and evaporated. The residue obtained is taken up in ethyl acetate and purified on a Varian flash cartridge containing 5 g of silica of porosity 15-35μ, with a mixture of 1% methanol in dichloro-methane. After evaporating off the solvent, 89 mg of 4-fluorobenzenesulfonic acid 2-but-3-enoylaminobenzothiazol-6-yl ester are obtained (yellow oil) in a yield of 72%. LC/MS (method A1): [M+H]+: 397.11, retention time: 3.59 min.

EXAMPLE 67

Preparation of 4-(2-isopropylaminoethylamino)benzenesulfonic acid 2-(2-methoxyacetylamino)benzothiazol-6-yl ester

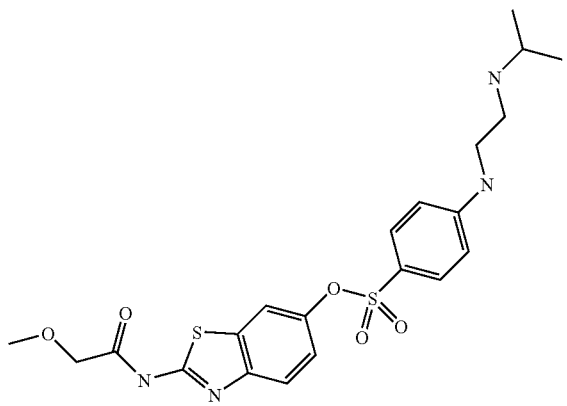

A solution of 4-(2-isopropylaminoethylamino)benzenesulfonic acid 2-(2-methoxyacetylamino)benzothiazol-6-yl ester (intermediate 66) (89 mg, 0.224 mmol), N-isopropylethylenediamine (68.7 mg, 0.672 mmol) and cesium carbonate (73 mg, 0.224 mmol) in 2 ml of dimethyl sulfoxide in a test tube, equipped with a magnetic bar, is stirred overnight at 80° C. 100 ml of water are added and the reaction medium is extracted with ethyl acetate. The organic phase is then washed with water, dried over magnesium sulfate and evaporated. The residue, purified by LC/MS, gives 46.6 mg of 4-(2-isopropylaminoethylamino)benzenesulfonic acid 2-(2-methoxyacetylamino)-benzothiazol-6-yl ester (white powder) in a yield of 43%.

LC/MS (method A1): [M+H]+: 479.35, retention time: 3.33 min.

1H NMR spectrum at 300 MHz on a Bruker Avance DPX-300 spectrometer with the chemical shifts (δ in ppm)—in the solvent dimethyl sulfoxide-d$_6$ (DMSO-d$_6$) referenced to 2.50 ppm:

Strong presumption for the product salified with TFA with:

1.21 (d, J=7.0 Hz, 6H); 3.07 (broad t, J=6.5 Hz, 2H); from 3.15 to 3.35 (masked m, 1H); 3.38 (s, 3H); 3.41 (m, 2H); 4.20 (s, 2H); 6.72 (broad d, J=8.5 Hz, 2H); 6.93 (broad t, J=6.0 Hz, 1H); 7.03 (dd, J=2.5 and 8.5 Hz, 1H); 7.53 (broad d, J=8.5 Hz, 2H); 7.69 (d, J=8.5 Hz, 1H); 7.71 (d, J=2.5 Hz, 1H); from 8.10 to 8.45 (broad m, 2H); from 12.0 to 12.5 (very broad m, 1H).

INTERMEDIATE 68

Preparation of 4-fluorobenzenesulfonic acid 2-(cyclopentane carbonylamino)benzothiazol-6-yl ester

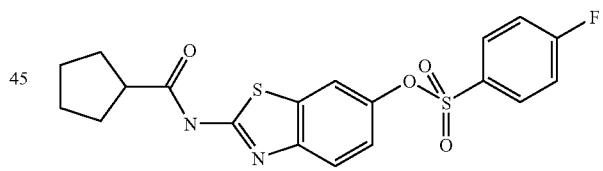

A solution of 4-fluorobenzenesulfonic acid 2-aminobenzothiazol-6-yl ester (intermediate 16) (101.2 mg, 0.312 mmol), cyclopentanecarboxylic acid (53.4 mg, 0.936 mmol), HBTU (355 mg, 0.936 mmol) and N,N-diisopropyl-amine (326 μl, 1.872 mmol) in 5 ml of dimethylformamide in a test tube, equipped with a magnetic bar, is stirred for 20 hours at room temperature. 100 ml of water are added and the reaction medium is extracted with ethyl acetate. The organic phase is dried over magnesium sulfate and evaporated. The residue obtained is taken up in ethyl acetate and purified on a Varian flash cartridge containing 5 g of silica of porosity 15-35μ, with a mixture of 1% methanol in dichloromethane. After evaporating off the solvent, 90 mg of 4-fluorobenzenesulfonic acid 2-(cyclopentane carbonylamino)benzothiazol-6-yl ester are obtained (yellow oil) in a yield of 68%. LC/MS (method A1): [M+H]+: 421.13, retention time: 4.05 min.

EXAMPLE 69

Preparation of
4-(2-isopropylaminoethylamino)benzenesulfonic acid
2-(cyclopentanecarbonylamino)benzothiazol-6-yl ester

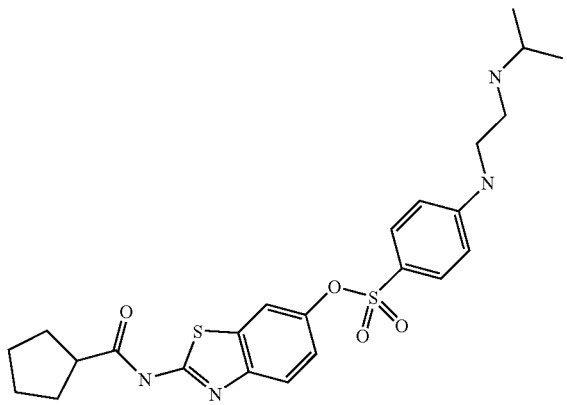

A solution of 4-fluorobenzenesulfonic acid 2-(2-methoxyacetylamino)-benzothiazol-6-yl ester (intermediate 68) (90 mg, 0.214 mmol), N-isopropylethylenediamine (65.6 mg, 0.642 mmol) and cesium carbonate (69.7 mg, 0.214 mmol) in 2 ml of dimethyl sulfoxide in a test tube, equipped with a magnetic bar, is stirred overnight at 80° C. 100 ml of water are added and the reaction medium is extracted with ethyl acetate. The organic phase is then washed with water, dried over magnesium sulfate and evaporated. The residue, purified by LC/MS, gives 26.2 mg of 4-(2-isopropylaminoethylamino)benzenesulfonic acid 2-(cyclopentanecarbonylamino)benzothiazol-6-yl ester (white powder) in a yield of 24%.

LC/MS (method A1): [M+H]+: 503.39, retention time: 3.68 min.

1H NMR spectrum at 300 MHz on a Bruker Avance DPX-300 spectrometer with the chemical shifts (δ in ppm)—in the solvent dimethyl sulfoxide-d6 (DMSO-d$_6$) referenced to 2.50 ppm:

Strong presumption for the product salified with TFA with:

1.21 (d, J=7.0 Hz, 6H); from 1.50 to 1.80 (m, 6H); from 1.82 to 1.98 (m, 2H); 2.98 (m, 1H); 3.04 (m, 2H); from 3.15 to 3.55 (m, 3H); 6.71 (broad d, J=8.5 Hz, 2H); 6.92 (broad t, J=6.0 Hz, 1H); 7.02 (dd, J=2.5 and 8.5 Hz, 1H); 7.53 (broad d, J=8.5 Hz, 2H); from 7.65 to 7.70 (m, 2H); from 8.05 to 8.45 (very broad m, 2H); 12.4 (broad m, 1H).

INTERMEDIATE 70

Preparation of 4-fluorobenzenesulfonic acid 2-propionylaminobenzothiazol-6-yl ester

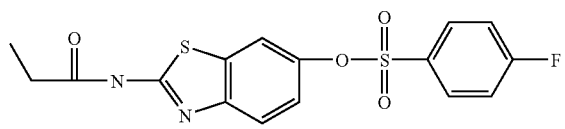

A solution of 4-fluorobenzenesulfonic acid 2-aminobenzothiazol-6-yl ester (intermediate 16) (500 mg, 1.14 mmol), propionic acid (253 mg, 3.42 mmol), HBTU (1.23 g, 3.42 mmol) and N,N-diisopropylamine (737 mg, 5.7 mmol) in 6.5 ml of dimethylformamide is stirred overnight at room temperature. The reaction medium is evaporated to dryness. The dry residue is extracted twice with 50 ml of ethyl acetate and washed with water. The organic phase is then washed with saturated sodium chloride solution. The organic phase is dried over magnesium sulfate and then evaporated. The oil obtained is dissolved in 35 ml of dimethyl sulfoxide and then purified 7 times by preparative HPLC on a Nucléodur C18, 100'10 μm reverse-phase column with a gradient over 52 minutes of 5% to 95% acetonitrile supplemented with 0.07% trifluoroacetic acid in water, supplemented with 0.07% trifluoroacetic acid. The flow rate is 70 ml/min. The fractions containing the clean product are concentrated to give 300 mg of 4-fluorobenzenesulfonic acid 2-propionylaminobenzothiazol-6-yl ester in a yield of 69%.

NMR: 1H NMR spectrum at 300 MHz on a Bruker Avance DPX-300 spectrometer with the chemical shifts (δ in ppm)—in the solvent dimethyl sulfoxide-d$_6$ (DMSO-d$_6$) referenced to 2.50 ppm:

1.11 (t, J=7.5 Hz, 3H); 2.50 (partially masked m, 2H); 7.01 (dd, J=2.5 and 8.5 Hz, 1H); 7.51 (broad t, J=9.0 Hz, 2H); 7.68 (d, J=8.5 Hz, 1H); 7.79 (d, J=2.5 Hz, 1H); 7.94 (broad dd, J=5.5 and 9.0 Hz, 2H); 12.4 (broad s, 1H).

EXAMPLE 71

Preparation of
4-(2-isopropylaminoethylamino)benzenesulfonic acid 2-propionylaminobenzothiazol-6-yl ester;
compound with trifluoroacetic

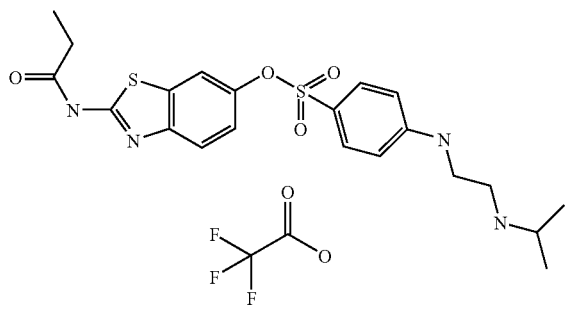

A solution of 4-fluorobenzenesulfonic acid 2-propionylaminobenzothiazol-6-yl acid ester (intermediate 70) (300 mg, 0.789 mmol), N-isopropylethylenediamine (242 mg, 2.37 mmol) and cesium carbonate (256 mg, 0.789 mmol) in 4 ml of dimethyl sulfoxide is maintained at 80° C. with stirring for 7 hours 30 minutes, and then at room temperature for 2 days. The reaction medium is filtered and rinsed with 8 ml of dimethyl sulfoxide. The expected product is purified 3 times by preparative HPLC under the same conditions as for intermediate 70. 205 mg of 4-(2-isopropylaminoethylamino)benzenesulfonic acid 2-propionylaminobenzothiazol-6-yl ester; compound with trifluoroacetic acid, are obtained in a yield of 56%.

NMR: 1H NMR spectrum at 300 MHz on a Bruker Avance DPX-300 spectrometer with the chemical shifts (δ in ppm)—in the solvent dimethyl sulfoxide-d$_6$ (DMSO-d$_6$) referenced to 2.50 ppm:

1.11 (t, J=7.5 Hz, 3H); 1.22 (d, J=6.5 Hz, 6H); from 2.45 to 2.54 (partially masked m, 2H); 3.07 (m, 2H); from 3.22 to 3.47 (partially masked m, 3H); 6.72 (broad d, J=9.0 Hz, 2H); 6.93 (broad t, J=6.0 Hz, 1H); 7.02 (dd, J=2.5 and 8.5 Hz, 1H);

7.53 (broad d, J=9.0 Hz, 2H); 7.67 (d, J=8.5 Hz, 1H); 7.69 (d, J=2.5 Hz, 1H); from 8.22 to 8.38 (broad m, 2H); 12.35 (broad s, 1H).

INTERMEDIATE 72

Preparation of 4-fluorobenzenesulfonic acid 2-butyrylamino-benzothiazol-6-yl ester

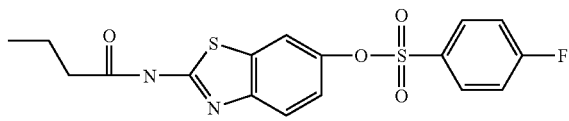

According to the method for intermediate 70, intermediate 72 is synthesized using butyric acid. 80 mg of 4-fluorobenzenesulfonic acid 2-butyrylamino-benzothiazol-6-yl ester are obtained in a yield of 18%.

NMR: 1H NMR spectrum at 300 MHz on a Bruker Avance DPX-300 spectrometer with the chemical shifts (δ in ppm)— in the solvent dimethyl sulfoxide-$d_6$ (DMSO-$d_6$) referenced to 2.50 ppm:

0.92 (t, J=7.5 Hz, 3H); 1.64 (m, 2H); 2.48 (partially masked m, 2H); 7.01 (dd, J=2.5 and 8.5 Hz, 1H); 7.51 (broad t, J=9.0 Hz, 2H); 7.68 (d, J=8.5 Hz, 1H); 7.78 (d, J=2.5 Hz, 1H); 7.93 (broad dd, J=5.5 and 9.0 Hz, 2H); 12.4 (broad s, 1H).

EXAMPLE 73

Preparation of 4-(2-isopropylaminoethylamino)benzenesulfonic acid 2-butyrylaminobenzothiazol-6-yl ester; compound with trifluoroacetic acid

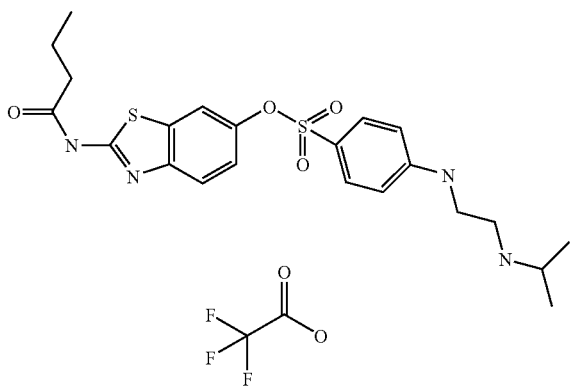

According to the method of example 71, example 73 is obtained using intermediate 72 with N-isopropylethylenediamine. 37 mg of 4-(2-isopropylaminoethylamino)benzenesulfonic acid 2-butyrylaminobenzothiazol-6-yl ester; compound with trifluoroacetic acid, are obtained in a yield of 36%.

NMR: 1H NMR spectrum at 300 MHz on a Bruker Avance DPX-300 spectrometer with the chemical shifts (δ in ppm)— in the solvent dimethyl sulfoxide-$d_6$ (DMSO-$d_6$) referenced to 2.50 ppm:

0.91 (t, J=7.5 Hz, 3H); 1.22 (d, J=6.5 Hz, 6H); 1.63 (m, 2H); 2.47 (partially masked t, J=7.5 Hz, 2H); 3.07 (m, 2H); from 3.20 to 3.37 (masked m, 1H); 3.41 (m, 2H); 6.72 (broad d, J=9.0 Hz, 2H); 6.94 (broad t, J=6.0 Hz, 1H); 7.02 (dd, J=2.5 and 8.5 Hz, 1H); 7.53 (broad d, J=9.0 Hz, 2H); 7.66 (d, J=8.5 Hz, 1H); 7.69 (d, J=2.5 Hz, 1H); 8.32 (broad m, 2H); 12.4 (broad s, 1H).

INTERMEDIATE 74

Preparation of 4-fluorobenzenesulfonic acid 2-isobutyryl-aminobenzothiazol-6-yl ester

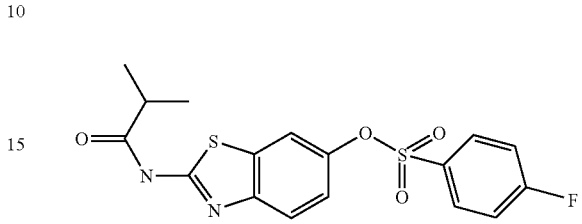

According to the method for intermediate 70, intermediate 74 is synthesized using isobutyric acid. 75 mg of 4-fluorobenzenesulfonic acid 2-isobutyryl-aminobenzothiazol-6-yl ester are obtained in a yield of 17%.

NMR: 1H NMR spectrum at 300 MHz on a Bruker Avance DPX-300 spectrometer with the chemical shifts (δ in ppm)— in the solvent dimethyl sulfoxide-d6 (DMSO-$d_6$) referenced to 2.50 ppm:

1.14 (d, J=7.0 Hz, 6H); 2.79 (m, 1H); 7.02 (dd, J=2.5 and 8.5 Hz, 1H); 7.51 (broad t, J=9.0 Hz, 2H); 7.68 (d, J=8.5 Hz, 1H); 7.79 (d, J=2.5 Hz, 1H); 7.93 (broad dd, J=5.5 and 9.0 Hz, 2H); 12.4 (broad s, 1H).

EXAMPLE 75

Preparation of 4-(2-isopropylaminoethylamino)benzenesulfonic acid 2-isobutyrylaminobenzothiazol-6-yl ester; compound with trifluoroacetic acid

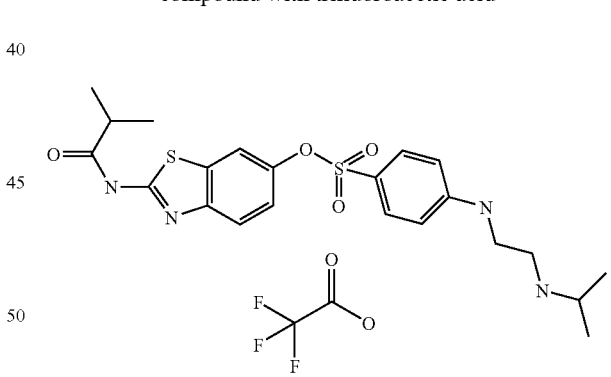

According to the method of example 71, example 75 is obtained using intermediate 74 with N-isopropylethylenediamine. 49 mg of 4-(2-isopropyl-aminoethylamino)benzenesulfonic acid 2-isobutyrylaminobenzothiazol-6-yl ester; compound with trifluoroacetic acid, are obtained in a yield of 44%.

NMR: 1H NMR spectrum at 300 MHz on a Bruker Avance DPX-300 spectrometer with the chemical shifts (δ in ppm)— in the solvent dimethyl sulfoxide-d6 (DMSO-$d_6$) referenced to 2.50 ppm:

1.14 (d, J=6.5 Hz, 6H); 1.22 (d, J=6.5 Hz, 6H); 2.79 (m, 1H); 3.07 (m, 2H); from 3.25 to 3.37 (masked m, 1H); 3.41 (m, 2H); 6.72 (broad d, J=9.0 Hz, 2H); 6.93 (broad t, J=6.0 Hz, 1H); 7.03 (dd, J=2.5 and 8.5 Hz, 1H); 7.53 (broad d, J=9.0 Hz, 2H); from 7.64 to 7.70 (m, 2H); 8.30 (broad m, 2H); 12.4 (broad s, 1H).

INTERMEDIATE 76

Preparation of 4-fluorobenzenesulfonic acid 2-(cyclobutane-carbonylamino)benzothiazol-6-yl ester

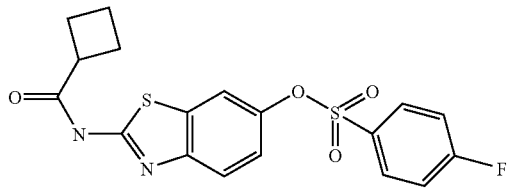

According to the method for intermediate 70, intermediate 76 is synthesized using cyclobutanecarboxylic acid. 185 mg of fluorobenzenesulfonic acid 2-(cyclobutanecarbonylamino)benzothiazol-6-yl ester are obtained in a yield of 40%.

EXAMPLE 77

Preparation of 4-(2-isopropylaminoethylamino)benzenesulfonic acid (2-cyclobutanecarbonylamino)benzothiazol-6-yl ester; compound with trifluoroacetic acid

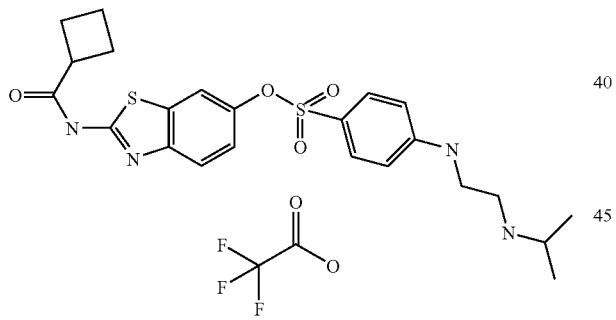

According to the method of example 71, example 77 is obtained using intermediate 76, with N-isopropylethylenediamine. 41 mg of 4-(2-isopropyl-aminoethylamino)benzenesulfonic acid (2-cyclobutanecarbonylamino)benzo-thiazol-6-yl ester; compound with trifluoroacetic acid are obtained in a yield of 37%.

NMR: 1H NMR spectrum at 300 MHz on a Bruker Avance DPX-300 spectrometer with the chemical shifts (δ in ppm)—in the solvent dimethyl sulfoxide-$d_6$ (DMSO-$d_6$) referenced to 2.50 ppm:

1.22 (d, J=6.5 Hz, 6H); 1.84 (m, 1H); 1.99 (m, 1H); from 2.10 to 2.30 (m, 4H); 3.07 (m, 2H); from 3.20 to 3.47 (masked m, 4H); 6.72 (broad d, J=9.0 Hz, 2H); 6.97 (broad t, J=6.0 Hz, 1H); 7.01 (dd, J=2.5 and 8.5 Hz, 1H); 7.53 (broad d, J=9.0 Hz, 2H); 7.67 (d, J=8.5 Hz, 1H); 7.69 (d, J=2.5 Hz, 1H); from 8.27 to 8.44 (broad m, 2H); 12.3 (broad s, 1H).

INTERMEDIATE 78

Preparation of 4-fluorobenzenesulfonic acid 2-butyrylamino-benzothiazol-6-yl ester

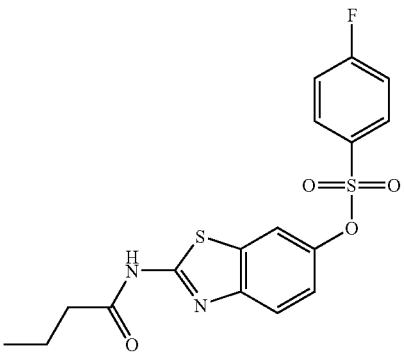

A solution of 4-fluorobenzenesulfonic acid 2-aminobenzothiazol-6-yl ester (intermediate 16) (359 mg, 1.107 mmol), butyric acid (146 mg, 1.66 mmol), HATU (631 mg, 1.66 mmol) and N,N-diisopropylethylamine (0.286 ml, 1.66 mmol) in 5.5 ml of dimethylformamide in a 20 ml round-bottomed flask, equipped with a magnetic bar, is stirred for 8 hours at 60° C. and then left overnight at room temperature. The reaction medium is extracted with ethyl acetate and washed with water and then with 0.1 N hydrochloric acid solution. The organic phase is dried over magnesium sulfate, filtered and then evaporated to dryness. The residue obtained (567 mg of pale yellow solid) is purified by chromatography on a 40 g Biotage silica cartridge, eluting with a 9/1 toluene/isopropanol mixture. After evaporating off the solvent, 239 mg of 4-fluorobenzenesulfonic acid 2-butyrylaminobenzothiazol-6-yl ester are obtained (white solid) in a yield of 55%.

Mass:
LC/MS: m/z 395: [M+H]⁺, m/z 393: [M−H]⁻

1H NMR spectrum at 400 MHz with the chemical shifts (δ in ppm)—in the solvent dimethyl sulfoxide-$d_6$ (DMSO-$d_6$) referenced to 2.50 ppm:

0.9 ns 1 (t, J=7.5 Hz, 3H); 1.64 (m, 2H); 2.47 (partially masked t, J=7.5 Hz, 2H); 7.01 (dd, J=2.5 and 8.5 Hz, 1H); 7.51 (broad t, J=9.0 Hz, 2H); 7.68 (d, J=8.5 Hz, 1H); 7.79 (d, J=2.5 Hz, 1H); 7.93 (dd, J=6.0 and 9.0 Hz, 2H); 12.4 (broad s, 1H).

EXAMPLE 79

Preparation of 4-(2-diisopropylaminoethylamino)benzenesulfonic acid 2-butyrylaminobenzothiazol-6-yl ester hydrochloride

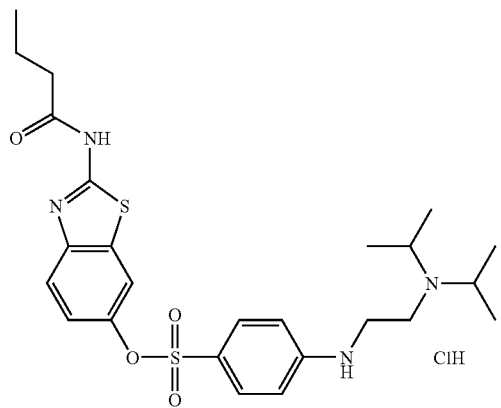

A solution of 4-fluorobenzenesulfonic acid 2-butyrylaminobenzothiazol-6-yl ester (intermediate 78) (100 mg, 0.2 mmol) and N,N-diisopropylethylene-diamine (185 µl, 1.01 mmol) in 3 ml of N-methylpyrrolidone in a 5 ml microwave vial, equipped with a magnetic bar, is heated for 10 minutes at 150° C. by microwave. The reaction medium is extracted with ethyl acetate and washed with water. The organic phase is dried over magnesium sulfate, filtered and then evaporated to dryness. The residue obtained is purified by chromatography on Merck silica (40-63 µm). After evaporating off the solvent, 41 mg of a colorless oil (crystallizes when dry) are obtained. The product is dissolved in a minimum amount of ethyl acetate, and 4 N hydrochloric acid as a solution in dioxane is then added. The medium precipitates, and is concentrated, taken up in water and then filtered through a Milex 45 µm filter. The solution precipitates, and 31 mg (28% yield) of 4-(2-diisopropylamino-ethylamino)benzenesulfonic acid 2-butyrylaminobenzothiazol-6-yl ester hydrochloride are obtained after vacuum filtration and then drying under vacuum at 40° C.

Mass:
IE: m/z 114: $(C_3H_7)_2NCH2^+$ (base peak) absence of the molecular ion.
IC: m/z 519 $[M+H]^+$ (base peak).
LC/MS: m/z 519 $[M+H]^+$, m/z 517: $[M-H]^-$
H NMR spectrum at 300 MHz with the chemical shifts ($\delta$ in ppm)—in the solvent dimethyl sulfoxide-$d_6$ (DMSO-$d_6$) referenced to 2.50 ppm:
0.91 (t, J=7.5 Hz, 3H); from 1.20 to 1.32 (broad m, 12H); 1.63 (m, 2H); from 2.42 to 2.55 (partially masked t, J=7.5 Hz, 2H); 3.19 (m, 2H); 3.51 (m, 2H); 3.69 (broad m, 2H); 6.72 (broad d, J=9.0 Hz, 2H); 6.97 (broad t, J=6.0 Hz, 1H); 7.02 (dd, J=2.5 and 8.5 Hz, 1H); 7.53 (broad d, J=9.0 Hz, 2H); from 7.63 to 7.69 (m, 2H); 8.78 (broad m, 1H); 12.4 (broad s, 1H).

EXAMPLE 80

Preparation of 4-(2-hydroxy-2-methylpropylamino)benzene-sulfonic acid 2-butyrylaminobenzothiazol-6-yl ester hydrochloride

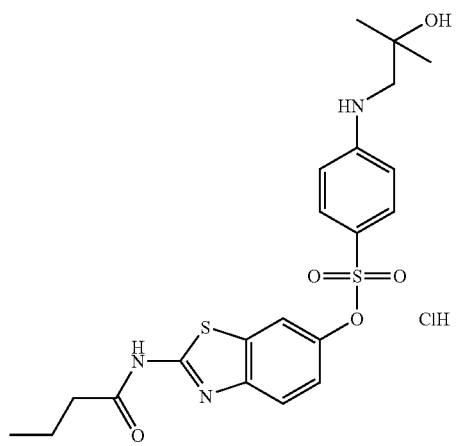

A solution of 4-fluorobenzenesulfonic acid 2-butyrylaminobenzothiazol-6-yl ester (intermediate 78) (135 mg, 0.34 mmol) and 1-amino-2-methylpropan-2-ol (153 mg, 1.718 mmol) in 3 ml of N-methylpyrrolidone in a 5 ml microwave vial, equipped with a magnetic bar, is heated for 20 minutes at 150° C. by microwave. The reaction medium is extracted with ethyl acetate (3×20 ml) and washed with water (4×25 ml). The organic phase is dried over magnesium sulfate, filtered and then evaporated to dryness. The residue obtained is purified by chromatography on silica, on an 8 g 15-35 µm AIT column, eluting with a 9/1 ethyl acetate/cyclohexane mixture. After evaporating off the solvent, 55 mg of a colorless solid are obtained. The product is dissolved in a minimum amount of dioxane, and 4 N hydrochloric acid dissolved in dioxane is added. The precipitate obtained is filtered off by suction, washed with dioxane and then dried under vacuum at 40° C. to give 42 mg of 4-(2-hydroxy-2-methylpropylamino)benzenesulfonic acid 2-butyrylaminobenzothiazol-6-yl ester hydrochloride, i.e. a yield of 25%.

Mass:
IE: m/z 463: $[M^{+-}]$, m/z 228: $[M^{+-}]$-SO2PhNCH2$C_3H_{70}$
IC: m/z 464: $[M+H]^+$
LC/MS: m/z 464: $[M+H]^+$, m/z 462: $[M-H]^-$
1H NMR spectrum at 400 MHz ($\delta$ in ppm)—in the solvent dimethyl sulfoxide-$d_6$ (DMSO-d6) referenced to 2.50 ppm:
0.93 (t, J=7.5 Hz, 3H); 1.15 (s, 6H); 1.66 (m, 2H); from 2.46 to 2.59 (partially masked m, 2H); 3.04 (s, 2H); 6.76 (broad d, J=9.0 Hz, 2H); 6.98 (dd, J=2.5 and 8.5 Hz, 1H); 7.42 (broad d, J=9.0 Hz, 2H); 7.66 (d, J=8.5 Hz, 1H); 7.70 (d, J=2.5 Hz, 1H); 12.4 (broad s, 1H).

INTERMEDIATE 81

Preparation of 4-(2-hydroxy-2-methylpropylamino)benzene-sulfonic acid 2-tert-butoxycarbonylaminobenzothiazol-6-yl ester

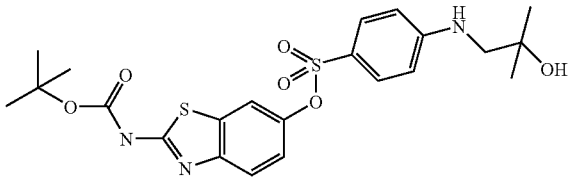

A solution of 4-fluorobenzenesulfonic acid 2-tert-butoxycarbonylaminobenzo-thiazol-6-yl ester (intermediate 15) (300 mg, 0.707 mmol), cesium carbonate (230 mg, 0.707 mmol) and 1-amino-2-methylpropan-2-ol (126 mg, 1.414 mmol) in 5 ml of dimethyl sulfoxide is stirred at 80° C. for 72 hours. Water is added to the reaction medium, and the mixture is extracted 3 times with ethyl acetate. The organic phase is washed with saturated sodium chloride solution and then dried over magnesium sulfate and finally evaporated to dryness to give 290 mg of 4-(2-hydroxy-2-methylpropylamino)benzenesulfonic acid 2-tert-butoxycarbonylaminobenzo-thiazol-6-yl ester in a yield of 83%.

INTERMEDIATE 82

Preparation of 4-(2-hydroxy-2-methylpropylamino)benzene-sulfonic acid 2-aminobenzothiazol-6-yl ester; compound with trifluoroacetic acid

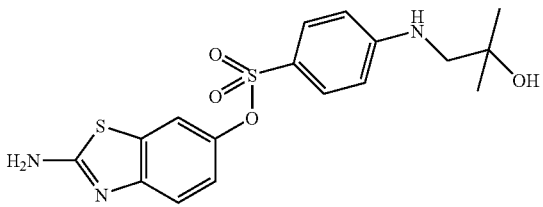

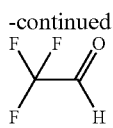

A solution of 4-(2-hydroxy-2-methylpropylamino)benzenesulfonic acid 2-tert-butoxycarbonylaminobenzothiazol-6-yl ester (intermediate 81) (170 mg, 0.344 mmol) and trifluoroacetic acid (14.9 g, 130.7 mmol) in 10 ml of dichloromethane and 100 µl of water is stirred for 2 hours at room temperature. The reaction medium is evaporated to dryness, taken up in ethyl acetate and washed with water, and then with saturated sodium chloride solution. The organic phase is dried over magnesium sulfate and concentrated to dryness to give 130 mg of 4-(2-hydroxy-2-methylpropylamino)benzenesulfonic acid 2-aminobenzothiazol-6-yl ester; compound with trifluoroacetic acid in a yield of 96%.

LC/MS: [M+H]+=394.06, retention time=2.90 min.

INTERMEDIATE 83

Preparation of 4-(2-{6-[4-(2-hydroxy-2-methylpropylamino)-benzenesulfonyloxy]benzothiazol-2-ylcarbamoyl}ethyl)piperidine-1-carboxylic acid tert-butyl ester

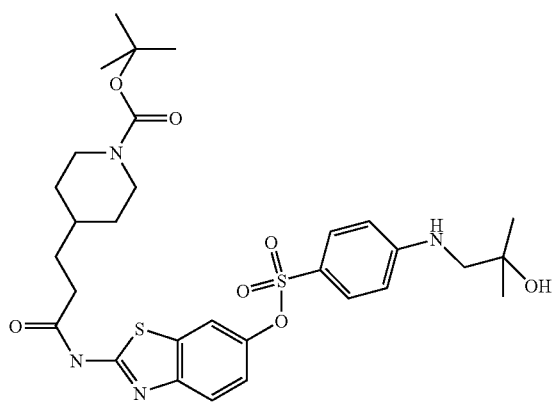

A solution of 1-Boc-piperidin-4-ylpropionic acid (176 mg, 0.686 mmol), HBTU (260 mg, 0.686 mmol) and N,N-diisopropylethylamine (185 mg, 1.435 mmol) in 10 ml of dimethylformamide is stirred for 10 minutes. 4-(2-hydroxy-2-methylpropylamino)benzenesulfonic acid 2-aminobenzothiazol-6-yl ester; compound with trifluoroacetic acid (intermediate 82) (130 mg, 0.33 mmol) is added and the reaction medium is stirred for 48 hours at room temperature. Water is added to the reaction medium and the resulting mixture is then extracted 3 times with ethyl acetate. The organic phase is dried over magnesium sulfate and then concentrated to dryness. The dry residue is purified by reverse-phase chromatography on a 300×20 mm Dynamax C18 column, with a gradient over 5 minutes of 5% to 40% acetonitrile in water supplemented with 0.07% trifluoroacetic acid, and then from 40% to 80% over 30 minutes. The fractions containing the product are evaporated to dryness, to give 111 mg of 4-(2-{6-[4-(2-hydroxy-2-methylpropylamino)-benzenesulfonyloxy]benzothiazol-2-ylcarbamoyl}ethyl)piperidine-1-carboxylic acid tert-butyl ester in a yield of 51%.

LC/MS: [M+H]+=633.00, retention time=3.94 min.

EXAMPLE 84

Preparation of 4-(2-hydroxy-2-methylpropylamino) benzene-sulfonic acid 2-(3-piperidin-4-ylpropionylamino)benzothiazol-6-yl ester hydrochloride

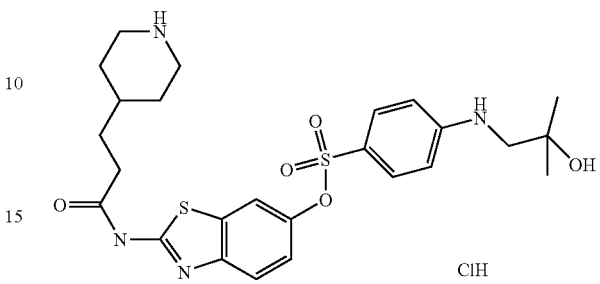

A solution of 4-(2-{6-[4-(2-hydroxy-2-methylpropylamino)-benzenesulfonyloxy]benzothiazol-2-ylcarbamoyl}ethyl)piperidine-1-carboxylic acid tert-butyl ester (110 mg, 0.173 mmol) in 8 ml of dioxane and 8 ml of dioxane/4N HCl is stirred overnight at room temperature. The precipitate formed is filtered off and dissolved in methanol, and the solution is then evaporated to dryness. The residue is washed with ethyl acetate, to give 103 mg of 4-(2-hydroxy-2-methylpropylamino)benzenesulfonic acid 2-(3-piperidin-4-ylpropionylamino)benzothiazol-6-yl ester hydrochloride in a yield of 95%.

LC/MS (method A1): [M+H]+=533.04, retention time=2.66 min.

NMR: 1H NMR spectrum at 300 MHz on a Bruker Avance DPX-300 spectrometer with the chemical shifts (δ in ppm)—in the solvent dimethyl sulfoxide-$d_6$ (DMSO-$d_6$) referenced to 2.50 ppm:

For 80% of the mixture, we have:

1.13 (s, 6H); from 1.22 to 1.40 (m, 2H); from 1.42 to 1.65 (m, 3H), from 1.75 to 1.85 (m, 2H); from 2.40 to 2.58 (partially masked m, 2H); from 2.75 to 2.90 (m, 2H); 3.02 (s, 2H); from 3.15 to 3.30 (m, 2H); 6.73 (broad d, J=9.0 Hz, 2H); 6.97 (dd, J=2.5 and 8.5 Hz, 1H); 7.41 (broad d, J=9.0 Hz, 2H); 7.65 (d, J=8.5 Hz, 1H); 7.70 (d, J=2.5 Hz, 1H); from 8.32 to 8.53 (broad m, 1H); from 8.65 to 8.80 (broad m, 1H); 12.4 (broad s, 1H).

IR:KBr ps 3405; 2971; 1725; 1597; 1539; 1470; 1365; 1161; 1094; 915; 856; 748 and 578 cm$^{-1}$

EXAMPLE 85

Preparation of 5-pyridin-2-ylthiophene-2-sulfonic acid 2-(cyclopropanecarbonylamino)benzothiazol-6-yl ester

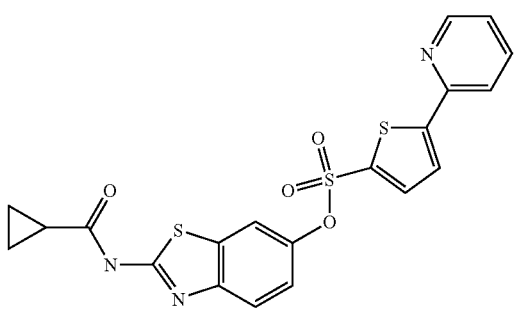

A solution of cyclopropanecarboxylic acid (6-hydroxybenzothiazol-2-yl)amide (intermediate 6) (60 mg, 0.256 mmol), pyridine (80 μl, 0.991 mmol), 4-dimethylaminopyridine (3 mg, 0.025 mmol) and 5-(2-pyridyl)thiophene-2-sulfonyl chloride (99 mg, 0.384 mmol) in 2 ml of acetone is stirred for 24 hours at 40° C. The reaction medium is concentrated to dryness, taken up in 2 ml of DMSO and purified 4 times by preparative LC/MS (method B) to give 10 mg of 5-pyridin-2-ylthiophene-2-sulfonic acid 2-(cyclopropanecarbonyl-amino)benzothiazol-6-yl ester.

NMR: 1H NMR spectrum at 300 MHz on a Bruker Avance DPX-300 spectrometer with the chemical shifts (δ in ppm)— in the solvent dimethyl sulfoxide-d6 (DMSO-$d_6$) referenced to 2.50 ppm:

from 0.98 to 1.10 (m, 4H); 1.90 (m, 1H); 7.15 (broad d, J=8.5 Hz, 1H); from 7.30 to 7.38 (m, 2H); 7.61 (d, J=4.0 Hz, 1H); 7.67 (broad s, 1H); 7.77 (d, J=4.0 Hz, 1H); 7.87 (broad t, J=8.0 Hz, 1H); 7.99 (broad d, J=8.0 Hz, 1H); 8.55 (broad d, J=5.0 Hz, 1H); 13.5 (broad m, 1H).

MS:IE m/z=457 $M^{+-}$ m/z=389 $(M—C_4H_4O)^{+-}$ m/z=325 (m/z=389-$SO_2$)$^{+-}$ m/z=69 $C_4H_5O$+base peak

EXAMPLE 87

Preparation of 4-(1-oxyl-2,2,6,6-tetramethylpiperidin-4-ylamino)-benzenesulfonic acid 2-(cyclopropanecarbonylamino)benzothiazol-6-yl ester

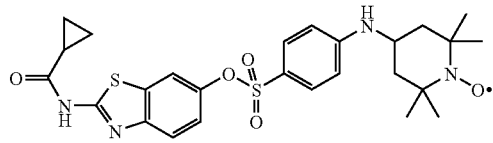

A solution of 4-fluorobenzenesulfonic acid 2-(cyclopropanecarbonylamino)-benzothiazol-6-yl ester (example 7) (0.352 mmol, 138 mg), 4-amino-TEMPO (0.387 mmol, 66 mg) and cesium carbonate (0.352 mmol, 114 mg) in 3.5 ml of dimethylsulfoxide is stirred for 24 hours. 4-Amino-TEMPO is added twice (2 times 66 mg) after 24 and 48 hours. After 48 hours, the reaction is placed at room temperature for 48 hours. The solution is then diluted with water, extracted with ethyl acetate, washed with saturated sodium chloride solution and dried over sodium sulfate, and then evaporated to dryness, to give 258 mg of crude product. This product is purified by flash chromatography on a cartridge of 5 g of silica. The eluents used are, respectively, dichloromethane and then dichloromethane with 1% of 7M 0.01% ammoniacal methanol. 28 mg of 4-(1-oxyl-2,2,6,6-tetramethylpiperidin-4-ylamino) benzenesulfonic acid 2-(cyclopropanecarbonylamino)benzothiazol-6-yl ester are obtained in a yield of 14%.

MS:ES m/z=544 $MH^+$ base peak

IR:KBr

3388; 3252; 2925; 1686; 1598; 1546; 1451; 1327; 1266; 1167; 1094; 907; 852 and 747 $cm^{-1}$

INTERMEDIATE 88

Synthesis of 4-[2-(bis-benzyloxyphosphoryloxy)-2-methyl-propylamino]benzenesulfonic acid 2-(cyclopropanecarbonylamino)benzo-thiazol-6-yl ester

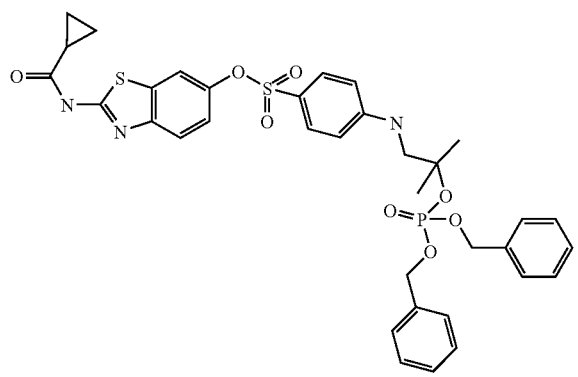

A solution of 4-(2-hydroxy-2-methylpropylamino)benzenesulfonic 2-(cyclopropanecarbonylamino)benzothiazol-6-yl ester (example 11) (0.855 mmol, 394 mg), 1H-tetrazole (2.563 mmol, 179 mg) and dibenzyl diisopropyl phosphoramidite (1.70 mmol, 590 mg) in 6.4 ml of dichloromethane is stirred at room temperature for 2 hours. The reaction medium is cooled to 7° C. and a solution of 3-chloroperoxybenzoic acid (1.025 mmol, 252 mg) in 1.2 ml of dichloromethane is added slowly. The reaction medium is stirred overnight.

10 ml of 1 M sodium metabisulfite solution are added. The organic phase is then washed with 10 ml of 1 M sodium metabisulfite solution, with twice 10 ml of saturated sodium bicarbonate solution and then with 10 ml of saturated sodium chloride solution.

The organic phase is dried over magnesium sulfate, filtered and concentrated to dryness. The dry residue obtained is dissolved in dichloromethane and then purified on an Interchim flash cartridge containing 50 g of silica of porosity 15-35 μm, with a gradient of 20% to 50% ethyl acetate in cyclohexane. After evaporating the solvent from the fractions containing the expected product, 419 mg of 4-[2-(bis-benzyloxyphosphoryloxy)-2-methylpropylamino]benzenesulfonic acid 2-(cyclopropane carbonylamino)-benzothiazol-6-yl ester are obtained in a yield of 68%.

LC/MS (method A1): [M+H]+=722.13, retention time: 4.13 min.

EXAMPLE 89

Synthesis of 4-(2-methyl-2-phosphonooxypropylamino)benzene-sulfonic acid 2-(cyclopropanecarbonylamino)benzothiazol-6-yl ester

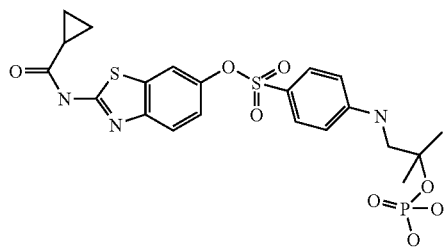

300 mg of 10% palladium-on-charcoal are added to a solution of 4-[2-(bis-benzyloxyphosphoryloxy)-2-methylpropylamino]benzenesulfonic acid 2-(cyclopropanecarbonylamino)benzothiazol-6-yl ester (intermediate 88) (0.441 mmol, 318 mg) and ammonium formate (4.41 mmol, 278 mg) in 15 ml of ethanol.

The reaction medium is refluxed overnight with stirring. LC/MS analysis indicates that there is monobenzyl product remaining. 280 mg (4.41 mmol) of ammonium formate and 100 mg of 10% palladium-on-charcoal are added and the reaction medium is refluxed for 6 hours. The reaction medium is filtered and then concentrated. The oil obtained is returned to reaction with 278 mg of ammonium formate (4.41 mmol) and 300 mg of 10% palladium-on-charcoal in 15 ml of ethanol. The reaction medium is refluxed for 1 hour 20 minutes with stirring. The reaction medium is filtered and concentrated to dryness. The residue obtained is purified by preparative LC/MS (method B) to give 6.2 mg of 4-(2-methyl-2-phosphonooxypropylamino)benzenesulfonic acid 2-(cyclopropanecarbonylamino)benzothiazol-6-yl ester in a yield of 3%.

NMR: 1H NMR spectrum at 300 MHz on a Bruker Avance DPX-300 spectrometer with the chemical shifts ($\delta$ in ppm)—in the solvent dimethyl sulfoxide-$d_6$ (DMSO-$d_6$) referenced to 2.50 ppm:

from 0.90 to 1.01 (m, 4H); 1.41 (s, 6H); 2.00 (m, 1H); from 3.10 to 3.50 (masked m, 2H); 6.75 (broad d, J=9.0 Hz, 2H); 6.89 (broad t, J=6.0 Hz, 1H); 7.97 (dd, J=2.5 and 8.5 Hz, 1H); 7.43 (broad d, J=9.0 Hz, 2H); 7.66 (d, J=8.5 Hz, 1H); 7.70 (d, J=2.5 Hz, 1H); 12.7 (broad s, 1H).

Experimental Protocols on the Biochemical Tests

1. Protocol CDK2/cyclin E:

Purification of the CDK2/cyclin E-$(His)_6$ Complex by IMAC (Immobilized Metal Affinity Chromatography):

Two recombinant baculoviruses bearing the human sequences coding, respectively, for CDK2 and cyclin E (the latter comprising a C-terminal hexahistidine tag) are used to coinfect insect Sf21 cells. Two to three days after the start of coinfection, the cells are harvested by centrifugation and then stored at −40° C. until the time of use. After thawing and mechanical lysis of the cells, the complex present in the lysis supernatant is purified by affinity chromatography on nickel (IMAC), and stored at −80° C.

CDK2/cyclin E Flashplate Test in 96-Well Format

A format in 96-well plates coated with streptavidin is used to test the activity of the compounds on the kinase activity of CDK2/cyclin E.

To perform this test, the biotinylated peptide substrate, a fragment of the pRb protein (biotinyl-SACPLNLPLQN-NHTAADMYLSPVRSPKKKGSTTR-OH) is dissolved at a concentration of 1 mM in kinase buffer (HEPES/NaOH 50 mM, NaCl 1 mM, $MgCl_2$ 5 mM, pH 7.5) in order to constitute a stock solution stored at −20° C. in the form of 110 µl aliquots. On the day of the experiment, an aliquot of this solution is thawed and diluted in kinase buffer containing 1 mM of dithiothreitol, and added to the buffer extemporaneously, in order to obtain a concentration of 14.3 µM. 70 µl of this solution are added to each well of the Flashplate in order to obtain a final substrate concentration of 10 µM during the enzymatic reaction, performed in a final volume of the reaction medium of 100 µl (cf. below).

Intermediate dilutions of inhibitors (products of the invention) at various concentrations are prepared in DMSO from stock solutions at 10 mM in separate tubes. 1000 µM, 333.3 µM, 111.1 µM, 37.03 µM, 12.35 µM, 4.11 µM and 1.37 µM dilutions are thus prepared. 1 µl of each of these solutions (or 1 µl of DMSO for the controls) is transferred into the wells of the test plate.

Into each well are then added 19 µl of a solution of a mixture of adenosine triphosphate (ATP) and of $ATP_\gamma{}^{33}P$ in the kinase buffer at a concentration of 5.26 µM of ATP total and 52.6 µCi/ml of $^{33}P$. The enzymatic reaction is triggered by addition of 10 µl per well of a solution of CDK2/cyclin E at 200 nM in the kinase buffer containing 1 mM of dithiothreitol (or 10 µl of kinase buffer containing 1 mM of dithiothreitol for the reaction blanks).

After addition of each of the reagents, the final volume of each well is 100 µl, the final substrate concentration is 10 µM, the final inhibitor concentrations are 10 µM, 3.33 µM, 1.11 µM, 0.37 µM, 0.123 µM, 0.041 µM and 0.014 µM (according to the concentration of the intermediate dilution), the final ATP concentration is 1 µM, the final amount of $^{33}P$ is 1 µCi/well and the final concentration of CDK2/cyclin E complex is 20 nM. After addition of all the reagents, the plate is incubated at 30° C. with orbital stirring at 650 rpm.

When the incubation is complete, the plate is washed three times with 300 µl per well of PBS (phosphate-buffered saline, pH=7.4, without calcium or magnesium, reference 10010-015, Gibco BRL). The incorporation of $^{33}P$ into the peptide is quantified by scintillation counting using a Packard Topcount.NXT machine. The inhibitory activity of the products of the invention is evaluated by measuring the inhibitory concentration that allows a 50% reduction in the enzymatic activity (IC50).

2. CDK4/cyclin D1 Protocol:

Purification of the CDK4-HA/cyclin D1-$(His)_6$ Complex by IMAC (Immobilized Metal Affinity Chromatography):

Two recombinant baculoviruses bearing the human sequences coding, respectively, for CDK4-HA (C-terminal fusion with the hemaglutinin tag) and for cyclin D1-$(His)_6$ are used to coinfect insect Sf9 cells. Sixty hours after the start of the coinfection, the cells are harvested by centrifugation and then frozen at −20° C. until the time of use. After thawing in buffer A (HEPES 200 mM pH 7.0, NaCl 50 mM, $MgCl_2$ 2 mM, imidazole 25 mM, TCEP 1 mM, glycerol 10% (p/v), NaF 1 mM, $Na_3VO_4$ 1 mM), stirring for 1 hour at 4° C. and centrifugation, the complex present in the lysis supernatant is purified by affinity chromatography on nickel (IMAC) and stored at −80° C.

CDK4/cyclin D1 Flashplate Test in 96-Well Format

A test in 96-well "Flashplate" plates coated with streptavidin is used to evaluate the inhibition of the CDK4/cyclin D1 kinase complex by the products of the invention. To perform this test, the biotinylated peptide substrate, a fragment of the pRb protein (biotinyl-RPPTLSPIPHIPRSPYKFPSSPLR-amide) is dissolved at a concentration of 2 mM in kinase buffer (HEPES/NaOH 50 mM, NaCl 1 mM, $MgCl_2$ 5 mM, pH 7.5) in order to constitute a stock solution stored at −20° C. in the form of 110 µl aliquots. On the day of the experiment, an aliquot of this solution is thawed and diluted in kinase buffer containing 1 mM of dithiothreitol, and added to the buffer extemporaneously, in order to obtain a final peptide concentration of 2.571 µM. 70 µl of this solution are added to each well of the Flashplate in order to obtain a final substrate concentration of 1.8 µM during the enzymatic reaction, performed in a final volume of the reaction medium of 100 µl (cf. below). Intermediate dilutions of inhibitors (products of the invention) at various concentrations are prepared in DMSO from stock solutions at 10 mM in separate tubes. 1000 µM, 333.3 µM, 111.1 µM, 37.03 µM, 12.35 µM, 4.11 µM and 1.37 µM dilutions are thus prepared. 1 µl of each of these solutions (or 1 μl of DMSO for the controls) is then transferred into the wells of the test plate. Into each well are then added 19 μl of a solution of a mixture of adenosine triphosphate (ATP) and of $ATP_\gamma^{33}P$ in the kinase buffer at a concentration of 5.26 μM of ATP total and 78.9 μCi/ml of $^{33}P$. The enzymatic reaction is triggered by addition of 10 μl per well of a solution of CDK4/cyclin D1 at 250 nM in the kinase buffer containing 1 mM of dithiothreitol (or 10 μl of kinase buffer containing 1 mM of dithiothreitol for the reaction blanks). After the various additions, the final volume in each well is 100 μl, the final substrate concentration is 1.8 μM, the final inhibitor concentrations are 10 μM, 3.33 μM, 1.11 μM, 0.37 μM, 0.123 μM, 0.041 μM and 0.014 μM (according to the concentration of the intermediate dilution), the final ATP concentration is 1 μM, the final amount of $^{33}P$ is 1.5 μCi/well and the final concentration of CDK4/cyclin D1 complex is 25 nM.

After addition of all the reagents, the test plate is incubated at 30° C. with orbital stirring at 650 rpm. After the incubation, the plate is washed three times with 300 μl per well of PBS (phosphate-buffered saline, pH=7.4, without calcium or magnesium, reference 10010-015, Gibco BRL). The incorporation of $^{33}P$ into the substrate peptide is quantified by scintillation counting using a Packard Topcount.NXT machine. The inhibitory activity of the products of the invention is evaluated by measuring the inhibitory concentration that allows a 50% reduction in the enzymatic activity (IC50).

3. Aurora 2

The inhibitory effect of the compounds toward the kinase Aurora 2 is determined via a radioactivity scintillation test.

A complete recombinant Aurora 2 enzyme, the N-terminal end of which was labeled with histidine, was expressed in *E. coli* and purified to a quality close to homogeneity.

The C-terminal fragment (Q1687-H2101) of an NuMA (nuclear protein which is associated with the Mitotic Apparatus) expressed in *E. coli*, and the N-terminal end of which was labeled with histidine, was purified by chromatography with nickel chelate and used as substrate in the Aurora 2 kinase test.

The kinase activity of Aurora 2 is measured by scintillation on a microplate saturated with nickel chelate (New England Nuclear, SMP107 model). Each well contains 100 μl of the following solution: 0.02 μM of Aurora 2; 0.5 μM of NuMA substrate; 1 μM of ATP supplemented with 0.5 μCi of ATP-[$^{33}P$]. The solutions are incubated for 45 minutes at 37° C. The test buffer is then removed and the wells are rinsed twice with 300 μl of kinase buffer. The radioactivity is measured in each well using a Packard Model Top Count NXT machine.

The background noise is measured in duplicate in wells containing the radioactive ATP alone containing buffered kinase treated in the same manner as for the other samples.

The activity of the control is determined by measuring in duplicate the radioactivity in the complete test mixture (ATP, Aurora 2 and NuMA substrate), in the absence of test compound.

The inhibition of the activity of Aurora 2 with a compound of the invention is expressed as a percentage of inhibition of the control activity in the absence of test compound. Staurosporin is added to each plate as inhibition control.

| Example | Structure |
|---|---|
| 5 | 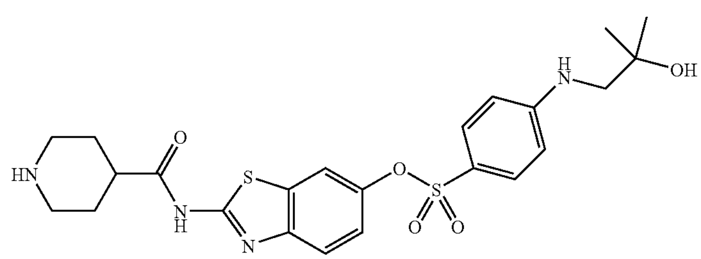 |
| 7 | 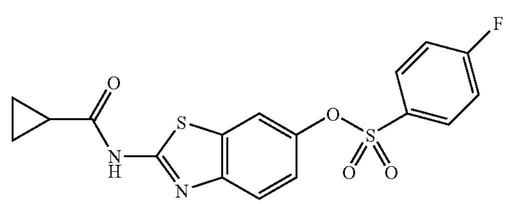 |
| 8 | 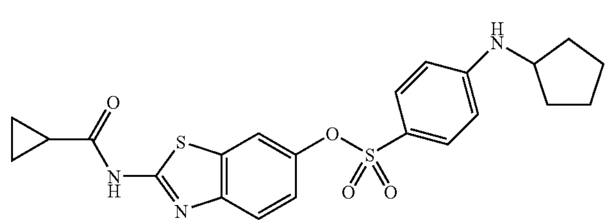 |

-continued
9
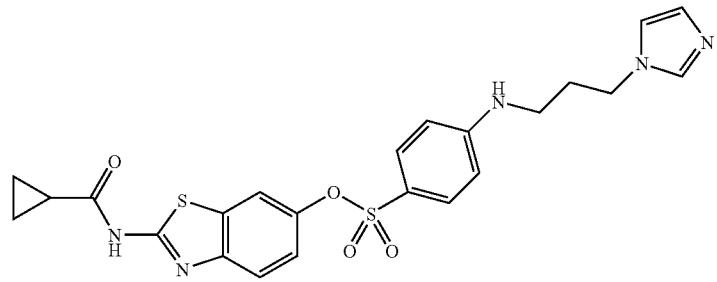
10
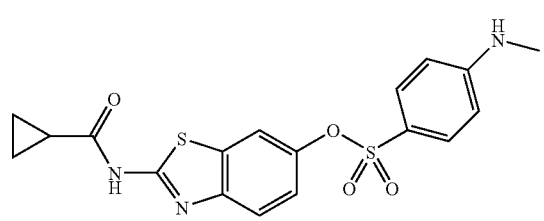
11
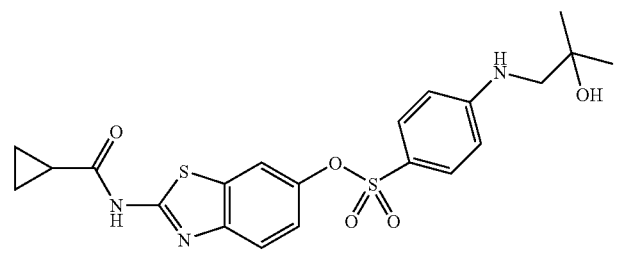
12
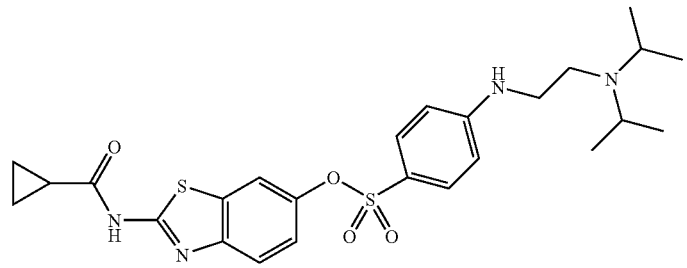
13
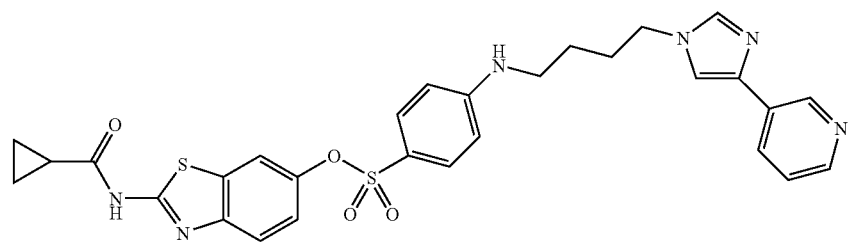

18
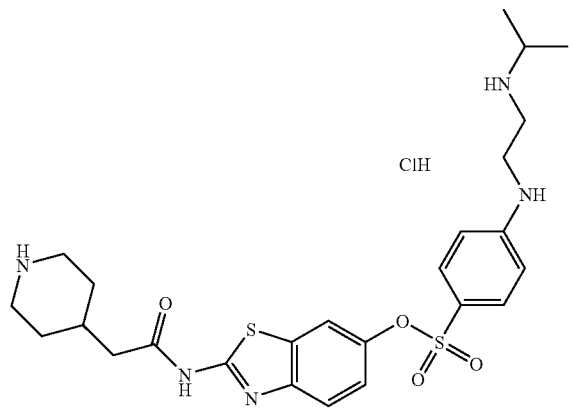
19a
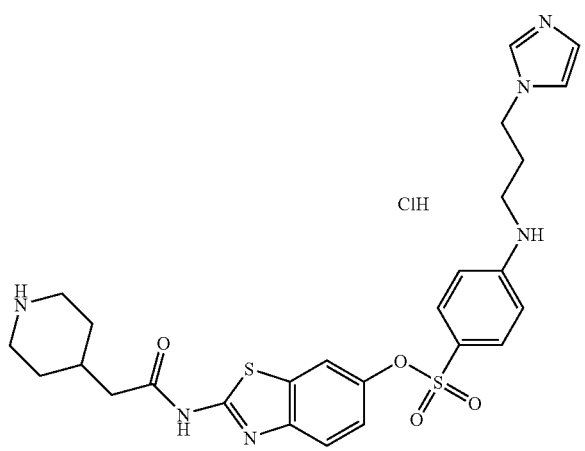
19b
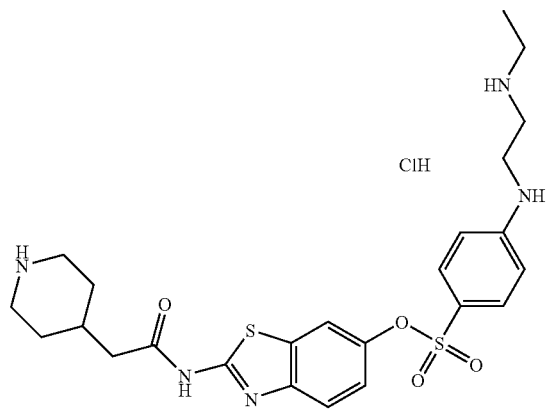

-continued
19c
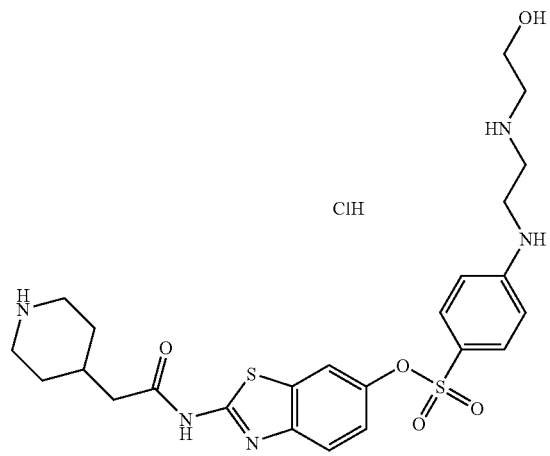
21
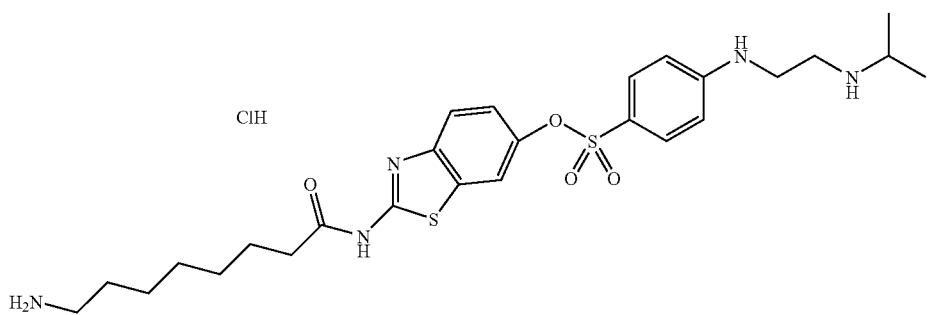
22a
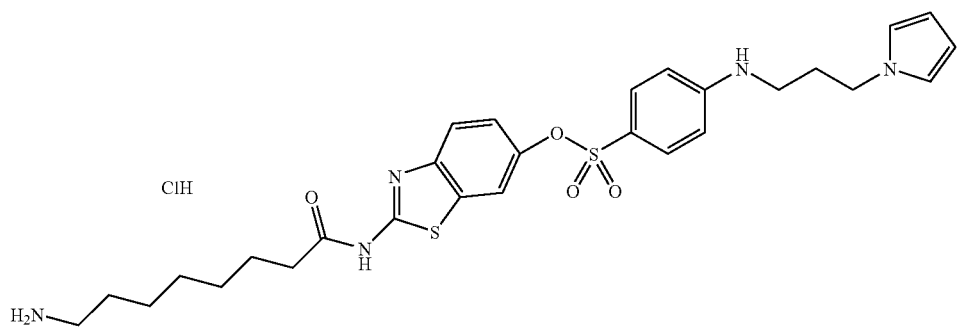
22b
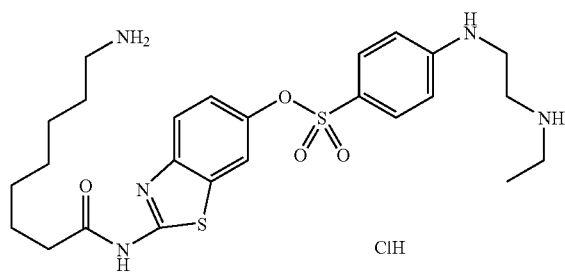

-continued
22c
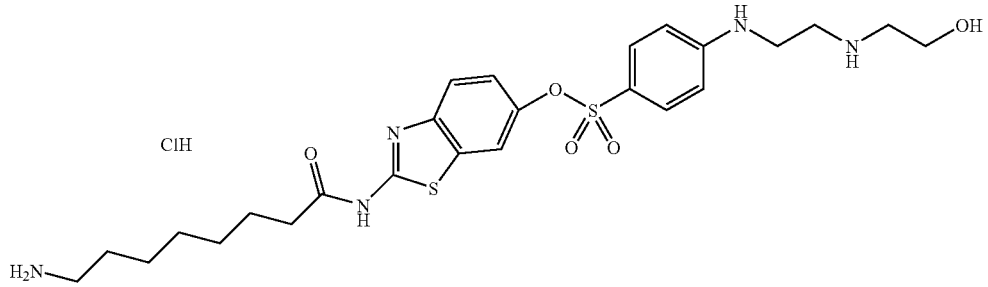
22d
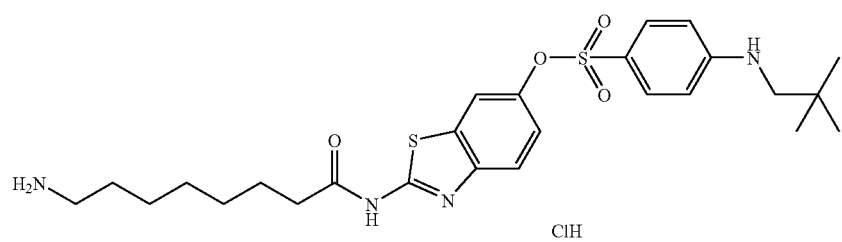
24
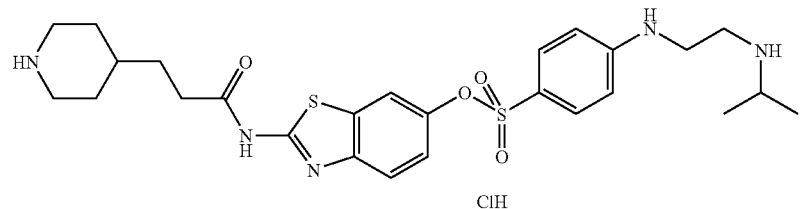
25a
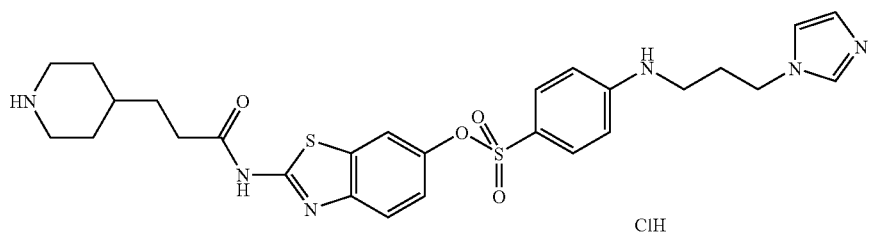
25b
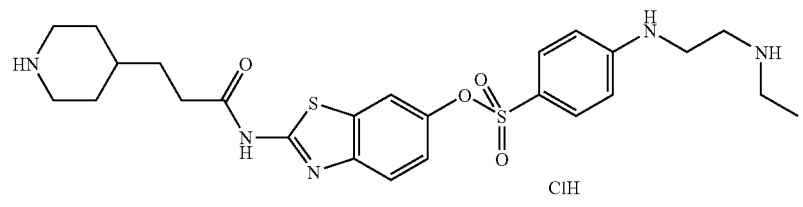
25c
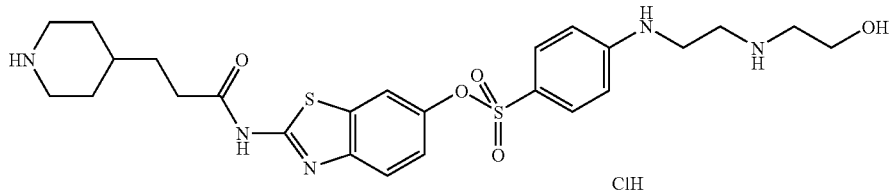

-continued
| | | |
|---|---|---|
| 28 | 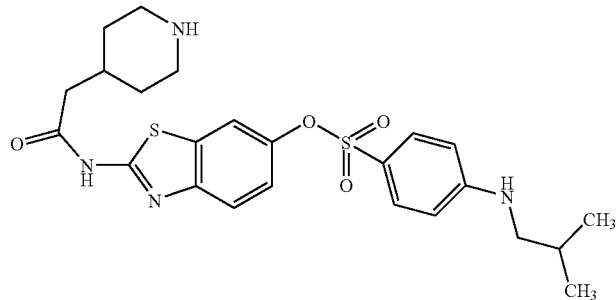 | ClH |
| 29a | 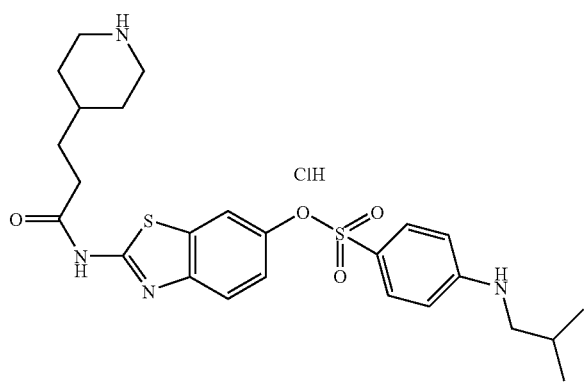 | ClH |
| 29b | 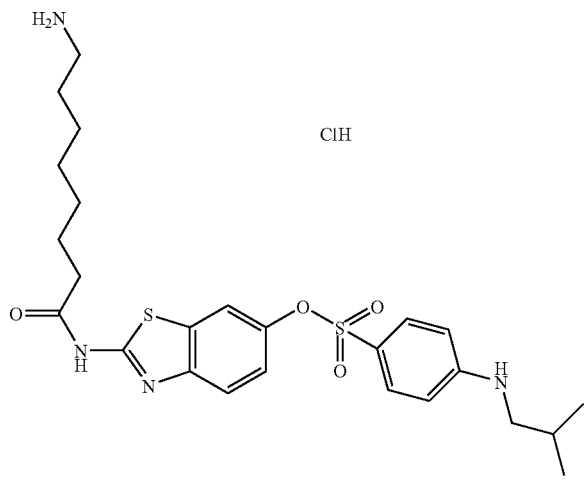 | ClH |
| 33a | ClH 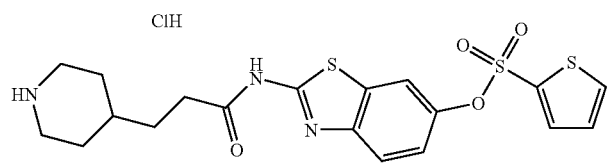 | |
| 33b | 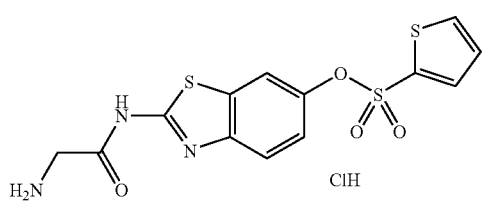 ClH | |

-continued
33c 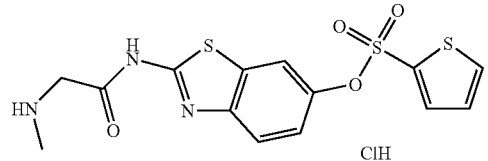
33d 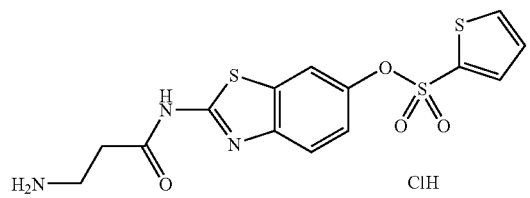
33f 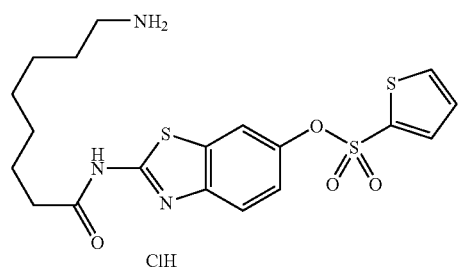
33g 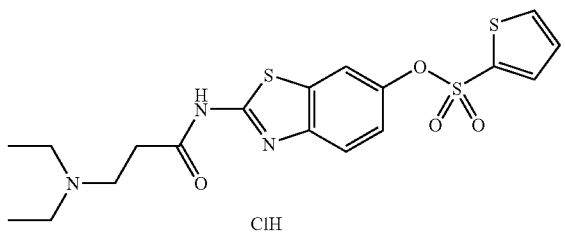
33h 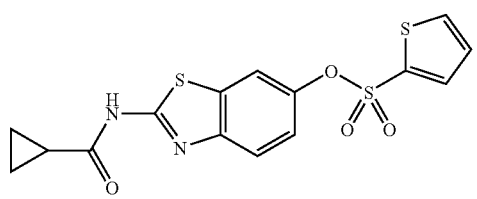
39 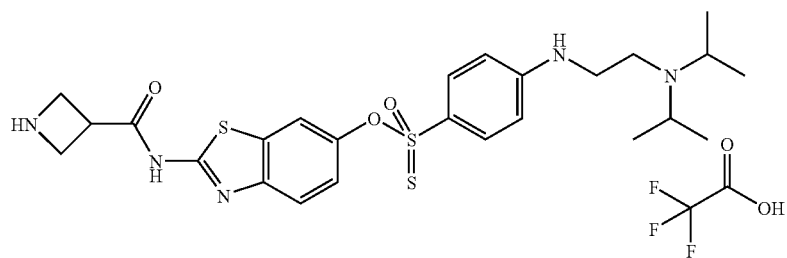
40 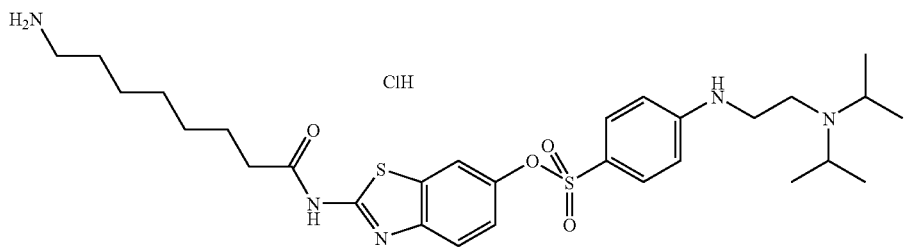

-continued
41
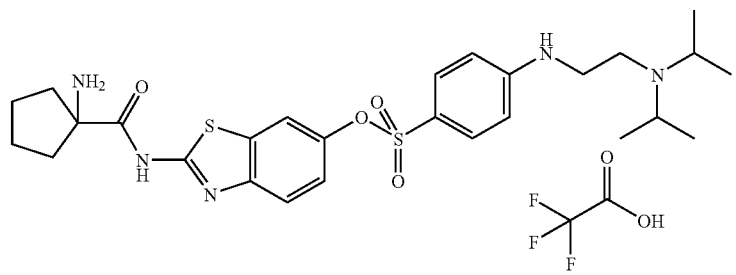
42
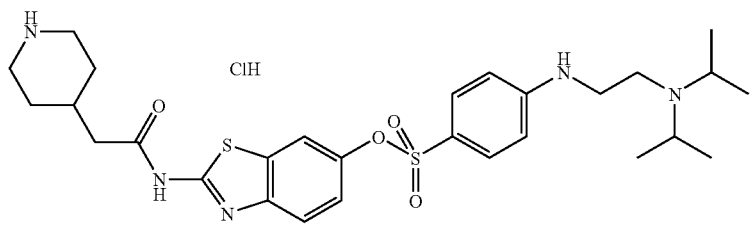
43
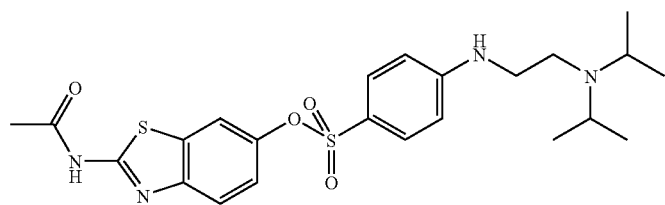
44
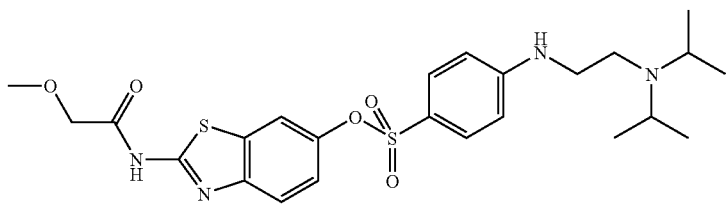
45
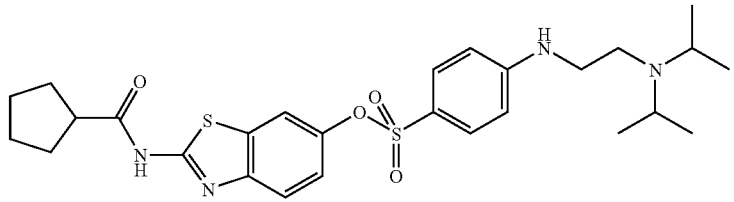
49
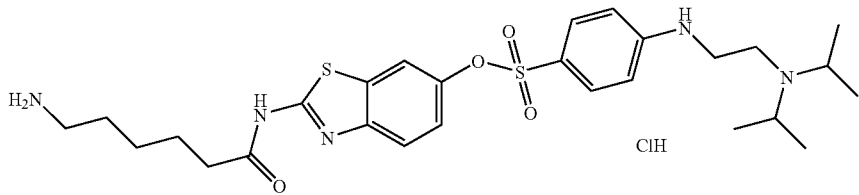

-continued
52 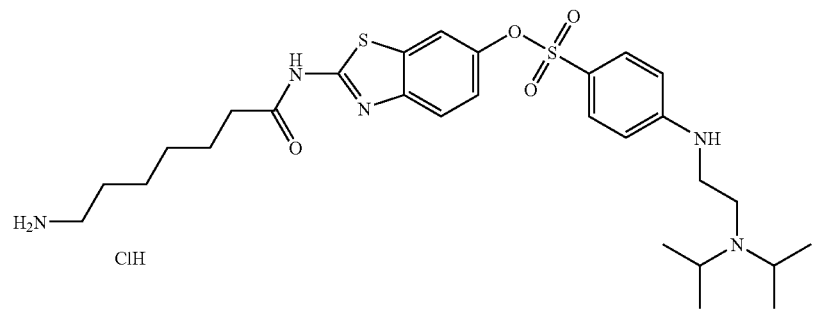
53 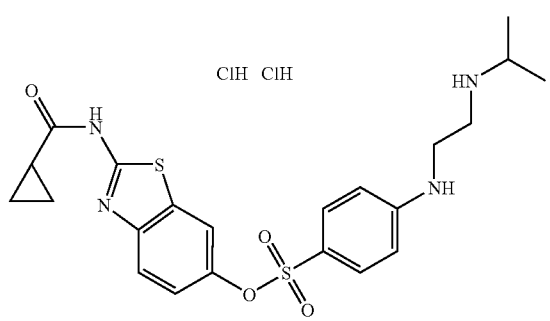
55 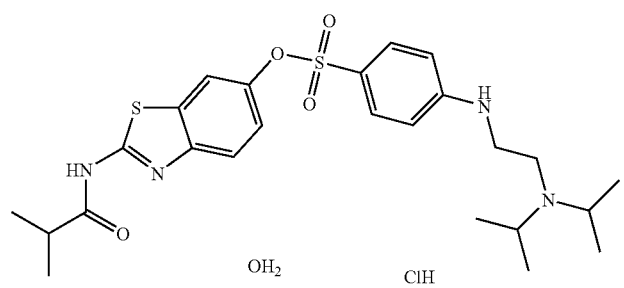
57 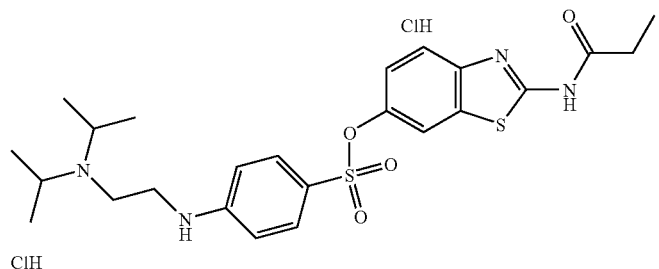
60 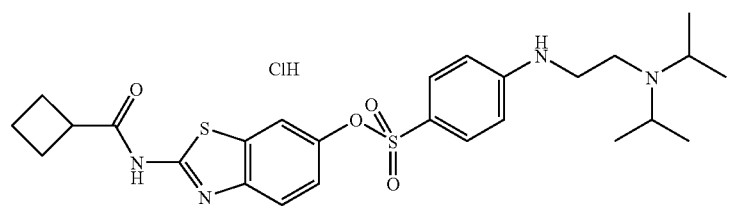

62 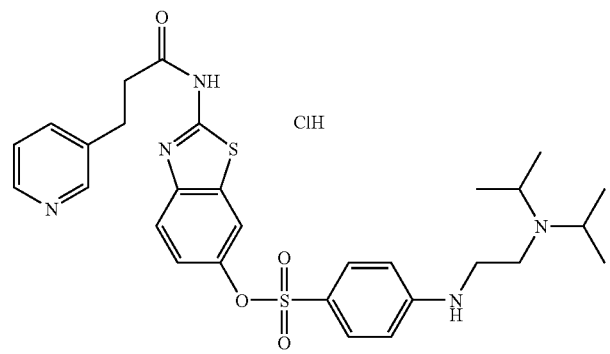
63 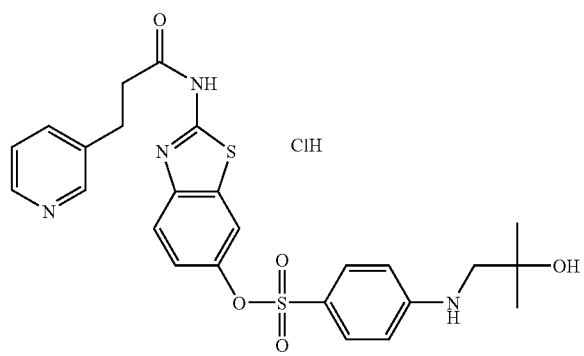
65 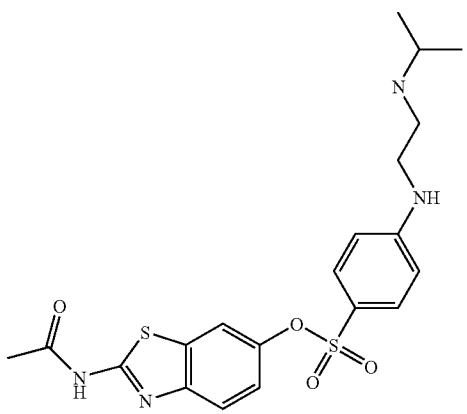
67 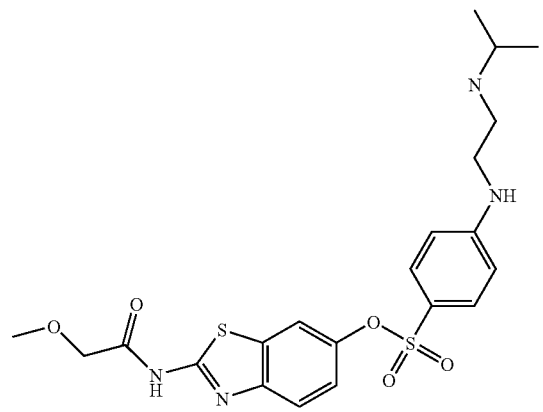

-continued
69
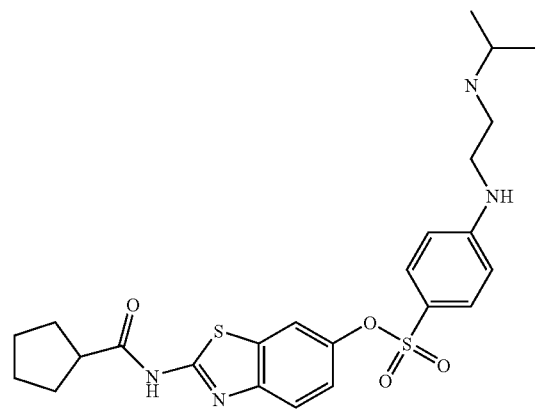
71
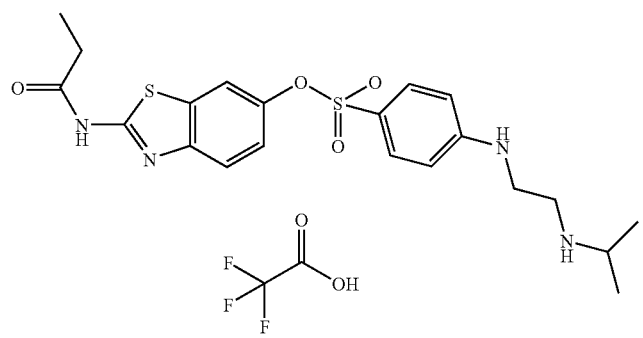
73
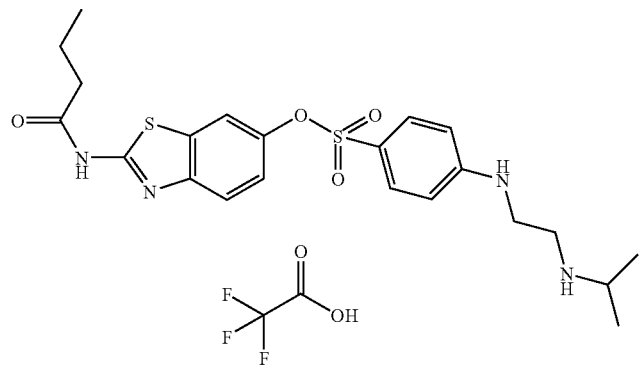
75
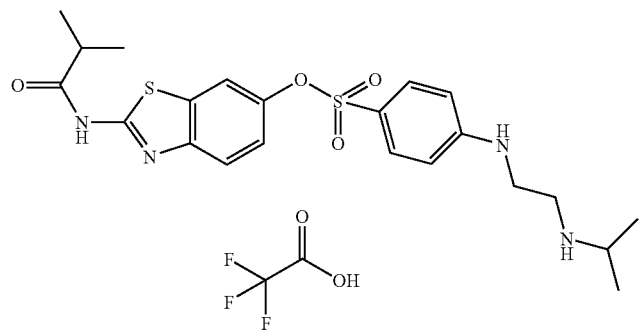

-continued
77 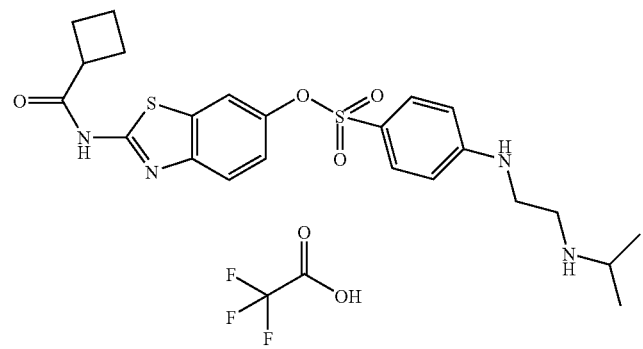
79 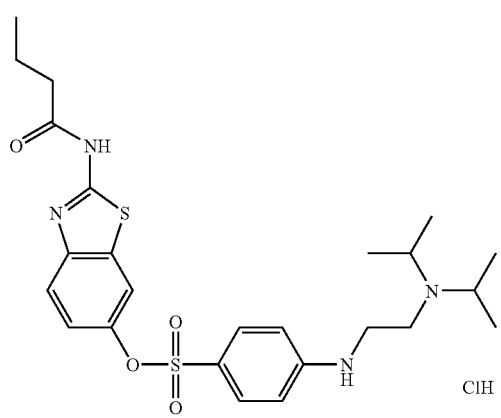
80 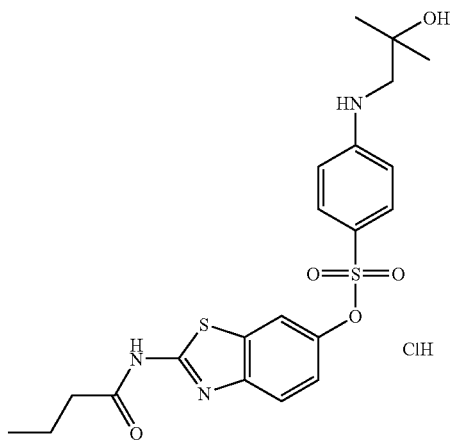
84 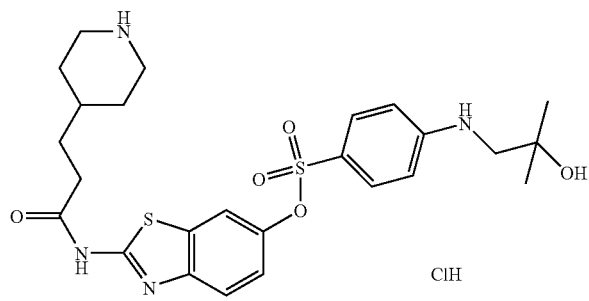

-continued
85 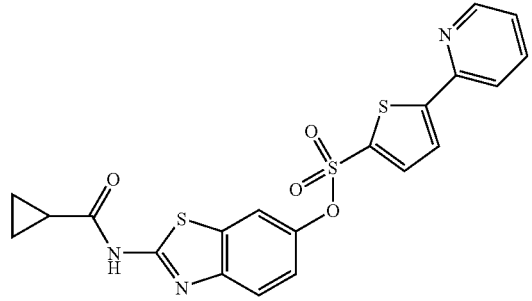
87 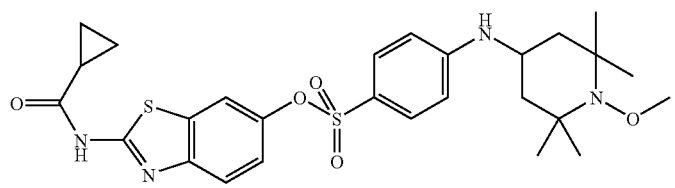
89 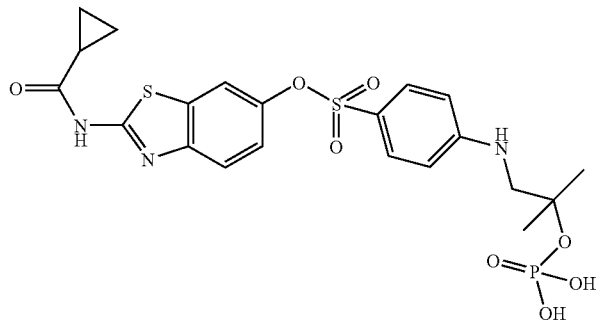
| Example | Aurora 2 IC50 nM | CDK4 IC50 nM | CDK2 IC50 nM | HeLa proliferation EC50 (nM) DG |
|---|---|---|---|---|
| 5 | | 3974 | 995 | |
| 7 | | >10000 | 123 | 1577 |
| 8 | | 899 | 86 | 631 |
| 9 | 65 | 931 | 68 | 611 |
| 10 | 34 | 944 | 92 | 807 |
| 11 | 105 | 924 | 19 | 80 |
| 12 | 172 | 205 | 25 | 16 |
| 13 | | 6863 | 678 | 841 |
| 18 | | 480 | 2683 | |
| 19a | | 471 | 2720 | |
| 19b | | 732 | 5470 | |
| 19c | | 1223 | 5782 | |
| 21 | | 539 | 227 | 2462 |
| 22a | | 609 | 634 | |
| 22b | | 783 | 547 | |
| 22c | | 1570 | 1099 | |
| 22d | | 708 | 69 | 5356 |
| 24 | | 1670 | 864 | >12500 |
| 25a | | 1700 | 365 | >12500 |
| 25b | | 4077 | 5871 | 9962 |
| 25c | | 3888 | 2644 | >12500 |
| 28 | | 399 | 266 | 1328 |
| 29a | | 573 | 257 | 1826 |
| 29b | | 368 | 161 | 8955 |
| 33a | 436 | >10000 | 3240 | |
| 33b | | >10000 | 6341 | |
| 33c | | >10000 | 8267 | |
| 33d | | 8271 | 2947 | |
| 33f | | 7101 | 1838 | |
| 33g | 1901 | >10000 | 5003 | |
| 33h | 68 | 358 | 6981 | 4427 |
| 39 | | 2326 | 3064 | |

-continued

|    |      |        |        |        |
| -- | ---- | ------ | ------ | ------ |
| 40 |      | 253    | 209    | 7551   |
| 41 | 325  | >10000 | >10000 | 8391   |
| 42 |      | 202    | 1143   |        |
| 43 | 2012 | 119    | 49     | 36     |
| 44 | 3078 | 313    | 108    | 76     |
| 45 | 2894 | 341    | 136    | 289    |
| 49 |      | 328    | 183    | 2705   |
| 52 |      | 189    | 112    | 2950   |
| 53 | 172  | 205    | 25     | 16     |
| 55 | 5828 | 221    | 73     | 43     |
| 57 | 3178 | 125    | 40     | 79     |
| 60 | 2804 | 265    | 105    | 199    |
| 62 |      | 236    | 75     | 296    |
| 63 | 1046 | 1389   | 79     | 8371   |
| 65 | 826  | 170    | 107    | 122    |
| 67 |      | 1217   | 294    | >12500 |
| 69 |      | 914    | 299    | 1126   |
| 71 |      | 424    | 175    | 2169   |
| 73 |      | 246    | 185    | 249    |
| 75 |      | 874    | 445    | 195    |
| 77 |      | 1012   | 419    | 179    |
| 79 |      | 70     | 43     | 140    |
| 80 |      | 674    | 57     | 408    |
| 84 |      | 683    | 220    |        |
| 85 | 6941 | >10000 | >10000 | >12500 |
| 87 |      |        | 809    |        |
| 89 | 258  | 3319   | 105    | 2512   |

What is claimed is:

1. A compound of general formula (I):

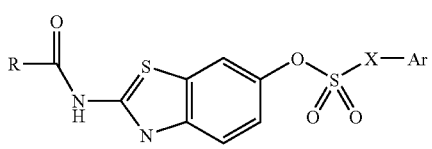

wherein:
- X represents a covalent bond or $(CH_2)_n$, where n equals 1 or 2;
- Ar represents an aryl or heteroaryl group, where the aryl or heteroaryl group is optionally substituted with a group chosen from alkyl, halogen, and $NR_1R_2$ (where $R_1$ and $R_2$ are chosen from hydrogen, alkyl and cycloalkyl, or $R_1$ and $R_2$ may together form a heterocyclic or heteroaryl radical, these groups themselves being optionally substituted), or the aryl or heteroaryl group is optionally substituted with a group chosen from $SO_2$alkyl, Salkyl, alkoxy, heteroaryl and aryl; and
- R represents hydrogen, an alkyl, cycloalkyl, heterocycloalkyl, alkoxy, cycloalkoxy, heterocycloalkoxy or amino group where R may be optionally substituted with one or more groups chosen from alkyl, cycloalkyl, heterocycloalkyl, aryl, heteroaryl, alkoxy, cycloalkoxy, heterocycloalkoxy, hydroxyl, halogen and amino; or a pharmaceutically acceptable salt thereof.

2. A compound according to claim 1, wherein the substituents on the groups $R_1$ and $R_2$ are chosen from hydroxyl, heteroaryl, and cycloalkyl.

3. A compound according to claim 1, wherein the alkyl groups are straight or branched chains containing 1 to 10 carbon atoms.

4. A compound according to claim 1, wherein the cycloalkyl groups are cyclic alkyl chains containing 3 to 10 carbon atoms.

5. A compound according to claim 1, wherein the heterocycloalkyl groups are cyclic alkyl chains containing 3 to 10 carbon atoms and containing at least one hetero atom chosen from O, N and S.

6. A compound according to claim 1, wherein, on the groups $NR_1R_2$, one of the groups $R_1$ or $R_2$ is a hydrogen atom.

7. A compound according to claim 1, wherein all the groups R, $R_1$ and $R_2$ are optionally substituted with an alkyl, cycloalkyl, heterocycloalkyl, heteroaryl, aryl, amino, hydroxyl, alkoxy or halogen group.

8. A compound according to claim 1, wherein the aryl and heteroaryl radicals are chosen from monocyclic radicals optionally comprising one or more hetero atoms chosen from O, N and S, or radicals fused to another 5- or 6-membered ring and optionally comprising 1 to 3 hetero atoms chosen from O, N and S.

9. A compound according to claim 1, wherein the aryl or heteroaryl radicals are chosen from optionally substituted phenyl, pyridyl, pyrimidine, triazinyl, pyrrolyl, imidazolyl, thiazolyl, furyl, thienyl, indolyl, azaindazolyl, isobenzofuryl, isobenzothienyl, benzoxazolyl, benzothiazolyl, quinolyl, isoquinolyl, cinnolyl, quinazolyl, naphthyridyl, triazolyl and tetrazolyl groups.

10. The compound according to claim 9, wherein the aryl and heteroaryl groups are chosen from optionally substituted phenyl, thienyl, and imidazolyl groups.

11. The compound according to claim 10, wherein the phenyl group is substituted with a group chosen from amino monoalkylamino and halogen.

12. The compound according to claim 11 wherein the halogen is chosen from chlorine and fluorine.

13. The compound according to claim 11, wherein the aryl groups are chosen from di- and trifluorophenyls and monoalkylaminophenyls.

14. A compound according to claim 1, wherein X represents a covalent bond.

15. The compound according to claim 1, wherein R represents a cycloalkyl radical.

16. A compound selected from the group consisting of:

4-(2-hydroxy-2-methylpropylamino)benzenesulfonic acid 2-[(piperidine-4-carbonyl)-amino]benzothiazol-6-yl ester;

4-fluorobenzenesulfonic acid 2-(cyclopropanecarbonylamino)benzothiazol-6-yl ester;

4-cyclopentylaminobenzenesulfonic acid 2-(cyclopropanecarbonylamino)benzothiazol-6-yl ester;

4-(3-imidazol-1-ylpropylamino)benzenesulfonic acid 2(cyclopropanecarbonylamino)benzothia 6-yl ester;

4-methylaminobenzenesulfonic acid 2-(cyclopropanecarbonylamino)benzothiazol-6-yl ester;

4-(2-hydroxy-2-methylpropylamino)benzenesulfonic acid 2-(cyclopropanecarbonylamino)-benzothiazol-6-yl ester;

4-(2-diisopropylaminoethylamino)benzenesulfonic acid 2-(cyclopropanecarbonylamino)-benzothiazol-6-yl ester;

4-[4-(4-pyrid-3-ylimidazol-1-yl)butylamino]benzenesulfonic acid 2-(cyclopropanecarbonyl-amino)benzothiazol-6-yl ester;

4-(2-isopropylaminoethylamino)benzenesulfonic acid 2-(2-piperid-4-ylacetylamino)-benzothiazol-6-yl ester hydrochloride;

4-(3-imidazol-1-ylpropylamino)benzenesulfonic acid 2-(2-piperid-4-ylacetylamino)benzothiazol-6-yl ester hydrochloride;

4-(2-ethylaminoethylamino)benzenesulfonic acid 2-(2-piperid-4-ylacetylamino)benzothiazol-6-yl ester hydrochloride;

4-[2-(2-hydroxyethylamino)ethylamino]benzenesulfonic acid 2-(2-piperid-4-ylacetyl-amino)benzothiazol-6-yl ester hydrochloride;

4-(2-hydroxy-2-methylpropylamino)benzenesulfonic acid 2-(2-piperid-4-ylacetylamino)-benzothiazol-6-yl ester hydrochloride;

4-(2-isopropylaminoethylamino)benzenesulfonic acid 2-(8-aminooctanoylamino)benzothiazol-6-yl ester hydrochloride;

4-(3-imidazol-1-ylpropylamino)benzenesulfonic acid 2-(8-aminooctanoylamino)benzothiazol-6-yl ester hydrochloride;

4-(2-ethylaminoethylamino)benzenesulfonic acid 2-(8-aminooctanoylamino)benzothiazol-6-yl ester;

4-[2-(2-hydroxyethylamino)ethylamino]benzenesulfonic acid 2-(8-aminooctanoylamino)benzo-thiazol-6-yl ester hydrochloride;

4-(2-hydroxy-2-methylpropylamino)benzenesulfonic acid 2-(8-aminooctanoylamino)-benzothiazol-6-yl ester hydrochloride;

4-(2-isopropylaminoethylamino)benzenesulfonic acid 2-(3-piperid-4-ylpropionylamino)-benzothiazol-6-yl ester hydrochloride;

4-(3-imidazol-1-ylpropylamino)benzenesulfonic acid 2-(3-piperid-4-ylpropionylamino)-benzothiazol-6-yl ester hydrochloride;

4-(2-ethylaminoethylamino)benzenesulfonic acid 2-(3-piperid-4-ylpropionylamino)benzothiazol-6-yl ester hydrochloride;

4-[2-(2-hydroxyethylamino)ethylamino]benzenesulfonic acid 2-(3-piperid-4-ylpropionyl-amino)benzothiazol-6-yl ester hydrochloride;

4-isobutylaminobenzenesulfonic acid 2-(2-piperid-4-ylacetylamino)benzothiazol-6-yl ester hydrochloride;

4-isobutylaminobenzenesulfonic acid 2-(3-piperid-4-ylpropionylamino)benzothiazol-6-yl ester hydrochloride;

4-isobutylaminobenzenesulfonic acid 2-(8-aminooctanoylamino)benzothiazol-6-yl ester hydrochloride;

thiophene-2-sulfonic acid 2-[(piperidine-4-carbonyl)amino]benzothiazol-6-yl ester; compound with trifluoroacetic acid;

thiophene-2-sulfonic acid 2-(3-piperid-4-ylpropionylamino)benzothiazol-6-yl ester; compound with trifluoroacetic acid;

thiophene-2-sulfonic acid 2-(2-aminoacetylamino)benzothiazol-6-yl ester;

thiophene-2-sulfonic acid 2-(2-methylaminoacetylamino)benzothiazol-6-yl ester; compound with trifluoroacetic acid;

thiophene-2-sulfonic acid 2-(3-aminopropionylamino)benzothiazol-6-yl ester; compound with trifluoroacetic acid;

thiophene-2-sulfonic acid 2-(8-aminooctanoylamino)benzothiazol-6-yl ester; compound with trifluoroacetic acid;

thiophene-2-sulfonic acid 2-(3-diethylaminopropionylamino)benzothiazol-6-yl ester; compound with trifluoroacetic acid;

thiophene-2-sulfonic acid 2-(cyclopropanecarbonylamino)benzothiazol-6-yl ester;

4-(2-diisopropylaminoethylamino)benzenesulfonic acid 2-[(azetidine-3-carbonyl)-amino]benzothiazol-6-yl ester;

4-(2-diisopropylaminoethylamino)benzenesulfonic acid 2-(8-aminooctanoylamino)benzothiazol-6-yl ester;

4-(2-diisopropylaminoethylamino)benzenesulfonic acid 2-[(1-aminocyclopentane-carbonyl)amino]benzothiazol-6-yl ester;

4-(2-diisopropylaminoethylamino)benzenesulfonic acid 2-(2-piperid-4-ylacetylamino)-benzothiazol-6-yl ester;

4-(2-diisopropylaminoethylamino)benzenesulfonic acid 2-acetylaminobenzothiazol-6-yl ester;

4-(2-diisopropylaminoethylamino)benzenesulfonic acid 2-(2-methoxyacetylamino)benzothiazol-6-yl ester;

4-(2-diisopropylaminoethylamino)benzenesulfonic acid 2-(cyclopentanecarbonyl-amino)benzothiazol-6-yl ester;

4-(2-diisopropylaminoethylamino)benzenesulfonic acid 2-(6-aminohexanoylamino)benzothiazol-6-yl ester hydrochloride;

4-(2-diisopropylaminoethylamino)benzenesulfonic acid 2-(7-aminoheptanoyl-amino)benzothiazol-6-yl ester hydrochloride;

4-(2-isopropylaminoethylamino)benzenesulfonic 2-(cyclopropanecarbonylamino)benzothiazol-6-yl ester hydrochloride;

4-(2-diisopropylaminoethylamino)benzenesulfonic acid 2-isobutyrylaminobenzothiazol-6-yl ester hydrochloride;

4-(2-diisopropylaminoethylamino)benzenesulfonic acid 2-propionylaminobenzothiazol-6-yl ester hydrochloride;

4-(2-hydroxy-2-methylpropylamino)benzenesulfonic acid 2-propionylaminobenzothiazol-6-yl ester;

4-(2-diisopropylaminoethylamino)benzenesulfonic acid 2-(cyclobutane-carbonylamino)benzothiazol-6-yl ester hydrochloride;

4-fluorobenzenesulfonic acid 2-(3-pyridin-3-ylpropionylamino)benzothiazol-6-yl ester;

4-(2-diisopropylaminoethylamino)benzenesulfonic acid 2-(3-pyridin-3-yl-propionylamino)benzothiazol-6-yl ester hydrochloride;

4-(2-hydroxy-2-methylpropylamino)benzenesulfonic acid 2-(3-pyridin-3-yl-propionylamino)benzothiazol-6-yl ester hydrochloride;

4-(1-oxyl-2,2,6,6-tetramethylpiperidin-4-ylamino)benzenesulfonic acid 2-(cyclopropanecarbonylamino)benzothiazol-6-yl ester;

4-(2-hydroxy-2-methylpropylamino)benzenesulfonic acid 2-(3-piperidin-4-yl-propionylamino)benzothiazol-6-yl ester hydrochloride;

4-(2-diisopropylaminoethylamino)benzenesulfonic acid 2-butyrylaminobenzothiazol-6-yl ester hydrochloride;

4-(2-isopropylaminoethylamino)benzenesulfonic acid 2-butyrylaminobenzothiazol-6-yl ester; compound with trifluoroacetic acid;

4-(2-isopropylaminoethylamino)benzenesulfonic acid 2-isobutyrylaminobenzothiazol-6-yl ester; compound with trifluoroacetic acid;

4-(2-hydroxy-2-methylpropylamino)benzenesulfonic acid 2-butyrylaminobenzothiazol-6-yl ester hydrochloride;

4-(2-isopropylaminoethylamino)benzenesulfonic acid 2-propionylaminobenzothiazol-6-yl ester; compound with trifluoroacetic acid;

4-(2-isopropylaminoethylamino)benzenesulfonic acid 2-acetylaminobenzothiazol-6-yl ester;

4-(2-isopropylaminoethylamino)benzenesulfonic acid 2-acetylaminobenzothiazol-6-yl ester hydrochloride;

4-(2-isopropylaminoethylamino)benzenesulfonic acid 2-(2-methoxyacetylamino)benzothiazol-6-yl ester;

4-(2-isopropylaminoethylamino)benzenesulfonic acid 2-(cyclopentane-carbonylamino)benzothiazol-6-yl ester;

4-(2-isopropylaminoethylamino)benzenesulfonic acid 2-(cyclobutanecarbonyl-amino)benzothiazol-6-yl ester; compound with trifluoroacetic acid;

1-methyl-1H-imidazole-4-sulfonic acid 2-(cyclopropanecarbonylamino)benzothiazol-6-yl ester;

5-pyridin-2-ylthiophene-2-sulfonic acid 2-(cyclopropanecarbonylamino)benzothiazol-6-yl ester; and 4-(2-methyl-2-phosphonooxypropylamino)benzenesulfonic acid 2-(cyclopropanecarbonylamino)benzothiazol-6-yl ester.

17. A compound which is 4-(2-isopropylaminoethylamino)benzenesulfonic acid 2-acetylaminobenzothiazol-6-yl ester, or a pharmaceutically acceptable salt thereof.

18. A compound selected from the group consisting of:

4-(2-hydroxy-2-methylpropylamino)benzenesulfonic acid 2-[(piperidine-4-carbonyl)-amino]benzothiazol-6-yl ester;

4-fluorobenzenesulfonic acid 2-(cyclopropanecarbonylamino)benzothiazol-6-yl ester;

4-cyclopentylaminobenzenesulfonic acid 2-(cyclopropanecarbonylamino)benzothiazol-6-yl ester;

4-(3-imidazol-1-ylpropylamino)benzenesulfonic acid 2-(cyclopropanecarbonylamino)benzothia-zol-6-yl ester;

4-methylaminobenzenesulfonic acid 2-(cyclopropanecarbonylamino)benzothiazol-6-yl ester;

4-(2-hydroxy-2-methylpropylamino)benzenesulfonic acid 2-(cyclopropanecarbonylamino)-benzothiazol-6-yl ester;

4-(2-diisopropylaminoethylamino)benzenesulfonic acid 2-(cyclopropanecarbonylamino)-benzothiazol-6-yl ester;

4-[4-(4-pyrid-3-ylimidazol-1-yl)butylamino]benzenesulfonic acid 2-(cyclopropanecarbonyl-amino)benzothiazol-6-yl ester;

4-(2-isopropylaminoethylamino)benzenesulfonic acid 2-(2-piperid-4-ylacetylamino)-benzothiazol-6-yl ester;

4-(3-imidazol-1-ylpropylamino)benzenesulfonic acid 2-(2-piperid-4-ylacetylamino)benzothiazol-6-yl ester;

4-(2-ethylaminoethylamino)benzenesulfonic acid 2-(2-piperid-4-ylacetylamino)benzothiazol-6-yl ester;

4-[2-(2-hydroxyethylamino)ethylamino]benzenesulfonic acid 2-(2-piperid-4-ylacetyl-amino)benzothiazol-6-yl ester;

4-(2-hydroxy-2-methylpropylamino)benzenesulfonic acid 2-(2-piperid-4-ylacetylamino)-benzothiazol-6-yl ester;

4-(2-isopropylaminoethylamino)benzenesulfonic acid 2-(8-aminooctanoylamino)benzothiazol-6-yl ester;

4-(3-imidazol-1-ylpropylamino)benzenesulfonic acid 2-(8-aminooctanoylamino)benzothiazol-6-yl ester;

4-(2-ethylaminoethylamino)benzenesulfonic acid 2-(8-aminooctanoylamino)benzothiazol-6-yl ester;

4-[2-(2-hydroxyethylamino)ethylamino]benzenesulfonic acid 2-(8-aminooctanoylamino)-benzo-thiazol-6-yl ester;

4-(2-hydroxy-2-methylpropylamino)benzenesulfonic acid 2-(8-aminooctanoylamino)-benzothiazol-6-yl ester;

4-(2-isopropylaminoethylamino)benzenesulfonic acid 2-(3-piperid-4-ylpropionylamino)-benzothiazol-6-yl ester 4-(3-imidazol-1-ylpropylamino)benzenesulfonic acid 2-(3-piperid-4-ylpropionylamino)-benzothiazol-6-yl ester;

4-(2-ethylaminoethylamino)benzenesulfonic acid 2-(3-piperid-4-ylpropionylamino)benzothiazol-6-yl ester;

4-[2-(2-hydroxyethylamino)ethylamino]benzenesulfonic acid 2-(3-piperid-4-ylpropionyl-amino)benzothiazol-6-yl ester;

4-isobutylaminobenzenesulfonic acid 2-(2-piperid-4-ylacetylamino)benzothiazol-6-yl ester;

4-isobutylaminobenzenesulfonic acid 2-(3-piperid-4-ylpropionylamino)benzothiazol-6-yl ester;

4-isobutylaminobenzenesulfonic acid 2-(8-aminooctanoylamino)benzothiazol-6-yl ester;

thiophene-2-sulfonic acid 2-[(piperidine-4-carbonyl)amino]benzothiazol-6-yl ester;

thiophene-2-sulfonic acid 2-(3-piperid-4-ylpropionylamino)benzothiazol-6-yl ester;

thiophene-2-sulfonic acid 2-(2-aminoacetylamino)benzothiazol-6-yl ester;

thiophene-2-sulfonic acid 2-(2-methylaminoacetylamino)benzothiazol-6-yl ester;

thiophene-2-sulfonic acid 2-(3-aminopropionylamino)benzothiazol-6-yl ester;

thiophene-2-sulfonic acid 2-(8-aminooctanoylamino)benzothiazol-6-yl ester;

thiophene-2-sulfonic acid 2-(3-diethylaminopropionylamino)benzothiazol-6-yl ester;

thiophene-2-sulfonic acid 2-(cyclopropanecarbonylamino)benzothiazol-6-yl ester;

4-(2-diisopropylaminoethylamino)benzenesulfonic acid 2-[(azetidine-3-carbonyl)-amino]benzothiazol-6-yl ester;

4-(2-diisopropylaminoethylamino)benzenesulfonic acid 2-(8-aminooctanoylamino)benzothiazol-6-yl ester;

4-(2-diisopropylaminoethylamino)benzenesulfonic acid 2-[(1-aminocyclopentane-carbonyl)amino]benzothiazol-6-yl ester;

4-(2-diisopropylaminoethylamino)benzenesulfonic acid 2-(2-piperid-4-ylacetylamino)-benzothiazol-6-yl ester;

4-(2-diisopropylaminoethylamino)benzenesulfonic acid 2-acetylaminobenzothiazol-6-yl ester;
4-(2-diisopropylaminoethylamino)benzenesulfonic acid 2-(2-methoxyacetylamino)benzothiazol-6-yl ester;
4-(2-diisopropylaminoethylamino)benzenesulfonic acid 2-(cyclopentanecarbonyl-amino)benzothiazol-6-yl ester;
4-(2-diisopropylaminoethylamino)benzenesulfonic acid 2-(6-aminohexanoylamino)benzothiazol-6-yl ester;
4-(2-diisopropylaminoethylamino)benzenesulfonic acid 2-(7-aminoheptanoyl-amino)benzothiazol-6-yl ester;
4-(2-isopropylaminoethylamino)benzenesulfonic 2-(cyclopropanecarbonylamino)benzothiazol-6-yl ester;
4-(2-diisopropylaminoethylamino)benzenesulfonic acid 2-isobutyrylaminobenzothiazol-6-yl ester;
4-(2-diisopropylaminoethylamino)benzenesulfonic acid 2-propionylaminobenzothiazol-6-yl ester;
4-(2-hydroxy-2-methylpropylamino)benzenesulfonic acid 2-propionylaminobenzothiazol-6-yl ester;
4-(-2-diisopropylaminoethylamino)benzenesulfonic acid 2-(cyclobutane-carbonylamino)benzothiazol-6-yl ester;
4-fluorobenzenesulfonic acid 2-(3-pyridin-3-ylpropionylamino)benzothiazol-6-yl ester;
4-(2-diisopropylaminoethylamino)benzenesulfonic acid 2-(3-pyridin-3-yl-propionylamino)benzothiazol-6-yl ester;
4-(2-hydroxy-2-methylpropylamino)benzenesulfonic acid 2-(3-pyridin-3-yl-propionylamino)benzothiazol-6-yl ester;
4-(1-oxyl-2,2,6,6-tetramethylpiperidin-4-ylamino)benzenesulfonic acid 2-(cyclopropanecarbonylamino)benzothiazol-6-yl ester;
4-(2-hydroxy-2-methylpropylamino)benzenesulfonic acid 2-(3-piperidin-4-yl-propionylamino)benzothiazol-6-yl ester;
4-(2-diisopropylaminoethylamino)benzenesulfonic acid 2-butyrylaminobenzothiazol-6-yl ester;
4-(2-isopropylaminoethylamino)benzenesulfonic acid 2-butyrylaminobenzothiazol-6-yl ester;
4-(2-isopropylaminoethylamino)benzenesulfonic acid 2-isobutyrylaminobenzothiazol-6-yl ester;
4-(2-hydroxy-2-methylpropylamino)benzenesulfonic acid 2-butyrylaminobenzothiazol-6-yl ester;
4-(2-isopropylaminoethylamino)benzenesulfonic acid 2-propionylaminobenzothiazol-6-yl ester;
4-(2-isopropylaminoethylamino)benzenesulfonic acid 2-acetylaminobenzothiazol-6-yl ester;
4-(2-isopropylaminoethylamino)benzenesulfonic acid 2-(2-methoxyacetylamino)benzothiazol-6-yl ester;
4-(2-isopropylaminoethylamino)benzenesulfonic acid 2-(cyclopentane-carbonylamino)benzothiazol-6-yl ester;
4-(2-isopropylaminoethylamino)benzenesulfonic acid 2-(cyclobutanecarbonyl-amino)benzothiazol-6-yl ester;
1-methyl-1H-imidazole-4-sulfonic acid 2-(cyclopropanecarbonylamino)benzothiazol-6-yl ester;
5-pyridin-2-ylthiophene-2-sulfonic acid 2-(cyclopropanecarbonylamino)benzothiazol-6-yl ester; and
4-(2-methyl-2-phosphonooxypropylamino)benzenesulfonic acid 2-(cyclopropanecarbonylamino)benzothiazol-6-yl ester; or
a pharmaceutically acceptable salt thereof.

\* \* \* \* \*

UNITED STATES PATENT AND TRADEMARK OFFICE
CERTIFICATE OF CORRECTION

PATENT NO. : 7,632,952 B2  Page 1 of 1
APPLICATION NO. : 11/536757
DATED : December 15, 2009
INVENTOR(S) : Deprets et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 163 days.

Signed and Sealed this

Second Day of November, 2010

David J. Kappos
*Director of the United States Patent and Trademark Office*

UNITED STATES PATENT AND TRADEMARK OFFICE
CERTIFICATE OF CORRECTION

PATENT NO. : 7,632,952 B2  Page 1 of 2
APPLICATION NO. : 11/536757
DATED : December 15, 2009
INVENTOR(S) : Stephanie Deprets et al.

It is certified that error appears in the above-identified patent and that said Letters Patent is hereby corrected as shown below:

In column 3, line 11, delete "equals" and insert -- equal --, therefor.

In column 19, line 22, delete "car-boxylic" and insert -- carboxylic --, therefor.

In column 20, line 3, after "(intermediate" delete "is".

In columns 21-22, line 9, after "δ" delete "6".

In column 25, line 36, delete "hydro-chloride" and insert -- hydrochloride --, therefor.

In columns 27-28, line 9, delete "MHZ)" and insert -- MHz) --, therefor.

In columns 27-28, line 42, delete "(broad, s," and insert -- (broad s, --, therefor.

In column 33, line 11, delete "ml." and insert -- min. --, therefor.

In column 50, line 18, after "7.58" insert -- (d, J=2.5 Hz, 1H); 7.64 --.

In column 59, line 1, after "the" delete "is".

In column 64, line 48, after "6-yl" delete "acid".

In column 72, line 45, after "IR:KBr" delete "ps".

In column 73, line 27, delete "$C_4H_5O+$" and insert -- $C_4H_5O^+$ --, therefor.

In column 76, line 40, delete "$MgCl_22$" and insert -- $MgCl_2$ 2 --, therefor.

Signed and Sealed this

Thirtieth Day of November, 2010

David J. Kappos
*Director of the United States Patent and Trademark Office*

In column 103, lines 32-36, in Claim 1, delete " 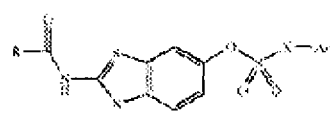 " and insert -- 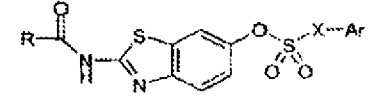 --, therefor.

In column 104, line 56, in Claim 11, delete "amino" and insert -- amino, --, therefor..

In column 105, line 10, in Claim 16, delete "2(" and insert -- 2-( --, therefor.

In column 105, line 10, in Claim 16, delete "benzothia 6-yl" and insert -- benzothiazol-6-yl --, therefor.

In column 108, line 27, in Claim 18, delete "4-(3-imidazol-1-ylpropylamino)benzenesulfonic" and insert the same on Col. 108 Line 28, under "ester" as a new line.

In column 109, line 20, in Claim 18, delete "4-(-2" and insert -- 4-(2 --, therefor.

In column 109, line 22, in Claim 18, delete "4-fluorobenzenesu1fonic" and insert -- 4-fluorobenzenesulfonic --, therefor.